United States Patent
Tian et al.

(10) Patent No.: US 10,781,462 B2
(45) Date of Patent: Sep. 22, 2020

(54) DIBASIC ORGANIC ACID PRODUCING STRAIN AND PREPARATION AND APPLICATION OF SAME

(71) Applicant: TIANJIN INSTITUTE OF INDUSTRIAL BIOTECHNOLOGY, CHINESE ACADEMY OF SCIENCES, Tianjin (CN)

(72) Inventors: Chaoguang Tian, Tianjin (CN); Jingen Li, Tianjin (CN); Chuannan Long, Tianjin (CN); Tao Sun, Tianjin (CN); Liangcai Lin, Tianjin (CN); Jing Xu, Tianjin (CN); Qian Liu, Tianjin (CN); Jingxiao Ji, Tianjin (CN); Wenliang Sun, Tianjin (CN); Yanhe Ma, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 46 days.

(21) Appl. No.: 15/551,165

(22) PCT Filed: Feb. 4, 2016

(86) PCT No.: PCT/CN2016/073573
§ 371 (c)(1),
(2) Date: Aug. 15, 2017

(87) PCT Pub. No.: WO2016/127920
PCT Pub. Date: Aug. 18, 2016

(65) Prior Publication Data
US 2018/0171369 A1 Jun. 21, 2018

(30) Foreign Application Priority Data

Feb. 15, 2015 (CN) .......................... 2015 1 0081668
Mar. 23, 2015 (CN) .......................... 2015 1 0127264
Mar. 23, 2015 (CN) .......................... 2015 1 0129876

(51) Int. Cl.
| | |
|---|---|
| C12P 7/46 | (2006.01) |
| C07K 14/37 | (2006.01) |
| C12N 15/80 | (2006.01) |
| C12N 15/52 | (2006.01) |
| C12N 9/00 | (2006.01) |
| C12N 9/10 | (2006.01) |
| C12P 7/44 | (2006.01) |
| C12P 7/50 | (2006.01) |
| C12N 9/04 | (2006.01) |
| C12R 1/645 | (2006.01) |

(52) U.S. Cl.
CPC ............... *C12P 7/46* (2013.01); *C07K 14/37* (2013.01); *C12N 9/00* (2013.01); *C12N 9/0006* (2013.01); *C12N 9/10* (2013.01); *C12N 9/1096* (2013.01); *C12N 9/93* (2013.01); *C12N 15/52* (2013.01); *C12N 15/80* (2013.01); *C12P 7/44* (2013.01); *C12P 7/50* (2013.01); *C12Y 101/01037* (2013.01); *C12Y 206/01001* (2013.01); *C12Y 602/01004* (2013.01); *C12Y 604/01001* (2013.01); *C12R 1/645* (2013.01)

(58) Field of Classification Search
None
See application file for complete search history.

(56) References Cited

FOREIGN PATENT DOCUMENTS

| | | |
|---|---|---|
| CN | 102597224 | 7/2012 |
| CN | 102947458 | 2/2013 |
| CN | 104844698 | 8/2015 |
| EP | 2194140 | 6/2010 |

OTHER PUBLICATIONS

International Search Report for international application No. PCT/CN2016/073573, dated May 10, 2016 (10 pages, including English translation).
Abstract of "XP_003660869," Genbank, Jan. 4, 2012, 2 pages.
Abstract of "XP_003662692," Genbank, Jan. 4, 2012, 2 pages.
Abstract of "XP_003666955," Genbank, Jan. 4, 2012, 2 pages.
Abstract of "CAD21508," Genbank, Nov. 14, 2006, 2 pages.

*Primary Examiner* — Kagnew H Gebreyesus
(74) *Attorney, Agent, or Firm* — Hamre, Schumann, Mueller & Larson, P.C.

(57) ABSTRACT

Provided are an engineered strain for synthesizing a dibasic organic acid and preparation and application of same. The engineered strain introduces or up-regulates expression of a positive regulator gene for synthesis of a dibasic organic acid, and/or down-regulates expression of a negative regulator gene for synthesis of a dibasic organic acid, as compared with the origin strain of the engineered strain, the producing capability for producing the dibasic organic acid is improved. The dibasic organic acid comprises malic acid, succinic acid, fumaric acid, oxaloacetic acid, glutaric acid, and adipic acid; the expression product of the positive regulator gene comprises aspartate aminotransferase, glutamic acid-aspartate transporter, C4-dicarboxylic acid transporter, pyruvate carboxylase and malate dehydrogenase, glucose transporter; the expression product of the negative regulatory gene comprises succinyl-CoA synthase, and malic acid-alpha ketoglutarate transporter, and the original strain comprises *myceliophthora thermophila, thielavia terrestris, aspergillus*, and *rhizopus*.

17 Claims, 5 Drawing Sheets
Specification includes a Sequence Listing.

SEQUENCE LISTING

```
<160> NUMBER OF SEQ ID NOS: 96

<210> SEQ ID NO 1
<211> LENGTH: 1341
<212> TYPE: DNA
<213> ORGANISM: Myceliophthora thermophila

<400> SEQUENCE: 1
atgtacagac tcggtcgtag ccgcgcattg gcgtcggcct tcgccgcgcc caaggtttct      60
ccctccccca gactccagag cattgcgcaa caacaaagga gagccctgag catccacgag     120
taccgctccg ccgacctcct ccgccagtat ggcatcgata ttccaaaggg cgccgtcgcg     180
acgacggcgg ctgaggccga ggcggtcgcc aagagcatcg gcaccgacga catggtgatc     240
```

-continued

```
aaggctcagg tgctcgccgg cgggcgcggc aagggcagct tcgacaacgg cctcaagggc        300
ggcgttcgcg tcatctactc gcccaccgag gccaagatgt tcgccgagca gatgatcggc        360
cacaagctca tcaccaagca gacgggcgcc gccggccgtc tgtgcaacgc cgtctacatc        420
tgcgagcgca agttcgcccg ccgcgagttc tacctggccg tgctcatgga ccgcgcgtcg        480
cagggacccg tcatcgtctc gtcgtcgcag ggcggcatgg acattgagac ggtcgccaag        540
gagaaccccg acgccatcac gaccacctac atcgacatca acgtgggcgt gacggacgag        600
atcgcgcgcg gcatcgccac caagctgggc ttcagcgagc agtgcatcga ggacgccaag        660
gacaccatca gaacctgta  ccgcatcttc ctcgagaagg acgcgaccca gatcgagatc        720
aacccgctct cggagacgtc ggaccacaag gtcatgtgca tggatgccaa gttcggcttt        780
gacgacaacg ccgagttccg ccagaaggag gtgttcagct ggcgcgacac cacccaggag        840
gacccggagg aggtgcgggc cgccgaggcc gggctcaact tcatcaagct ggacggcgac        900
atcggctgcc tggtcaacgg cgccggcctg gccatggcca ccatggacat tatcaagctc        960
aacggtgggc agccggccaa cttcctcgac gtcgcggcg  cgccacccc  ggcggccatc       1020 aaggaggcct ttgagctcat caccagcgac cccaaggtga cggccatctt tgtcaacatc       1080
tttggcggca tcgtgcgctg cgacgccatc gcccacggcc tcatcaacac ggtcaagtcg       1140
ctcgacctga agatccccat cattgcccgc ctgcagggca ccaacatgga gcaggcccac       1200
cagctcatca cgactcgggg catgaagatc ttctccatcg acgacctgca gagcgccgcc       1260
gagcgcgccg tccagctgtc caaggttgtc aagatggctc gtgacattga cgttggcgtc       1320
gagttcaccc tgggtatctg a                                                 1341
```

<210> SEQ ID NO 2
<211> LENGTH: 446
<212> TYPE: PRT
<213> ORGANISM: Myceliophthora thermophila

<400> SEQUENCE: 2

```
Met Tyr Arg Leu Gly Arg Ser Arg Ala Leu Ala Ser Ala Phe Ala Ala
1               5                   10                  15

Pro Lys Val Ser Pro Ser Pro Arg Leu Gln Ser Ile Ala Gln Gln Gln
                20                  25                  30

Arg Arg Ala Leu Ser Ile His Glu Tyr Arg Ser Ala Asp Leu Leu Arg
            35                  40                  45

Gln Tyr Gly Ile Asp Ile Pro Lys Gly Ala Val Ala Thr Thr Ala Ala
        50                  55                  60

Glu Ala Glu Ala Val Ala Lys Ser Ile Gly Thr Asp Asp Met Val Ile
65                  70                  75                  80

Lys Ala Gln Val Leu Ala Gly Arg Gly Lys Gly Ser Phe Asp Asn
                85                  90                  95

Gly Leu Lys Gly Gly Val Arg Val Ile Tyr Ser Pro Thr Glu Ala Lys
            100                 105                 110

Met Phe Ala Glu Gln Met Ile Gly His Lys Leu Ile Thr Lys Gln Thr
        115                 120                 125

Gly Ala Ala Gly Arg Leu Cys Asn Ala Val Tyr Ile Cys Glu Arg Lys
    130                 135                 140

Phe Ala Arg Arg Glu Phe Tyr Leu Ala Val Leu Met Asp Arg Ala Ser
145                 150                 155                 160

Gln Gly Pro Val Ile Val Ser Ser Ser Gln Gly Gly Met Asp Ile Glu
                165                 170                 175
```

```
Thr Val Ala Lys Glu Asn Pro Asp Ala Ile Thr Thr Tyr Ile Asp
            180                 185                 190

Ile Asn Val Gly Val Thr Asp Glu Ile Ala Arg Gly Ile Ala Thr Lys
            195                 200                 205

Leu Gly Phe Ser Glu Gln Cys Ile Glu Asp Ala Lys Asp Thr Ile Lys
            210                 215                 220

Asn Leu Tyr Arg Ile Phe Leu Glu Lys Asp Ala Thr Gln Ile Glu Ile
225                 230                 235                 240

Asn Pro Leu Ser Glu Thr Ser Asp His Lys Val Met Cys Met Asp Ala
            245                 250                 255

Lys Phe Gly Phe Asp Asp Asn Ala Glu Phe Arg Gln Lys Glu Val Phe
            260                 265                 270

Ser Trp Arg Asp Thr Thr Gln Glu Asp Pro Glu Glu Val Arg Ala Ala
            275                 280                 285

Glu Ala Gly Leu Asn Phe Ile Lys Leu Asp Gly Asp Ile Gly Cys Leu
            290                 295                 300

Val Asn Gly Ala Gly Leu Ala Met Ala Thr Met Asp Ile Ile Lys Leu
305                 310                 315                 320

Asn Gly Gly Gln Pro Ala Asn Phe Leu Asp Val Gly Gly Gly Ala Thr
            325                 330                 335

Pro Ala Ala Ile Lys Glu Ala Phe Glu Leu Ile Thr Ser Asp Pro Lys
            340                 345                 350

Val Thr Ala Ile Phe Val Asn Ile Phe Gly Gly Ile Val Arg Cys Asp
            355                 360                 365

Ala Ile Ala His Gly Leu Ile Asn Thr Val Lys Ser Leu Asp Leu Lys
            370                 375                 380

Ile Pro Ile Ile Ala Arg Leu Gln Gly Thr Asn Met Glu Gln Ala His
385                 390                 395                 400

Gln Leu Ile Asn Asp Ser Gly Met Lys Ile Phe Ser Ile Asp Asp Leu
            405                 410                 415

Gln Ser Ala Ala Glu Arg Ala Val Gln Leu Ser Lys Val Val Lys Met
            420                 425                 430

Ala Arg Asp Ile Asp Val Gly Val Glu Phe Thr Leu Gly Ile
            435                 440                 445

<210> SEQ ID NO 3
<211> LENGTH: 1564
<212> TYPE: DNA
<213> ORGANISM: Myceliophthora thermophila

<400> SEQUENCE: 3
atggcgccga cgtcaacaac gagcttcccc gctgaggtcg tacctcaggc ccccgaggac      60
cccctcttcg gtctgatgcg ggcttacagg gctgattcca gtccaaacaa ggttgatctg     120
gtacgccgaa acccccttte ctctctaggg gctgtctctg tttgcaagcc ggctcgcaga     180
taagcttagg caggctaaca cgccccgtcc cccagggaat ggcgcgtat cgtgacgata      240 acgcaaaacc ctggattcta ccagtggtca agaaggtgcg cgcattttt cgaggctgac     300 ggaatcccaa cttcccaatt ccgaaacgcc gtctgccacc ggttccggcg gcttgggacg     360
cgtcttggac agcagccacg ctgcctgccc ctcgatcaat ttacccgccg ccaatccccc     420
caattgcccc tccccgcac accccctgcc gagcagcgag ctgacagttt cccggcgta      480 ctaggccgat gagattttac gcaacgatcc ggaagccaac cacgagtacc ttccgatcgc     540
cggcctcgca tcgctaacaa gcaaagccgc cgaactcctg ctcggtcagt ccgcaccggc     600
```

```
catcgccgag aagcgcaccg cgtcggttca aaccatctct ggcaccggtg ccgtccacct    660
gggcgctctc ttcctcgcca aattctacaa agttcagggc gccaaccgca ccgtctacgt    720
cagtaacccg acctgggcga accaccacca gatcttcacg aatgtcggcc tgcccatcgc    780
cacttatccg tacttcaaca agaacaccaa ggggctagat atcgatggca tgaaggcggc    840
gcttgagcag gcccctgatg ggagcataat cctcctacat gcctgcgcgc acaacccgac    900
cggcgtcgac cctaccccctg agcagtggcg cgagattgcc ctgctgatga aggccaagag    960
acacttcccc ttcttcgaca cggcttacca gggcttcgct tcgggagacc tagaccggga   1020
cgccagcgcc atcaggctgt tgtcgagga gggcttcgag ctggtgattg cccagtcttt   1080
tgccaaaaac ttcggcctct acggcgagcg cgccggttgc ttccactacg tggcttcccc   1140
ctctgccgat gccgccagtg tcacgacgcg cgtggcctcg cagctggcca ttctgcagcg   1200
ctcggagatc agcaaccccc ccatctacgg cgcccgcatc gcctctatcg ttctgaacga   1260
cccggcgctg tttgccgagt ggcaggagaa cctccgcacc atgtcgggcc gcattattga   1320
catgcggaag agactccggg ccaagctcga ggaactcggc actcctggcc agtggaacca   1380
tatcacggac cagatcggaa tgttcagctt cacggggctt accgagcctc aggtgctcaa   1440
gctgcggtcc gactaccaca tttacatgac caaaaacggg cgcatcagca tggctggtct   1500
gaactcgaaa aatgtcgact acgtcgcaac ggctatagat aaagtggttc gggaggtgca   1560
atga                                                               1564

<210> SEQ ID NO 4
<211> LENGTH: 419
<212> TYPE: PRT
<213> ORGANISM: Myceliophthora thermophila

<400> SEQUENCE: 4

Met Ala Pro Thr Ser Thr Thr Ser Phe Pro Ala Glu Val Val Pro Gln
1               5                   10                  15

Ala Pro Glu Asp Pro Leu Phe Gly Leu Met Arg Ala Tyr Arg Ala Asp
            20                  25                  30

Ser Ser Pro Asn Lys Val Asp Leu Gly Ile Gly Ala Tyr Arg Asp Asp
        35                  40                  45

Asn Ala Lys Pro Trp Ile Leu Pro Val Val Lys Ala Asp Glu Ile
    50                  55                  60

Leu Arg Asn Asp Pro Glu Ala Asn His Glu Tyr Leu Pro Ile Ala Gly
65                  70                  75                  80

Leu Ala Ser Leu Thr Ser Lys Ala Ala Glu Leu Leu Gly Gln Ser
                85                  90                  95

Ala Pro Ala Ile Ala Glu Lys Arg Thr Ala Ser Val Gln Thr Ile Ser
            100                 105                 110

Gly Thr Gly Ala Val His Leu Gly Ala Leu Phe Leu Ala Lys Phe Tyr
        115                 120                 125

Lys Val Gln Gly Ala Asn Arg Thr Val Tyr Val Ser Asn Pro Thr Trp
    130                 135                 140

Ala Asn His His Gln Ile Phe Thr Asn Val Gly Leu Pro Ile Ala Thr
145                 150                 155                 160

Tyr Pro Tyr Phe Asn Lys Asn Thr Lys Gly Leu Asp Ile Asp Gly Met
                165                 170                 175

Lys Ala Ala Leu Glu Gln Ala Pro Asp Gly Ser Ile Ile Leu Leu His
            180                 185                 190

Ala Cys Ala His Asn Pro Thr Gly Val Asp Pro Thr Pro Glu Gln Trp
```

```
                195                 200                 205
Arg Glu Ile Ala Leu Leu Met Lys Ala Lys Arg His Phe Pro Phe Phe
    210                 215                 220

Asp Thr Ala Tyr Gln Gly Phe Ala Ser Gly Asp Leu Asp Arg Asp Ala
225                 230                 235                 240

Ser Ala Ile Arg Leu Phe Val Glu Glu Gly Phe Glu Leu Val Ile Ala
                245                 250                 255

Gln Ser Phe Ala Lys Asn Phe Gly Leu Tyr Gly Glu Arg Ala Gly Cys
            260                 265                 270

Phe His Tyr Val Ala Ser Pro Ser Ala Asp Ala Ala Ser Val Thr Thr
        275                 280                 285

Arg Val Ala Ser Gln Leu Ala Ile Leu Gln Arg Ser Glu Ile Ser Asn
    290                 295                 300

Pro Pro Ile Tyr Gly Ala Arg Ile Ala Ser Ile Val Leu Asn Asp Pro
305                 310                 315                 320

Ala Leu Phe Ala Glu Trp Gln Glu Asn Leu Arg Thr Met Ser Gly Arg
                325                 330                 335

Ile Ile Asp Met Arg Lys Arg Leu Arg Ala Lys Leu Glu Glu Leu Gly
            340                 345                 350

Thr Pro Gly Gln Trp Asn His Ile Thr Asp Gln Ile Gly Met Phe Ser
        355                 360                 365

Phe Thr Gly Leu Thr Glu Pro Gln Val Leu Lys Leu Arg Ser Asp Tyr
    370                 375                 380

His Ile Tyr Met Thr Lys Asn Gly Arg Ile Ser Met Ala Gly Leu Asn
385                 390                 395                 400

Ser Lys Asn Val Asp Tyr Val Ala Thr Ala Ile Asp Lys Val Val Arg
                405                 410                 415

Glu Val Gln

<210> SEQ ID NO 5
<211> LENGTH: 2242
<212> TYPE: DNA
<213> ORGANISM: Myceliophthora thermophila

<400> SEQUENCE: 5
atgtccaagg ccgcaactgt caaggaggcc gtgaaggaga cgctcgtcgg ctcgaaagag    60
cccgagaagt tttcggcgca gacaaggggcg cgcttcaacc gccatgctgt gaaggacccc   120
gagaccggag aattgtatct cggcccggag caattcatcg acgctattgc cccgccgcat   180
gaagactacg tgagtccctt gcgctcagtt gctggccaaa cctaaggcgc acgtcgctta   240
taccaatccg catgtagcac aagatcaagc gggaacaata ctcgatcctg ttccatgttg   300
ccgaccgaac aaacaagggc aggctgtcgc tcgccgacta cgggtacttc gagaacctcc   360
tcagcaagcc cgatgccgaa tatgagatcg cgttccgcct ctttgacgtc gagcgcctgg   420
gcaccgtgaa gtacgaagac ttccggcggc tttacgaact gaacaaggga cccgacagca   480
tcccgttcga ctgggactgc gagtgggcaa aactgtacat cggcagcaag tcgaacaggc   540
acagcttgaa ctaccagcaa ttctcacaga tgctccgcgg cttgcagggc gagcgcgttc   600
gacaagcttt ccagcgcttc gacacggacg gcgacgggtt cattgagccg aaagagtttg   660
cgactatcat ccagcagacg gccaggcata gctgtcggac ccacctgctc gagaacctgc   720
acacgctgtg caacatttcc cagggcagca aggtgtcgta cgccaatgtc cgagcgttcc   780
tgaacatgat caatgagatg gatctggtcg agctcatcgt ccggcgcgcc tgctccaaca   840
```

-continued

```
gcaaggacgg ccgcatcacg agaaccgagt tcctcaacca ggctgctaaa atcacccgct      900
tctccctctt caccccgatg gaggccgata tcctgttcca ctttgccagc ctggatgagc      960
cgtcgggaag actgggactc aaggacttca ccaaggtgtt ggatgcagcg tggcggcggc     1020
gcgacgagga ggacgacggc cgcgtcgttc ctgaggctcg gtccactggt cagaatgtct     1080
tggcgcagac catggagtcg gcgtacaact cgctctcgg cagtctggct ggtgctttcg      1140
gtgccttcat ggtgtacccg atcgatttgg tcaagactcg gatgcagaac cagcgcggtg     1200
ccgatccggg ccagcgcctg tacaagaact cgatcgactg cttcaagaag gtggtccgca     1260
acgaaggttt cagaggcctg tattcgggtg tcctccccca gcttgtcggt gtcgcgccag     1320
agaaagccat caagcttacc gtgaacgacc ttgtccgcgg gtggttcacc gataagcagg     1380
gcaagatcca ctgggcgcc gaggtgctcg ctggtggcgc cgccggtggt tgccaagtgg      1440
tatgtcattc ccgactttga gcccgtacgc catgagggga aaacaaaaga cgctgacgtg     1500
gactgtgctg caggtgttca ccaacccct cgaaattgtc aagattcgcc tccaggtgca      1560
gggagaggtg gccaagagtg tggagggcgc gccgaagcgg tcggccatgt ggatcgtgcg     1620
caacctcggc ctggtcggcc tttacaaggg cgcgtcggca tgtctgctcc gagatgtgcc     1680
gttttcggcc atctacttcc cgacctactc ccacctgaag cgggacgtct ttggggagtc     1740
gtcgaccaag aagctcggcg tcctccagct cctcacggct ggtgccattg ccggcatgcc     1800
cgcggcatac ctgaccacgc cgtgcgacgt catcaagacc cgtcttcaag tcgaagcgcg     1860
taagggcgac accacctata cgggactgcg gcacgcggcc aagacgatct ggaaggagga     1920
gggcttccgt gccttcttca agggcgggcc cgctcgtatc ttccgttcgt cgccgcagtt     1980
cggcttcacg ctggccgcct atgagctgct gcagagcgtg ctcccgttcc cgggcaagca     2040
gtccgaggcc aaggtggcag cgggcgtcgc ggaggcgatg tcgaatctca ggaaaaaggc     2100
cgtcgacagc ccgttctacc ggtcccgcaa cgctctcaag atcctgctcg acttggacga     2160
gcactttggc cgcacaccgc tggggcccaa ttcacgcggc tggaaatcgc tgccggggtg     2220
gatgaacgca aagacggcgt ag                                              2242
```

<210> SEQ ID NO 6
<211> LENGTH: 699
<212> TYPE: PRT
<213> ORGANISM: Myceliophthora thermophila

<400> SEQUENCE: 6

Met Ser Lys Ala Ala Thr Val Lys Glu Ala Val Lys Glu Thr Leu Val
1               5                   10                  15

Gly Ser Lys Glu Pro Glu Lys Phe Ser Ala Gln Thr Arg Ala Arg Phe
            20                  25                  30

Asn Arg His Ala Val Lys Asp Pro Glu Thr Gly Glu Leu Tyr Leu Gly
        35                  40                  45

Pro Glu Gln Phe Ile Asp Ala Ile Ala Pro His Glu Asp Tyr His
    50                  55                  60

Lys Ile Lys Arg Glu Gln Tyr Ser Ile Leu Phe His Val Ala Asp Arg
65                  70                  75                  80

Thr Asn Lys Gly Arg Leu Ser Leu Ala Asp Tyr Gly Tyr Phe Glu Asn
                85                  90                  95

Leu Leu Ser Lys Pro Asp Ala Glu Tyr Glu Ile Ala Phe Arg Leu Phe
            100                 105                 110

Asp Val Glu Arg Leu Gly Thr Val Lys Tyr Glu Asp Phe Arg Arg Leu
        115                 120                 125

-continued

Tyr Glu Leu Asn Lys Gly Pro Asp Ser Ile Pro Phe Asp Trp Asp Cys
    130                 135                 140

Glu Trp Ala Lys Leu Tyr Ile Gly Ser Lys Ser Asn Arg His Ser Leu
145                 150                 155                 160

Asn Tyr Gln Gln Phe Ser Gln Met Leu Arg Gly Leu Gln Gly Glu Arg
                165                 170                 175

Val Arg Gln Ala Phe Gln Arg Phe Asp Thr Asp Gly Asp Gly Phe Ile
            180                 185                 190

Glu Pro Glu Glu Phe Ala Thr Ile Ile Gln Gln Thr Ala Arg His Lys
        195                 200                 205

Leu Ser Asp His Leu Leu Glu Asn Leu His Thr Leu Cys Asn Ile Ser
    210                 215                 220

Gln Gly Ser Lys Val Ser Tyr Ala Asn Val Arg Ala Phe Leu Asn Met
225                 230                 235                 240

Ile Asn Glu Met Asp Leu Val Glu Leu Ile Val Arg Arg Ala Cys Ser
                245                 250                 255

Asn Ser Lys Asp Gly Arg Ile Thr Arg Thr Glu Phe Leu Asn Gln Ala
            260                 265                 270

Ala Lys Ile Thr Arg Phe Ser Leu Phe Thr Pro Met Glu Ala Asp Ile
        275                 280                 285

Leu Phe His Phe Ala Ser Leu Asp Glu Pro Ser Gly Arg Leu Gly Leu
    290                 295                 300

Lys Asp Phe Thr Lys Val Leu Asp Ala Ala Trp Arg Arg Asp Glu
305                 310                 315                 320

Glu Asp Asp Gly Arg Val Val Pro Glu Ala Arg Ser Thr Gly Gln Asn
                325                 330                 335

Val Leu Ala Gln Thr Met Glu Ser Ala Tyr Asn Phe Ala Leu Gly Ser
            340                 345                 350

Leu Ala Gly Ala Phe Gly Ala Phe Met Val Tyr Pro Ile Asp Leu Val
        355                 360                 365

Lys Thr Arg Met Gln Asn Gln Arg Gly Ala Asp Pro Gly Gln Arg Leu
    370                 375                 380

Tyr Lys Asn Ser Ile Asp Cys Phe Lys Lys Val Val Arg Asn Glu Gly
385                 390                 395                 400

Phe Arg Gly Leu Tyr Ser Gly Val Leu Pro Gln Leu Val Gly Val Ala
                405                 410                 415

Pro Glu Lys Ala Ile Lys Leu Thr Val Asn Asp Leu Val Arg Gly Trp
            420                 425                 430

Phe Thr Asp Lys Gln Gly Lys Ile His Trp Gly Ala Glu Val Leu Ala
        435                 440                 445

Gly Gly Ala Ala Gly Gly Cys Gln Val Val Phe Thr Asn Pro Leu Glu
    450                 455                 460

Ile Val Lys Ile Arg Leu Gln Val Gln Gly Glu Val Ala Lys Ser Val
465                 470                 475                 480

Glu Gly Ala Pro Lys Arg Ser Ala Met Trp Ile Val Arg Asn Leu Gly
                485                 490                 495

Leu Val Gly Leu Tyr Lys Gly Ala Ser Ala Cys Leu Leu Arg Asp Val
            500                 505                 510

Pro Phe Ser Ala Ile Tyr Phe Pro Thr Tyr Ser His Leu Lys Arg Asp
        515                 520                 525

Val Phe Gly Glu Ser Ser Thr Lys Lys Leu Gly Val Leu Gln Leu Leu
    530                 535                 540

```
Thr Ala Gly Ala Ile Ala Gly Met Pro Ala Ala Tyr Leu Thr Thr Pro
545                 550                 555                 560

Cys Asp Val Ile Lys Thr Arg Leu Gln Val Glu Ala Arg Lys Gly Asp
                565                 570                 575

Thr Thr Tyr Thr Gly Leu Arg His Ala Ala Lys Thr Ile Trp Lys Glu
            580                 585                 590

Glu Gly Phe Arg Ala Phe Phe Lys Gly Gly Pro Ala Arg Ile Phe Arg
        595                 600                 605

Ser Ser Pro Gln Phe Gly Phe Thr Leu Ala Ala Tyr Glu Leu Leu Gln
    610                 615                 620

Ser Val Leu Pro Phe Pro Gly Lys Gln Ser Glu Ala Lys Val Ala Ala
625                 630                 635                 640

Gly Val Ala Glu Ala Met Ser Asn Leu Lys Glu Lys Ala Val Asp Ser
                645                 650                 655

Pro Phe Tyr Arg Ser Arg Asn Ala Leu Lys Ile Leu Leu Asp Leu Asp
            660                 665                 670

Glu His Phe Gly Arg Thr Pro Leu Gly Pro Asn Ser Arg Gly Trp Lys
        675                 680                 685

Ser Leu Pro Gly Trp Met Asn Ala Lys Thr Ala
    690                 695
```

<210> SEQ ID NO 7
<211> LENGTH: 849
<212> TYPE: DNA
<213> ORGANISM: Myceliophthora thermophila

<400> SEQUENCE: 7

```
atggcgtcag caaaggagaa ggcgccgctg ccgttccgct atacgttcat ggccggcgcc     60
attgccggtg tatctgaaat cctggtcatg tacccgctgg atgtcgtgaa acaagagta    120
cagctgcaga ccggtaaagg ctccggtgcc gatgcgtaca gtggcatgct cgactgcttc    180
cagaagatca tccgcaacga aggcttctcg aggctctacc gcggcattac cgctcccatt    240
ctcatggagg cgcccaagcg cgcgaccaag ttcgcggcca cgacaaatg gggcaaattc     300
tacaaggatc tctttggcca gcagaccatg acacagtcgc tctcggtcct gactggtgct    360
tcggccggcg cgactgagtc cttcgtcgtg gtgcccttcg agctcgtcaa gatccgcctc    420
caggacaagg cctcggccgg caagtacagc ggtatgattg atgttgtcgt caagacggtg    480
cgcaacgaag gtctgctggc catgtacaac ggcctcgagt ctactctctg gcgccacatt    540
ctctggaact cgggctactt cggctgcatc ttccaggttc ggcaattgct ccccaaggcg    600
gagacgaagt cgggacaaac aatcaacgac atcgtcgccg gtaccattgg cggcactgtc    660
ggcacgattc tgaataccc catggatgtc gtgaagagcc gtatccagaa cagcgtcaag    720
gttgccggcc aaacacccaa gtacaactgg gcctggcctg ccgtggcgac ggttgccaaa    780
gaggaaggct cgggggccct ctacaaaggc ttcatcccca aggttctccg gctgggacct    840
ggcggcggc                                                            849
```

<210> SEQ ID NO 8
<211> LENGTH: 304
<212> TYPE: PRT
<213> ORGANISM: Myceliophthora thermophila

<400> SEQUENCE: 8

```
Met Ala Ser Ala Lys Glu Lys Ala Pro Leu Pro Phe Arg Tyr Thr Phe
1               5                   10                  15
```

```
Met Ala Gly Ala Ile Ala Gly Val Ser Glu Ile Leu Val Met Tyr Pro
             20                  25                  30
Leu Asp Val Val Lys Thr Arg Val Gln Leu Gln Thr Gly Lys Gly Ser
         35                  40                  45
Gly Ala Asp Ala Tyr Ser Gly Met Leu Asp Cys Phe Gln Lys Ile Ile
     50                  55                  60
Arg Asn Glu Gly Phe Ser Arg Leu Tyr Arg Gly Ile Thr Ala Pro Ile
 65                  70                  75                  80
Leu Met Glu Ala Pro Lys Arg Ala Thr Lys Phe Ala Ala Asn Asp Lys
                 85                  90                  95
Trp Gly Lys Phe Tyr Lys Asp Leu Phe Gly Gln Gln Thr Met Thr Gln
            100                 105                 110
Ser Leu Ser Val Leu Thr Gly Ala Ser Ala Gly Ala Thr Glu Ser Phe
        115                 120                 125
Val Val Val Pro Phe Glu Leu Val Lys Ile Arg Leu Gln Asp Lys Ala
    130                 135                 140
Ser Ala Gly Lys Tyr Ser Gly Met Ile Asp Val Val Lys Thr Val
145                 150                 155                 160
Arg Asn Glu Gly Leu Leu Ala Met Tyr Asn Gly Leu Glu Ser Thr Leu
                165                 170                 175
Trp Arg His Ile Leu Trp Asn Ser Gly Tyr Phe Gly Cys Ile Phe Gln
            180                 185                 190
Val Arg Gln Leu Leu Pro Lys Ala Glu Thr Lys Ser Gly Gln Thr Ile
        195                 200                 205
Asn Asp Ile Val Ala Gly Thr Ile Gly Gly Thr Val Gly Thr Ile Leu
    210                 215                 220
Asn Thr Pro Met Asp Val Val Lys Ser Arg Ile Gln Asn Ser Val Lys
225                 230                 235                 240
Val Ala Gly Gln Thr Pro Lys Tyr Asn Trp Ala Trp Pro Ala Val Ala
                245                 250                 255
Thr Val Ala Lys Glu Glu Gly Phe Gly Ala Leu Tyr Lys Gly Phe Ile
            260                 265                 270
Pro Lys Val Leu Arg Leu Gly Pro Gly Gly Ile Leu Leu Val Val
        275                 280                 285
Tyr Thr Gly Val Met Asp Phe Phe Arg Lys Ile Arg Asp Gly Glu Ala
    290                 295                 300

<210> SEQ ID NO 9
<211> LENGTH: 993
<212> TYPE: DNA
<213> ORGANISM: Myceliophthora thermophila

<400> SEQUENCE: 9
atggtcaaag ctgtcgttgc tggcgcctcc ggcggtattg acagccgct gtcgctgctc      60 ctgaagctct ctccgctcgt cagcgagctc gcactctacg atgttgtcaa cacccccggt    120
gttgcgaccg acctgtcgca catttcatcc aacgccaaaa ccactggcta cctgcccgcc    180
aacgacggcg ccaagaccgc tttcaaggat gccgacatca tcatcatccc ggcgggcatt    240
ccccgcaagc ccggcatgac ccgtgatgac ctcttcaaca tcaacgccgg catcgtgaag    300
ggcctcattg aggtggccgc cgaggtcgcc ccaaggcct tcatcctggt tatttccaac     360
cccgtcaact cgaccgtccc catctcggcc gaggtgctca aggccaaggg cgtcttcaac    420
ccccagcgcc tcttcggtgt caccaccctc gacattgtcc gtgccgagac cttcgttgcc    480
gagattgccg gcaagagcaa ccccaggag ttgactgtcc ccgtcgttgg cggtcactcc     540
```

-continued

```
ggcgagacca ttgttccgct tttcagcaag atcgctccgt ctgtcacgat tccggacgac    600
aagtacgacg ctcttgtcaa ccgcgtccag ttcggtggtg atgaggttgt caaggccaag    660
gacggcgctg ttctgccac actttcgatg gcgtatgctg gttacaggtt cgccgagaag    720
ctcctcaagg ccgccgcggg cgtcaagggc ctcgttgaac caagctacgt ctaccttccc    780
ggcatcccag gtggcaagga gattgccgag aagaccggtg tcgagttctt ctccgttccc    840
atcgagcttg ccctaatgg cgccgagaag gcggtcgata tcctcggcga catcaccgac    900
aaggagaaga agttgctcga ggcggcagtg tcgggcctga agcggaacat caagaagggc    960
atcgacttcg cccacaaccc cccccagaag tga                               993
```

<210> SEQ ID NO 10
<211> LENGTH: 330
<212> TYPE: PRT
<213> ORGANISM: Myceliophthora thermophila

<400> SEQUENCE: 10

```
Met Val Lys Ala Val Ala Gly Ala Ser Gly Gly Ile Gly Gln Pro
  1               5                  10                  15

Leu Ser Leu Leu Lys Leu Ser Pro Leu Val Ser Glu Leu Ala Leu
                 20                  25                  30

Tyr Asp Val Val Asn Thr Pro Gly Val Ala Thr Asp Leu Ser His Ile
             35                  40                  45

Ser Ser Asn Ala Lys Thr Thr Gly Tyr Leu Pro Ala Asn Asp Gly Ala
         50                  55                  60

Lys Thr Ala Phe Lys Asp Ala Asp Ile Ile Ile Pro Ala Gly Ile
 65                  70                  75                  80

Pro Arg Lys Pro Gly Met Thr Arg Asp Asp Leu Phe Asn Ile Asn Ala
                 85                  90                  95

Gly Ile Val Lys Gly Leu Ile Glu Val Ala Ala Glu Val Ala Pro Lys
            100                 105                 110

Ala Phe Ile Leu Val Ile Ser Asn Pro Val Asn Ser Thr Val Pro Ile
        115                 120                 125

Ser Ala Glu Val Leu Lys Ala Lys Gly Val Phe Asn Pro Gln Arg Leu
    130                 135                 140

Phe Gly Val Thr Thr Leu Asp Ile Val Arg Ala Glu Thr Phe Val Ala
145                 150                 155                 160

Glu Ile Ala Gly Lys Ser Asn Pro Gln Glu Leu Thr Val Pro Val Val
                165                 170                 175

Gly Gly His Ser Gly Glu Thr Ile Val Pro Leu Phe Ser Lys Ile Ala
            180                 185                 190

Pro Ser Val Thr Ile Pro Asp Asp Lys Tyr Asp Ala Leu Val Asn Arg
        195                 200                 205

Val Gln Phe Gly Gly Asp Glu Val Val Lys Ala Lys Asp Gly Ala Gly
    210                 215                 220

Ser Ala Thr Leu Ser Met Ala Tyr Ala Gly Tyr Arg Phe Ala Glu Lys
225                 230                 235                 240

Leu Leu Lys Ala Ala Ala Gly Val Lys Gly Leu Val Glu Pro Ser Tyr
                245                 250                 255

Val Tyr Leu Pro Gly Ile Pro Gly Gly Lys Glu Ile Ala Glu Lys Thr
            260                 265                 270

Gly Val Glu Phe Phe Ser Val Pro Ile Glu Leu Gly Pro Asn Gly Ala
        275                 280                 285
```

```
Glu Lys Ala Val Asp Ile Leu Gly Asp Ile Thr Asp Lys Glu Lys Lys
        290                 295                 300

Leu Leu Glu Ala Ala Val Ser Gly Leu Lys Arg Asn Ile Lys Lys Gly
305                 310                 315                 320

Ile Asp Phe Ala His Asn Pro Pro Gln Lys
                325                 330

<210> SEQ ID NO 11
<211> LENGTH: 1143
<212> TYPE: DNA
<213> ORGANISM: Aspergillus oryzae

<400> SEQUENCE: 11
atgctgacac ctcccaagtt tgaggatgag aagcagctgg gccccgtggg tatccgggag      60
aggcttcgcc atttcacttg ggcctggtac acattaacga tgagtggagg agggctggcc     120
gtcctcatca tcagccagcc ctttgggttc gcggattga gagagatcgg catcgctgtc      180
tatatcctca acctgatcct cttcgcccct gtctgctcta ccatggctat aaggttcatc     240
ctgcacggca accttctgga gtccctccgt catgaccgcg agggtctctt cttcccgacc     300
ttctggctct ccgtcgcaac catcatctgc ggcttgtctc gctacttcgg tgaagaatcg     360
aatgagtcct tccaactagc cctcgaagcc ctcttctgga tctactgcgt ctgcacctta     420
ctcgtcgcaa tcatccaata ctcgttcgtc ttctcatccc acaagtacgg ccttcaaacc     480
atgatgcctt catggatcct tccagccttc cccatcatgc tcagcggcac catcgcctcc     540
gtcatcggtg aacaacaacc cgctcgcgca gccctcccca tcatcggcgc cggcgtcacc     600
ttccagggcc tcggcttctc catcagcttc atgatgtacg cccactacat cggccgactg     660
atggagtccg gcctccccca cagcgaccac agaccaggca tgttcatctg cgtcggaccc     720
cccgccttca cagccctcgc cctcgtcggc atgagcaaag gcctccccga agacttcaag     780
ctgctccacg acgcccacgc cctggaagat ggccgcatca tcgagctgct ggccatctcc     840
gccggcgtct tcctctgggc cctgagtctc tggttcttct gcatcgccat gtcgccgtc      900 atccgctcgc cccccgaggc cttccacctc aactggtggg ccatggtctt ccccaacacc     960
ggcttcaccc tggccaccat caccctgggc aaggctctca cagtaacggg tgtgaagggc    1020
gtcggttccg ccatgtctat ctgcatcgtg tgcatgtata tcttcgtctt cgtcaacaat    1080
gtccgcgccg ttatccggaa ggatatcatg tacccgggta agatgagga tgtatctgat    1140 tag                                                                 1143

<210> SEQ ID NO 12
<211> LENGTH: 380
<212> TYPE: PRT
<213> ORGANISM: Aspergillus oryzae

<400> SEQUENCE: 12

Met Leu Thr Pro Pro Lys Phe Glu Asp Glu Lys Gln Leu Gly Pro Val
 1               5                  10                  15

Gly Ile Arg Glu Arg Leu Arg His Phe Thr Trp Ala Trp Tyr Thr Leu
            20                  25                  30

Thr Met Ser Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80
```

Leu His Gly Asn Leu Leu Glu Ser Leu Arg His Asp Arg Glu Gly Leu
                85                  90                  95
Phe Phe Pro Thr Phe Trp Leu Ser Val Ala Thr Ile Ile Cys Gly Leu
            100                 105                 110
Ser Arg Tyr Phe Gly Glu Glu Ser Asn Glu Ser Phe Gln Leu Ala Leu
        115                 120                 125
Glu Ala Leu Phe Trp Ile Tyr Cys Val Cys Thr Leu Leu Val Ala Ile
    130                 135                 140
Ile Gln Tyr Ser Phe Val Phe Ser Ser His Lys Tyr Gly Leu Gln Thr
145                 150                 155                 160
Met Met Pro Ser Trp Ile Leu Pro Ala Phe Pro Ile Met Leu Ser Gly
                165                 170                 175
Thr Ile Ala Ser Val Ile Gly Glu Gln Gln Pro Ala Arg Ala Ala Leu
            180                 185                 190
Pro Ile Ile Gly Ala Gly Val Thr Phe Gln Gly Leu Gly Phe Ser Ile
        195                 200                 205
Ser Phe Met Met Tyr Ala His Tyr Ile Gly Arg Leu Met Glu Ser Gly
    210                 215                 220
Leu Pro His Ser Asp His Arg Pro Gly Met Phe Ile Cys Val Gly Pro
225                 230                 235                 240
Pro Ala Phe Thr Ala Leu Ala Leu Val Gly Met Ser Lys Gly Leu Pro
                245                 250                 255
Glu Asp Phe Lys Leu Leu His Asp Ala His Ala Leu Glu Asp Gly Arg
            260                 265                 270
Ile Ile Glu Leu Leu Ala Ile Ser Ala Gly Val Phe Leu Trp Ala Leu
        275                 280                 285
Ser Leu Trp Phe Phe Cys Ile Ala Ile Val Ala Ile Arg Ser Pro
    290                 295                 300
Pro Glu Ala Phe His Leu Asn Trp Trp Ala Met Val Phe Pro Asn Thr
305                 310                 315                 320
Gly Phe Thr Leu Ala Thr Ile Thr Leu Gly Lys Ala Leu Asn Ser Asn
                325                 330                 335
Gly Val Lys Gly Val Gly Ser Ala Met Ser Ile Cys Ile Val Cys Met
            340                 345                 350
Tyr Ile Phe Val Phe Val Asn Asn Val Arg Ala Val Ile Arg Lys Asp
        355                 360                 365
Ile Met Tyr Pro Gly Lys Asp Glu Asp Val Ser Asp
    370                 375                 380

<210> SEQ ID NO 13
<211> LENGTH: 1760
<212> TYPE: DNA
<213> ORGANISM: Neurospora crassa

<400> SEQUENCE: 13
atgggcagcc agcctcccat gccgcctcct gtgcagacgg gaacgcacgt catcatccat     60
gacaccacat acaaccagaa ccaacagtcg ccaacacaac atcaacaaca aaacaggctc    120
aacccagtcg acacctcctt tctcggctcc cactcccggc agtcctcctc cgcaaccgta    180
accggtgacg attctgaccc atcccgcgcc ttcggcacct acgccgggac accaaagggt    240
gagtatgaga agaagggccg ctcaaccgat tacctctccg gccccaccgg cgacaactcc    300
ctcaacacct cggccgcctc ctcccggtta gccctcaact ccaacaacga gaagtccaac    360
cacgatggcc acatgtccgg cggcgccggc caccaccacc gccgctccgc ctcccctct    420

```
tcctcctcct ccgattccga ctccgacctg gaaggtgccg gcggccacat gcagaaaggc    480
catcacaaca tagacccccta cgatccttcc cgcccaaagc taccactcaa agcgcggcta    540
aaacacttca cctgggcctg gtacaccctc tgcatgtcca ccggcggtct ctccctcttg    600
atcgccgcgc aaccacacac cttccccggc ctgcgccaga tcggcatgac cgtatacatc    660
atcaacatca tcatcttcgt cctcctgacc tccctccaaa tcacccgctt catgctccac    720
gccggctcct tcaaagccag cctcacgcac ccgcgcgaag gcttcttctt ccccaccttc    780
ttcctcagca tcgccactct aatcacctcg acccaaaagt acggcacccc tcccgacagc    840
gaacccagcc aggacctcgt ctgggttttg cacattgcct tctggatcta cctcatcctc    900
gccaccgccg tcgccatcgg gcaatactcc ttcctcttca gccaaaaacg ctccttctcc    960
ctagccacca tgatgcccac ctggatcctg cccatcttcc ccatcatgct ctcgggcacc   1020
atcgcggccg tcatctcccc cttccagccc ccgcaccgcg ccatcgtcgt catctgcgcc   1080
ggcctcacct gccagggcct cggcgccgcc gtggcgttca tgatgtacgc acacatggtc   1140
ggccgtctca tgtccgtcgg tcttcccgac cgcgaacacc gtcccggcct gttcatgtgc   1200
gttggcccgc cgtccttcac tgctttggca ttcatcggca tggcgcaggg cttgccgcgg   1260
gactttgatc acgacatgga cgggttcatc gacgcaggca tgattcgcac catggctgtc   1320
attggcgccg tgtttctctg ggcgttagcg ttctggtggt tctttattgg tgtgttggct   1380
gtgttggcga gcagacccaa gtatttccat ttgggatggt gggccagtgt tttccccaac   1440
acgggattca cgttggcgac gattagtatt ggaaatgcct ttcaaagcga tgcggtgctg   1500
tgggtgggca cgggcatgag tttgtgtttg ttggggacgt atttgtttgt gttgggcaac   1560
catgtgcggg cggtggtggt gcaggatatt tgttatccgg ggagggatga ggatgtggag   1620
gatcattagt gtgggtgggc acgggcatga gtttgtgttt gttggggacg tatttgtttg   1680
tgttgggcaa ccatgtgcgg gcggtggtgg tgcaggatat ttgttatccg gggagggatg   1740
aggatgtgga ggatcattag                                                1760
```

<210> SEQ ID NO 14
<211> LENGTH: 542
<212> TYPE: PRT
<213> ORGANISM: Neurospora crassa

<400> SEQUENCE: 14

```
Met Gly Ser Gln Pro Pro Met Pro Pro Val Gln Thr Gly Thr His
1               5                  10                  15

Val Ile Ile His Asp Thr Thr Tyr Asn Gln Asn Gln Ser Pro Thr
            20                  25                  30

Gln His Gln Gln Gln Asn Arg Leu Asn Pro Val Asp Thr Ser Phe Leu
        35                  40                  45

Gly Ser His Ser Arg Gln Ser Ser Ala Thr Val Thr Gly Asp Asp
    50                  55                  60

Ser Asp Pro Ser Arg Ala Phe Gly Thr Tyr Ala Gly Thr Pro Lys Gly
65                  70                  75                  80

Glu Tyr Glu Lys Lys Gly Arg Ser Thr Asp Tyr Leu Ser Gly Pro Thr
                85                  90                  95

Gly Asp Asn Ser Leu Asn Thr Ser Ala Ala Ser Ser Arg Leu Ala Leu
            100                 105                 110

Asn Ser Asn Asn Glu Lys Ser Asn His Asp Gly His Met Ser Gly Gly
        115                 120                 125
```

```
Ala Gly His His His Arg Arg Ser Ala Ser Pro Ser Ser Ser Ser
    130                 135                 140

Asp Ser Asp Ser Asp Leu Glu Gly Ala Gly His Met Gln Lys Gly
145                 150                 155                 160

His His Asn Ile Asp Pro Tyr Asp Pro Ser Arg Pro Lys Leu Pro Leu
                165                 170                 175

Lys Ala Arg Leu Lys His Phe Thr Trp Ala Trp Tyr Thr Leu Cys Met
            180                 185                 190

Ser Thr Gly Gly Leu Ser Leu Leu Ile Ala Ala Gln Pro His Thr Phe
        195                 200                 205

Pro Gly Leu Arg Gln Ile Gly Met Thr Val Tyr Ile Ile Asn Ile Ile
210                 215                 220

Ile Phe Val Leu Leu Thr Ser Leu Gln Ile Thr Arg Phe Met Leu His
225                 230                 235                 240

Ala Gly Ser Phe Lys Ala Ser Leu Thr His Pro Arg Glu Gly Phe Phe
                245                 250                 255

Phe Pro Thr Phe Phe Leu Ser Ile Ala Thr Leu Ile Thr Ser Thr Gln
            260                 265                 270

Lys Tyr Gly Thr Pro Pro Asp Ser Glu Pro Ser Gln Asp Leu Val Trp
        275                 280                 285

Val Leu His Ile Ala Phe Trp Ile Tyr Leu Ile Leu Ala Thr Ala Val
290                 295                 300

Ala Ile Gly Gln Tyr Ser Phe Leu Phe Ser Gln Lys Arg Ser Phe Ser
305                 310                 315                 320

Leu Ala Thr Met Met Pro Thr Trp Ile Leu Pro Ile Phe Pro Ile Met
                325                 330                 335

Leu Ser Gly Thr Ile Ala Ala Val Ile Ser Pro Phe Gln Pro Pro His
            340                 345                 350

Arg Ala Ile Val Val Ile Cys Ala Gly Leu Thr Cys Gln Gly Leu Gly
        355                 360                 365

Ala Ala Val Ala Phe Met Met Tyr Ala His Met Val Gly Arg Leu Met
370                 375                 380

Ser Val Gly Leu Pro Asp Arg Glu His Arg Pro Gly Leu Phe Met Cys
385                 390                 395                 400

Val Gly Pro Pro Ser Phe Thr Ala Leu Ala Phe Ile Gly Met Ala Gln
                405                 410                 415

Gly Leu Pro Arg Asp Phe Asp His Asp Met Asp Gly Phe Ile Asp Ala
            420                 425                 430

Gly Met Ile Arg Thr Met Ala Val Ile Gly Ala Val Phe Leu Trp Ala
        435                 440                 445

Leu Ala Phe Trp Trp Phe Phe Ile Gly Val Leu Ala Val Leu Ala Ser
450                 455                 460

Arg Pro Lys Tyr Phe His Leu Gly Trp Trp Ala Ser Val Phe Pro Asn
465                 470                 475                 480

Thr Gly Phe Thr Leu Ala Thr Ile Ser Ile Gly Asn Ala Phe Gln Ser
                485                 490                 495

Asp Ala Val Leu Trp Val Gly Thr Gly Met Ser Leu Cys Leu Leu Gly
            500                 505                 510

Thr Tyr Leu Phe Val Leu Gly Asn His Val Arg Ala Val Val Val Gln
        515                 520                 525

Asp Ile Cys Tyr Pro Gly Arg Asp Glu Asp Val Glu Asp His
530                 535                 540
```

```
<210> SEQ ID NO 15
<211> LENGTH: 1143
<212> TYPE: DNA
<213> ORGANISM: Trichodermareesei

<400> SEQUENCE: 15
atgaaagcgg cattccctca tgccgtcgac ataaacgacc cgaaccgacc aaagcttcct      60
atccgacaga ggcttcagca cttcacatgg gcgtggtaca ctctgcccat gagcacgggg     120
ggtctctccc tgctcatcta cgcacagcca taccagttcg cgggcgaaag ggtgattggc     180
ttagtcgtat acattatcaa cctcatcatc tttccttgg tgacaatggc catgatggct      240
cgcttcttcc tacacgccgg agagtttgtc cggtccatca ctcatcccg tgaaggcttc      300 ttcgtcccca cattcttcct gtctctggcc accatcatca cgagcacgca gcgttatgcc     360
ataccggacg accatccgat actggaacct gccgtcaaga ttgcattctg ggtgtacgtc     420
gccctgacgg cggttctagc cctgggccag tacagctacg tctttgcggc ccataacctc     480
agcctcaaga ccttcatgcc aaccttgatt ctgcccatct ccccatcat gctttcagga      540 accattgcat ccgtcatcgc gggcacgcag cccgagttcg atgcgatgcc catcctagtc     600
gccggcctca cctgccaggg cctcggcatg tctgtggcca tcctcatgta cgcccacatg     660
attgggcgcc tgctccagtt cggcctgccc aaccgggagc atcgacccgg tctcttcatg     720
tgcgtcggtc cgccggcatt taccgccttg gccctggtcg gcatggccaa cggcgtgcct     780
gagggcatca gcgagctggg catcgacaag agcgtcatcc aggtcgtggc tatcctcgtc     840
gccgtgttcc tgtgggcgct gagcttctgg tggtttggca ttgccgtcat tgctgttgtc     900
tcgtcgccgc caaagtattt ccatctgggc tggtgggcca tggtgtttcc caacacgggc     960
tttacgctgg cgacgatttc cattgccaag gagttgctta gtcctagtct gcagtgggtt    1020
actattggta tgagctgctg catctttacc atcttcatct ttgtctttgt gaaccatgtt    1080
cgtgctgtga tcatccagga catcatgtat ccgggacgag atgagaatgt ggaggatcac    1140
tga                                                                  1143

<210> SEQ ID NO 16
<211> LENGTH: 380
<212> TYPE: PRT
<213> ORGANISM: Trichodermareesei

<400> SEQUENCE: 16

Met Lys Ala Ala Phe Pro His Ala Val Asp Ile Asn Asp Pro Asn Arg
1               5                   10                  15

Pro Lys Leu Pro Ile Arg Gln Arg Leu Gln His Phe Thr Trp Ala Trp
            20                  25                  30

Tyr Thr Leu Pro Met Ser Thr Gly Gly Leu Ser Leu Leu Ile Tyr Ala
        35                  40                  45

Gln Pro Tyr Gln Phe Ala Gly Glu Arg Val Ile Gly Leu Val Val Tyr
    50                  55                  60

Ile Ile Asn Leu Ile Ile Phe Ser Leu Val Thr Met Ala Met Met Ala
65                  70                  75                  80

Arg Phe Phe Leu His Ala Gly Glu Phe Val Arg Ser Ile Thr His Pro
                85                  90                  95

Arg Glu Gly Phe Phe Val Pro Thr Phe Phe Leu Ser Leu Ala Thr Ile
            100                 105                 110

Ile Thr Ser Thr Gln Arg Tyr Ala Ile Pro Asp Asp His Pro Ile Leu
        115                 120                 125
```

Glu Pro Ala Val Lys Ile Ala Phe Trp Val Tyr Val Ala Leu Thr Ala
130                 135                 140

Val Leu Ala Leu Gly Gln Tyr Ser Tyr Val Phe Ala Ala His Asn Leu
145                 150                 155                 160

Ser Leu Lys Thr Phe Met Pro Thr Leu Ile Leu Pro Ile Phe Pro Ile
                165                 170                 175

Met Leu Ser Gly Thr Ile Ala Ser Val Ile Ala Gly Thr Gln Pro Glu
            180                 185                 190

Phe Asp Ala Met Pro Ile Leu Val Ala Gly Leu Thr Cys Gln Gly Leu
        195                 200                 205

Gly Met Ser Val Ala Ile Leu Met Tyr Ala His Met Ile Gly Arg Leu
    210                 215                 220

Leu Gln Phe Gly Leu Pro Asn Arg Glu His Arg Pro Gly Leu Phe Met
225                 230                 235                 240

Cys Val Gly Pro Pro Ala Phe Thr Ala Leu Ala Leu Val Gly Met Ala
                245                 250                 255

Asn Gly Val Pro Glu Gly Ile Ser Glu Leu Gly Ile Asp Lys Ser Val
            260                 265                 270

Ile Gln Val Val Ala Ile Leu Val Ala Val Phe Leu Trp Ala Leu Ser
        275                 280                 285

Phe Trp Trp Phe Gly Ile Ala Val Ile Ala Val Val Ser Ser Pro Pro
    290                 295                 300

Lys Tyr Phe His Leu Gly Trp Trp Ala Met Val Phe Pro Asn Thr Gly
305                 310                 315                 320

Phe Thr Leu Ala Thr Ile Ser Ile Ala Lys Glu Leu Leu Ser Pro Ser
                325                 330                 335

Leu Gln Trp Val Thr Ile Gly Met Ser Cys Cys Ile Phe Thr Ile Phe
            340                 345                 350

Ile Phe Val Phe Val Asn His Val Arg Ala Val Ile Ile Gln Asp Ile
        355                 360                 365

Met Tyr Pro Gly Arg Asp Glu Asn Val Glu Asp His
    370                 375                 380

<210> SEQ ID NO 17
<211> LENGTH: 1251
<212> TYPE: DNA
<213> ORGANISM: Myceliophthora thermophila

<400> SEQUENCE: 17
atgaacgttg aaacgagcct ccctggctcg tctggttcgg atctggaaac cttccaccat      60
gagaccaaga acatgccaac catgattccg gaatatctg tcaatcacga agccgaaata     120
ggcgtcaacc atacattcga gaagccaggt ccagtgggga tccgcgaacg tttacgccat     180
tttacctggg cctggtacac cttgaccatg agctgcggcg gttggccct ccttattgtc     240 aaccagcctc atgacttcaa gggcttgaag acattgccc gggtagtcta ctgtctcaac     300
cttgcattct tcgtcatcgt cacttctctc atggccatca gattcatcct gcataagaat     360
atgtgggagt ctctcggtca tgaccgtgaa ggtctcttct tcccgacctt ctggcttttcc    420 attgcaacca tgatcactgg attgtacaag tgcttcggtg atgacgcgaa cgagaaattt     480
accaagtgtc tccaagtcct cttctggatc tactgtggct gtaccatgat caccgccgtc     540
ggtcagtact ctttttgtctt tgccacccat aaatacgagt tgcacaccat gatgccttcg     600
tggattttgc ctgccttccc tgtcatgctt agtggtacca tcgcgtctgt tatcggaagc     660
ggccagccag ccagtgacgg tatccctatc atcatagctg gcattacctt ccagggactt     720

```
ggtttctcga tcagtttcat gatgtacgcc cactacatcg gacgactgat ggaggtcggc    780
ttgccttccc ccgaacacag gcctggcatg ttcatctgtg ttggcccacc tgcctttact    840
gccctcgctt tggttggtat ggctaaggcg ttgcctgatg atttccagat cgtcggtgat    900
ccccatgctg ttattgacgg acgcgtcatg ctgttcctcg ctgtcagtgc ggccatcttc    960
ctttgggccc tgagtttctg gttttctgc attgcggttg ttgctgtcgt ccgatccccg   1020
ccgaagggtt tccacctcaa ctggttcgct atggtcttcc ccaacacggg tttcacccct   1080
gccaccatca ccctggccaa catgtttgag agcccaggcg tcaagggcgt ggccaccgcc   1140
atgtctctct gtgtcatcat catgtttatc tttgtcttgg ttagcgccat ccgggccgtt   1200
atccgcaagg acatcatgtg gccgggtcaa gatgaggatg tgtctgaatg a            1251
```

<210> SEQ ID NO 18
<211> LENGTH: 513
<212> TYPE: PRT
<213> ORGANISM: Myceliophthora thermophila

<400> SEQUENCE: 18

```
Met Ser Thr Pro Arg Arg Ser Thr Tyr Val Tyr Ser Gly Thr Gly Tyr
1               5                   10                  15

Gln Pro Phe Ala Val Gln Glu Asp Arg Pro Leu Pro Asp Pro Tyr Arg
            20                  25                  30

Ser Leu Arg Gly Pro Pro Ala Gln Ala Glu Glu Ala Gly Phe Gln
        35                  40                  45

Ser Ser Gln Ser Thr Ile Arg Gly Ser Pro Thr Ala Ser Gly Arg Ser
    50                  55                  60

Ser Thr Glu Tyr Ser Glu Ser Tyr Val Gly Asp Ile Glu Lys Ser Leu
65                  70                  75                  80

His Asn Asp Thr Val Pro Ser Leu Pro Leu His Ser Leu Gln Ser Asp
                85                  90                  95

Asn Gly Ser His Asp Gly Glu Gln Gln Asp Lys Glu Lys Tyr Gly Ala
            100                 105                 110

Pro Gly Val Glu Met Lys Ser Thr Thr Thr Thr Gly Ala Ala Ala
        115                 120                 125

Asp His Ser Gly Glu Thr Gly Ala Arg Ala Arg Pro Lys Leu Pro Ile
    130                 135                 140

Arg Glu Arg Leu Lys His Phe Thr Trp Ala Trp Tyr Thr Leu Ile Met
145                 150                 155                 160

Ser Thr Gly Gly Leu Ser Leu Leu Met Arg Ala Gln Pro His Gln Phe
                165                 170                 175

Pro Gly Leu Phe Gln Ile Gly Leu Ala Val Phe Val Ile Asn Ile Val
            180                 185                 190

Leu Phe Val Leu Val Thr Leu Ala Gln Ile Ala Arg Phe Val Leu Phe
        195                 200                 205

Pro Gly Ile Phe Ala Arg Ser Leu Gly His Arg Glu Gly Phe Phe
    210                 215                 220

Phe Pro Thr Phe Phe Leu Ala Val Ala Thr Leu Ile Thr Cys Thr Gln
225                 230                 235                 240

Arg Tyr Cys Val Pro Glu Asp Ala Asp Glu Ala Arg Ala Thr Ala Gly
                245                 250                 255

Thr Leu Leu Trp Leu Leu Arg Ala Ala Phe Trp Thr Tyr Leu Leu Leu
            260                 265                 270

Ala Thr Cys Val Ala Val Gly Gln Tyr Ser Tyr Val Phe Ser Ala His
```

```
                 275                 280                 285
Ser Phe Gly Leu Gln Thr Met Met Pro Thr Trp Ile Leu Pro Ile Phe
    290                 295                 300

Pro Val Met Leu Ser Gly Thr Ile Ala Ser Val Ile Ala Gly Ser Gln
305                 310                 315                 320

Pro Pro Glu Glu Ala Val Pro Ile Ala Val Ala Gly Leu Thr Cys Gln
                325                 330                 335

Gly Leu Gly Ile Ala Val Ala Phe Met Met Tyr Ala His Met Val Gly
                340                 345                 350

Arg Leu Met Gln Ser Gly Leu Pro Asp Arg Glu His Arg Thr Gly Leu
            355                 360                 365

Phe Met Cys Val Gly Pro Pro Ala Phe Thr Ala Leu Ala Phe Ile Gly
        370                 375                 380

Leu Ala Thr Gly Leu Pro Gln Asp Phe Asp His Asp Met Asp Gly Phe
385                 390                 395                 400

Val Asp Ala Val Val Ile Glu Thr Met Gly Leu Val Gly Ala Gly Phe
                405                 410                 415

Leu Trp Ala Leu Ser Phe Trp Phe Gly Ile Ala Leu Leu Ala Val
                420                 425                 430

Leu Gln Ser Pro Pro Glu His Phe His Leu Gly Trp Trp Ala Ser Val
            435                 440                 445

Phe Pro Asn Thr Gly Phe Val Leu Ala Thr Ile Ser Ile Gly Lys Ala
        450                 455                 460

Tyr His Ser Glu Gly Ile Leu Trp Leu Ser Thr Ala Leu Ser Val Val
465                 470                 475                 480

Leu Leu Leu Thr Tyr Leu Phe Val Leu Tyr His His Val Arg Ala Val
                485                 490                 495

Ile Val Gln Asp Ile Met Tyr Pro Gly Arg Asp Glu Asp Val Glu Asp
            500                 505                 510

His

<210> SEQ ID NO 19
<211> LENGTH: 1143
<212> TYPE: DNA
<213> ORGANISM: Aspergillus niger

<400> SEQUENCE: 19
atgctgacac ctcccaagtt tgaggatgag aagcagcttg gtcccgtggg tatccgggag        60
aggcttcgtc atttcacttg ggcctggtac accttaacaa tgagtggagg agggctggcc       120
gtcctcatca tcagccagcc ctttgggttc gcgggattga gagagatcgg catcgctgtc       180
tacatcctca acctgatcct cttcgccctt gtctgctcta ccatggcgat aaggttcatc       240
ctgcacggca accttctgga gtccctccgt catgaccgcg agggtctctt cttcccgacc       300
ttctggctct ccgttgcaac catcatctgc ggcctgtctc gctacttcgg tgacgaatcg       360
aatgaatcct ccaactagc cctcgaagcc ctcttctgga tctactgtgt ctgcacgtta       420
ctcgtcgcaa tcatccaata ctcgttcgtc ttctcatccc acaagtacgg ccttcaaacc       480
atgatgcctt catggatcct cccagccttc cccatcatgc tcagcggcac catcgcctcc       540
gtcatcggtg aacaacaacc cgctcgcgcc gccctcccca tcatcggcgc cggcgtcacc       600
ttccagggcc tcggcttctc catcagcttc atgatgtacg cccactacat cggccgactg       660
atggagtccg gctccccca cagcgaccac agaccaggca tgttcatctg catcgggccc       720
cctgccttca cagcccctgc cctcgtcggc atgagcaaag gcctccccga agacttcaag       780
```

-continued

```
ctgctccacg acgccaatgc tctggaagac ggccgtatca tcgagctgct agccatctcc    840
gccggcgtct tcctctgggc cctgagtctc tggttcttct gcatcgccat cgtcgccgtc    900
atccgctcgc cccccaaggc cttccacctc aactggtggg ccatggtctt ccccaacacc    960
ggcttcaccc tggccaccat caccctgggc aaggctctca acagtgacgg cgtgaagggc   1020
gtcggctccg ccatgtccat ctgcatcgtg tgcatgtaca tcttcgtctt cgtcaacaac   1080
gtccgcgccg ttatccggaa ggatatcatg tacccgggta agatgagga tgtatctgat   1140 tag                                                                 1143
```

<210> SEQ ID NO 20
<211> LENGTH: 416
<212> TYPE: PRT
<213> ORGANISM: Aspergillus niger

<400> SEQUENCE: 20

```
Met Asn Val Glu Thr Ser Leu Pro Gly Ser Gly Ser Asp Leu Glu
1               5                   10                  15

Thr Phe His His Glu Thr Lys Lys His Ala Asn His Asp Ser Gly Ile
            20                  25                  30

Ser Val Asn His Glu Ala Glu Ile Gly Val Asn His Thr Phe Glu Lys
        35                  40                  45

Pro Gly Pro Val Gly Ile Arg Glu Arg Leu Arg His Phe Thr Trp Ala
    50                  55                  60

Trp Tyr Thr Leu Thr Met Ser Cys Gly Gly Leu Ala Leu Leu Ile Val
65                  70                  75                  80

Asn Gln Pro His Asp Phe Lys Gly Leu Lys Asp Ile Ala Arg Val Val
                85                  90                  95

Tyr Cys Leu Asn Leu Ala Phe Phe Val Ile Val Thr Ser Leu Met Ala
            100                 105                 110

Ile Arg Phe Ile Leu His Lys Asn Met Trp Glu Ser Leu Gly His Asp
        115                 120                 125

Arg Glu Gly Leu Phe Phe Pro Thr Phe Trp Leu Ser Ile Ala Thr Met
    130                 135                 140

Ile Thr Gly Leu Tyr Lys Cys Phe Gly Asp Asp Ala Asn Glu Lys Phe
145                 150                 155                 160

Thr Lys Cys Leu Gln Val Leu Phe Trp Ile Tyr Cys Gly Cys Thr Met
                165                 170                 175

Ile Thr Ala Val Gly Gln Tyr Ser Phe Val Phe Ala Thr His Lys Tyr
            180                 185                 190

Glu Leu His Thr Met Met Pro Ser Trp Ile Leu Pro Ala Phe Pro Val
        195                 200                 205

Met Leu Ser Gly Thr Ile Ala Ser Val Ile Gly Ser Gly Gln Pro Ala
    210                 215                 220

Ser Asp Gly Ile Pro Ile Ile Ala Gly Ile Thr Phe Gln Gly Leu
225                 230                 235                 240

Gly Phe Ser Ile Ser Phe Met Met Tyr Ala His Tyr Ile Gly Arg Leu
                245                 250                 255

Met Glu Val Gly Leu Pro Ser Pro Glu His Arg Pro Gly Met Phe Ile
            260                 265                 270

Cys Val Gly Pro Pro Ala Phe Thr Ala Leu Ala Leu Val Gly Met Ala
        275                 280                 285

Lys Ala Leu Pro Asp Asp Phe Gln Ile Val Gly Asp Pro His Ala Val
    290                 295                 300
```

```
Ile Asp Gly Arg Val Met Leu Phe Leu Ala Val Ser Ala Ala Ile Phe
305                 310                 315                 320

Leu Trp Ala Leu Ser Phe Trp Phe Phe Cys Ile Ala Val Val Ala Val
                325                 330                 335

Val Arg Ser Pro Pro Lys Gly Phe His Leu Asn Trp Phe Ala Met Val
            340                 345                 350

Phe Pro Asn Thr Gly Phe Thr Leu Ala Thr Ile Thr Leu Ala Asn Met
        355                 360                 365

Phe Glu Ser Pro Gly Val Lys Gly Val Ala Thr Ala Met Ser Leu Cys
    370                 375                 380

Val Ile Ile Met Phe Ile Phe Val Leu Val Ser Ala Ile Arg Ala Val
385                 390                 395                 400

Ile Arg Lys Asp Ile Met Trp Pro Gly Gln Asp Glu Asp Val Ser Glu
                405                 410                 415

<210> SEQ ID NO 21
<211> LENGTH: 1143
<212> TYPE: DNA
<213> ORGANISM: Aspergillus sojae

<400> SEQUENCE: 21
atgctgacac ctcccaagtt tgaggatgag aagcagctgg gccccgtggg tatccgggag    60
aggcttcgcc atttcacttg ggcctggtac acattaacga tgagtggagg agggctggcc   120
gtcctcatca tcagccagcc ctttgggttc gcgcggattga gagagatcgg catcgctgtc   180
tatatcctca acctgatcct cttcgccctt gtctgctcta ccatggctat aaggttcatc   240
ctgcacggca accttctgga gtccctccgt catgaccgcg agggtctctt cttcccgacc   300
ttctggctct ccgtcgcaac catcatctgc ggcttgtctc gctacttcgg tgaagaatcg   360
aatgagtcct ccaactagcc ctcgaagcc ctcttctgga tctactgcgt ctgcacctta   420
ctcgtcgcaa tcatccaata ctcgttcgtc ttctcatccc acaagtacgg ccttcaaacc   480
atgatgcctt catggatcct ccagccttc cccatcatgc tcagcggcac catcgcctcc   540
gtcatcggtg aacaacaacc cgctcgcgca gccctcccca tcatcggcgc cggcgtcacc   600
ttccagggcc tcggcttctc catcagcttc atgatgtacg cccactacat cggccgactg   660
atggagtccg gctccccca cagcgaccac agaccaggca tgttcatctg cgtcggaccc   720
cccgccttca cagccctcgc cctcgtcggc atgagcaaag gcctccccga agacttcaag   780
ctgctccacg acgcccacgc cctggaagat ggccgcatca tcgagctgct ggccatctcc   840
gccggcgtct tcctctgggc cctgagtctc tggttcttct gcatcgccat tgtcgccgtc   900
atccgctcgc ccccgaggc cttccacctc aactggtggg ccatggtctt ccccaacacc   960
ggcttcaccc tggccaccat caccctgggc aaggctctca acagtaacgg cgtgaagggc  1020
gtcggctccg ccatgtctat ctgcatcgtg tgcatgtaca tcttcgtctt tgtcaacaat  1080
gtccgcgccg ttatccggaa ggatatcatg tacccgggta agatgagga tgtatctgat  1140 tag                                                                  1143

<210> SEQ ID NO 22
<211> LENGTH: 380
<212> TYPE: PRT
<213> ORGANISM: Aspergillus sojae

<400> SEQUENCE: 22

Met Leu Thr Pro Pro Lys Phe Glu Asp Glu Lys Gln Leu Gly Pro Val
```

```
  1               5                  10                 15
Gly Ile Arg Glu Arg Leu Arg His Phe Thr Trp Ala Trp Tyr Thr Leu
                20                 25                 30
Thr Met Ser Gly Gly Gly Leu Ala Val Leu Ile Ile Ser Gln Pro Phe
                35                 40                 45
Gly Phe Arg Gly Leu Arg Glu Ile Gly Ile Ala Val Tyr Ile Leu Asn
                50                 55                 60
Leu Ile Leu Phe Ala Leu Val Cys Ser Thr Met Ala Ile Arg Phe Ile
 65                 70                 75                 80
Leu His Gly Asn Leu Leu Glu Ser Leu Arg His Asp Arg Glu Gly Leu
                85                 90                 95
Phe Phe Pro Thr Phe Trp Leu Ser Val Ala Thr Ile Ile Cys Gly Leu
                100                105                110
Ser Arg Tyr Phe Gly Asp Glu Ser Asn Glu Ser Phe Gln Leu Ala Leu
                115                120                125
Glu Ala Leu Phe Trp Ile Tyr Cys Val Cys Thr Leu Leu Val Ala Ile
                130                135                140
Ile Gln Tyr Ser Phe Val Phe Ser Ser His Lys Tyr Gly Leu Gln Thr
145                150                155                160
Met Met Pro Ser Trp Ile Leu Pro Ala Phe Pro Ile Met Leu Ser Gly
                165                170                175
Thr Ile Ala Ser Val Ile Gly Glu Gln Gln Pro Ala Arg Ala Ala Leu
                180                185                190
Pro Ile Ile Gly Ala Gly Val Thr Phe Gln Gly Leu Gly Phe Ser Ile
                195                200                205
Ser Phe Met Met Tyr Ala His Tyr Ile Gly Arg Leu Met Glu Ser Gly
                210                215                220
Leu Pro His Ser Asp His Arg Pro Gly Met Phe Ile Cys Ile Gly Pro
225                230                235                240
Pro Ala Phe Thr Ala Pro Ala Leu Val Gly Met Ser Lys Gly Leu Pro
                245                250                255
Glu Asp Phe Lys Leu Leu His Asp Ala Asn Ala Leu Glu Asp Gly Arg
                260                265                270
Ile Ile Glu Leu Leu Ala Ile Ser Ala Gly Val Phe Leu Trp Ala Leu
                275                280                285
Ser Leu Trp Phe Phe Cys Ile Ala Ile Val Ala Ile Arg Ser Pro
                290                295                300
Pro Lys Ala Phe His Leu Asn Trp Trp Ala Met Val Phe Pro Asn Thr
305                310                315                320
Gly Phe Thr Leu Ala Thr Ile Thr Leu Gly Lys Ala Leu Asn Ser Asp
                325                330                335
Gly Val Lys Gly Val Gly Ser Ala Met Ser Ile Cys Ile Val Cys Met
                340                345                350
Tyr Ile Phe Val Phe Val Asn Asn Val Arg Ala Val Ile Arg Lys Asp
                355                360                365
Ile Met Tyr Pro Gly Lys Asp Glu Asp Val Ser Asp
                370                375                380

<210> SEQ ID NO 23
<211> LENGTH: 30
<212> TYPE: DNA
<213> ORGANISM: artificial sequence
<220> FEATURE:
<223> OTHER INFORMATION: primer
```

<400> SEQUENCE: 23
gctctagaca gaagatgata ttgaaggagc                                    30

<210> SEQ ID NO 24
<211> LENGTH: 32
<212> TYPE: DNA
<213> ORGANISM: artificial sequence
<220> FEATURE:
<223> OTHER INFORMATION: primer

<400> SEQUENCE: 24
cccaagcttc tattcctttg ccctcggacg ag                                 32

<210> SEQ ID NO 25
<211> LENGTH: 3582
<212> TYPE: DNA
<213> ORGANISM: Aspergillus oryzae

<400> SEQUENCE: 25

| | |
|---|---|
| atggcggctc cgtttcgtca gcctgaggag gcggtcgatg acaccgagtt catcgatgac | 60 |
| caccatgaac acctccgtga taccgtgcac catcggttgc gcgccaattc ctccattatg | 120 |
| cacttccaga agatcctcgt cgccaaccgt ggtgagatcc ccattcgtat cttcagaacg | 180 |
| gcccacgagc tgtccttgca gacggttgct atctactctc atgaggatcg actgtcaatg | 240 |
| caccgtcaaa aggccgatga ggcctacatg attggccacc gcggtcagta caccctgtc | 300 |
| ggtgcgtacc tggcgggcga tgagatcatc aagatcgccc tggagcacgg tgtccagctg | 360 |
| atccaccgg gctacggttt cttgtccgag aacgccgact cgcccgcaa ggttgagaac | 420 |
| gccggcattg tctttgtggg acccactccc gataccattg acagcttggg tgacaaggtg | 480 |
| tcggcccgtc ggctggccat taagtgcgag gtccctgtcg ttccgggtac ggagggcccc | 540 |
| gtcgagcgct atgaggaggt caaggcgttc acagacacct atggcttccc catcatcatc | 600 |
| aaggctgcct ttggcggtgg tggccgtggt atgcgtgtgg tccgtgacca ggccgagctg | 660 |
| cgtgactcgt tcgagcgagc cacctctgag gcccgctccg ccttcggcaa tggtaccgtc | 720 |
| ttcgtcgagc gcttcctcga caaacccaag cacattgaag tccagcttct gggtgacagc | 780 |
| cacggcaacg ttgtccatct gttttgagcgt gactgctccg tgcagcgtcg tcaccagaag | 840 |
| gtcgttgagg ttgctccggc taaggacctg ccagccgatg tccgggaccg catcctggcc | 900 |
| gatgctgtga agctggccaa gtccgtcaac taccgtaacg ccggtacagc tgagttcctg | 960 |
| gtggaccagc agaaccgcca ctacttcatt gaaatcaatc ctcgtatcca agtcgagcac | 1020 |
| accatcaccg aagagattac tggtatcgat atcgtggctg cacagatcca gattgctgct | 1080 |
| ggtgcaagcc tcgagcaact gggcctgact caggaccgca tctccgcccg cggatttgcc | 1140 |
| attcaatgtc gtatcaccac ggaagatccc gccaagggt tctctccgga tactggtaag | 1200 |
| attgaggttt atcgttccgc tggtggtaac ggtgtccgtc tggatggtgg taacggtttc | 1260 |
| gctggtgcta tcatcacccc tcactacgac tccatgctgg tcaagtgtac ctgccgtggt | 1320 |
| tcgacctatg aaatcgctcg tcgcaaggtt gtgcgtgcct tggtcgagtt ccgtattcgt | 1380 |
| ggtgtgaaga ccaacattcc cttcctgact tcgcttctga gccacccgac cttcgtcgat | 1440 |
| ggaaactgct ggaccacttt catcgacgac acccctgaat tgttctctct tgtcggcagt | 1500 |
| cagaaccgtg cccagaagct gctcgcatac ctcggcgatg tagctgtcaa cggtagtagc | 1560 |
| atcaagggcc aaattggcga gcccaagctc aagggtgatg tcatcaagcc gaagcttttc | 1620 |
| gatgccgagg gcaagccgct tgacgtttcc gcccctgca ccaaggggttg gaagcagatt | 1680 |

```
ctggaccggg agggtccggc tgcctttgcg aaggccgtgc gtgccaacaa gggttgcttg    1740
atcatggata ctacctggcg tgacgccac cagtctttgc tggccacccg tgtgcgtacc    1800
atcgacttgt tgaacatcgc ccatgagacc agctacgcct actccaatgc gtacagtttg    1860
gaatgctggg gtggtgctac cttcgatgtg ccatgcgtt tcctctatga ggaccccctgg   1920 gaccgcctgc gcaagatgcg taaggctgtt cctaacatcc cattccagat gttgctccgt    1980
ggtgccaacg tgtcgccta ctcttccctc ccagacaacg ccatctacca cttctgtaag    2040
caggctaaga agtgcggtgt cgacattttc cgtgttttcg acgccctcaa cgatgtcgat    2100
cagctcgagg tcggtatcaa ggctgttcat gctgccgagg tgttgtcga ggccaccatg    2160 tgctacagcg gtgacatgct gaaccccac aagaagtaca acctggagta ctacatggcc    2220
ttggtggata gagttgtagc catgaagcct cacatccttg gtatcaagga tatgccggt    2280 gtgctgaagc cccaggccgc tcgcctgttg gtgggctcca tccgtcagcg ctaccctgac    2340
cttcccatcc acgtccacac ccacgactcc gctggtactg tgtagcttc catgattgcc    2400 tgtgcccagg cgggtgccga cgccgtggac gccgcgaccg acagcatgtc cggtatgacc    2460
tcccagccta gcattggtgc cattctggcc tctcttgagg gcactgagca agaccccggt    2520
ctcaacctcg cccacgtgcg cgctattgat agctactggg cacagctgcg cttgctctac    2580
tctcctttcg aggcgggtct cactggcccc gaccctgagg tctacgagca cgagatccct    2640
ggtggtcagt tgaccaacct tatcttccag gccagtcagc tcggcttggg ccagcagtgg    2700
gccgaaacca agaaggccta tgaggcggct aatgatttac tcggcgacat tgtaaaggtc    2760
actcccacct ccaaggtggt cggtgacttg gctcagttca tggtctcgaa caaactgact    2820
ccagaggatg ttgttgagcg tgctggtgag ctggacttcc ctggttctgt gctcgaattc    2880
ctcgaaggtc tcatgggaca gcccttcggt ggattccccg agccattgcg ctcccgcgcc    2940
ctgcgcgatc gccgcaagct cgagaagcgt ccaggtctct acctcgagcc tttggatttg    3000
gctaagatca agagccagat ccgtgagaag ttcggtgctg ctactgagta tgacgtggcc    3060
agctatgcca tgtatcccaa ggtcttcgag gactacaaga agttcgtcca gaagttcggt    3120
gatctctccg tcttgcccac acggtacttc ttggccaagc ctgagattgg cgaggagttc    3180
cacgttgagc tggagaaggg taaggtgctc atcctgaagt tgttggccat cggccctctt    3240
tcagagcaga ctggtcagcg tgaggtcttc tacgaagtca acggtgaggt gcgccaggtc    3300
gctgttgatg acaacaaggc ttccgtggac aacacttcac gccctaaggc cgatgtgggt    3360
gacagcagcc aggtcggtgc tcctatgagc ggtgtggttg ttgaaatccg tgtccacgat    3420
ggtctggagg ttaagaaggg tgacccactt gccgtcctga gtgccatgaa gatggaaatg    3480
gttatctctg ctcctcacag tggaaaggtc tccagcttgc tggtcaagga gggcgattct    3540
gtggatggcc aggatctcgt ctgcaagatc gtcaaagcgt aa                       3582
```

<210> SEQ ID NO 26  
<211> LENGTH: 1193  
<212> TYPE: PRT  
<213> ORGANISM: Aspergillus oryzae

<400> SEQUENCE: 26

Met Ala Ala Pro Phe Arg Gln Pro Glu Glu Ala Val Asp Asp Thr Glu
1               5                   10                  15

Phe Ile Asp Asp His His Glu His Leu Arg Asp Thr Val His His Arg
            20                  25                  30

```
Leu Arg Ala Asn Ser Ser Ile Met His Phe Gln Lys Ile Leu Val Ala
         35                  40                  45

Asn Arg Gly Glu Ile Pro Ile Arg Ile Phe Arg Thr Ala His Glu Leu
     50                  55                  60

Ser Leu Gln Thr Val Ala Ile Tyr Ser His Glu Asp Arg Leu Ser Met
 65                  70                  75                  80

His Arg Gln Lys Ala Asp Glu Ala Tyr Met Ile Gly His Arg Gly Gln
                 85                  90                  95

Tyr Thr Pro Val Gly Ala Tyr Leu Ala Gly Asp Glu Ile Ile Lys Ile
            100                 105                 110

Ala Leu Glu His Gly Val Gln Leu Ile His Pro Gly Tyr Gly Phe Leu
            115                 120                 125

Ser Glu Asn Ala Asp Phe Ala Arg Lys Val Glu Asn Ala Gly Ile Val
        130                 135                 140

Phe Val Gly Pro Thr Pro Asp Thr Ile Asp Ser Leu Gly Asp Lys Val
145                 150                 155                 160

Ser Ala Arg Arg Leu Ala Ile Lys Cys Glu Val Pro Val Val Pro Gly
                165                 170                 175

Thr Glu Gly Pro Val Glu Arg Tyr Glu Glu Val Lys Ala Phe Thr Asp
            180                 185                 190

Thr Tyr Gly Phe Pro Ile Ile Ile Lys Ala Ala Phe Gly Gly Gly Gly
            195                 200                 205

Arg Gly Met Arg Val Val Arg Asp Gln Ala Glu Leu Arg Asp Ser Phe
        210                 215                 220

Glu Arg Ala Thr Ser Glu Ala Arg Ser Ala Phe Gly Asn Gly Thr Val
225                 230                 235                 240

Phe Val Glu Arg Phe Leu Asp Lys Pro Lys His Ile Glu Val Gln Leu
                245                 250                 255

Leu Gly Asp Ser His Gly Asn Val Val His Leu Phe Glu Arg Asp Cys
            260                 265                 270

Ser Val Gln Arg Arg His Gln Lys Val Val Glu Val Ala Pro Ala Lys
        275                 280                 285

Asp Leu Pro Ala Asp Val Arg Asp Arg Ile Leu Ala Asp Ala Val Lys
        290                 295                 300

Leu Ala Lys Ser Val Asn Tyr Arg Asn Ala Gly Thr Ala Glu Phe Leu
305                 310                 315                 320

Val Asp Gln Gln Asn Arg His Tyr Phe Ile Glu Ile Asn Pro Arg Ile
                325                 330                 335

Gln Val Glu His Thr Ile Thr Glu Glu Ile Thr Gly Ile Asp Ile Val
            340                 345                 350

Ala Ala Gln Ile Gln Ile Ala Ala Gly Ala Ser Leu Glu Gln Leu Gly
            355                 360                 365

Leu Thr Gln Asp Arg Ile Ser Ala Arg Gly Phe Ala Ile Gln Cys Arg
        370                 375                 380

Ile Thr Thr Glu Asp Pro Ala Lys Gly Phe Ser Pro Asp Thr Gly Lys
385                 390                 395                 400

Ile Glu Val Tyr Arg Ser Ala Gly Gly Asn Gly Val Arg Leu Asp Gly
                405                 410                 415

Gly Asn Gly Phe Ala Gly Ala Ile Ile Thr Pro His Tyr Asp Ser Met
            420                 425                 430

Leu Val Lys Cys Thr Cys Arg Gly Ser Thr Tyr Glu Ile Ala Arg Arg
        435                 440                 445

Lys Val Val Arg Ala Leu Val Glu Phe Arg Ile Arg Gly Val Lys Thr
```

```
              450             455             460
Asn Ile Pro Phe Leu Thr Ser Leu Leu Ser His Pro Thr Phe Val Asp
465                 470                 475                 480

Gly Asn Cys Trp Thr Thr Phe Ile Asp Asp Thr Pro Glu Leu Phe Ser
                485                 490                 495

Leu Val Gly Ser Gln Asn Arg Ala Gln Lys Leu Leu Ala Tyr Leu Gly
            500                 505                 510

Asp Val Ala Val Asn Gly Ser Ser Ile Lys Gly Gln Ile Gly Glu Pro
                515                 520                 525

Lys Leu Lys Gly Asp Val Ile Lys Pro Lys Leu Phe Asp Ala Glu Gly
            530                 535                 540

Lys Pro Leu Asp Val Ser Ala Pro Cys Thr Lys Gly Trp Lys Gln Ile
545                 550                 555                 560

Leu Asp Arg Glu Gly Pro Ala Ala Phe Ala Lys Ala Val Arg Ala Asn
                565                 570                 575

Lys Gly Cys Leu Ile Met Asp Thr Thr Trp Arg Asp Ala His Gln Ser
            580                 585                 590

Leu Leu Ala Thr Arg Val Arg Thr Ile Asp Leu Leu Asn Ile Ala His
            595                 600                 605

Glu Thr Ser Tyr Ala Tyr Ser Asn Ala Tyr Ser Leu Glu Cys Trp Gly
            610                 615                 620

Gly Ala Thr Phe Asp Val Ala Met Arg Phe Leu Tyr Glu Asp Pro Trp
625                 630                 635                 640

Asp Arg Leu Arg Lys Met Arg Lys Ala Val Pro Asn Ile Pro Phe Gln
                645                 650                 655

Met Leu Leu Arg Gly Ala Asn Gly Val Ala Tyr Ser Ser Leu Pro Asp
            660                 665                 670

Asn Ala Ile Tyr His Phe Cys Lys Gln Ala Lys Lys Cys Gly Val Asp
            675                 680                 685

Ile Phe Arg Val Phe Asp Ala Leu Asn Asp Val Asp Gln Leu Glu Val
            690                 695                 700

Gly Ile Lys Ala Val His Ala Ala Glu Gly Val Val Glu Ala Thr Met
705                 710                 715                 720

Cys Tyr Ser Gly Asp Met Leu Asn Pro His Lys Lys Tyr Asn Leu Glu
                725                 730                 735

Tyr Tyr Met Ala Leu Val Asp Lys Ile Val Ala Met Lys Pro His Ile
            740                 745                 750

Leu Gly Ile Lys Asp Met Ala Gly Val Leu Lys Pro Gln Ala Ala Arg
            755                 760                 765

Leu Leu Val Gly Ser Ile Arg Gln Arg Tyr Pro Asp Leu Pro Ile His
            770                 775                 780

Val His Thr His Asp Ser Ala Gly Thr Gly Val Ala Ser Met Ile Ala
785                 790                 795                 800

Cys Ala Gln Ala Gly Ala Asp Ala Val Asp Ala Ala Thr Asp Ser Met
                805                 810                 815

Ser Gly Met Thr Ser Gln Pro Ser Ile Gly Ala Ile Leu Ala Ser Leu
            820                 825                 830

Glu Gly Thr Glu Gln Asp Pro Gly Leu Asn Leu Ala His Val Arg Ala
            835                 840                 845

Ile Asp Ser Tyr Trp Ala Gln Leu Arg Leu Leu Tyr Ser Pro Phe Glu
            850                 855                 860

Ala Gly Leu Thr Gly Pro Asp Pro Glu Val Tyr Glu His Glu Ile Pro
865                 870                 875                 880
```

Gly Gly Gln Leu Thr Asn Leu Ile Phe Gln Ala Ser Gln Leu Gly Leu
                885                 890                 895

Gly Gln Gln Trp Ala Glu Thr Lys Lys Ala Tyr Glu Ala Ala Asn Asp
            900                 905                 910

Leu Leu Gly Asp Ile Val Lys Val Thr Pro Thr Ser Lys Val Val Gly
            915                 920                 925

Asp Leu Ala Gln Phe Met Val Ser Asn Lys Leu Thr Pro Glu Asp Val
        930                 935                 940

Val Glu Arg Ala Gly Glu Leu Asp Phe Pro Gly Ser Val Leu Glu Phe
945                 950                 955                 960

Leu Glu Gly Leu Met Gly Gln Pro Phe Gly Phe Pro Glu Pro Leu
            965                 970                 975

Arg Ser Arg Ala Leu Arg Asp Arg Arg Lys Leu Glu Lys Arg Pro Gly
            980                 985                 990

Leu Tyr Leu Glu Pro Leu Asp Leu Ala Lys Ile Lys Ser Gln Ile Arg
            995                1000                1005

Glu Lys Phe Gly Ala Ala Thr Glu Tyr Asp Val Ala Ser Tyr Ala
        1010                1015                1020

Met Tyr Pro Lys Val Phe Glu Asp Tyr Lys Phe Val Gln Lys
        1025                1030                1035

Phe Gly Asp Leu Ser Val Leu Pro Thr Arg Tyr Phe Leu Ala Lys
        1040                1045                1050

Pro Glu Ile Gly Glu Glu Phe His Val Glu Leu Glu Lys Gly Lys
        1055                1060                1065

Val Leu Ile Leu Lys Leu Leu Ala Ile Gly Pro Leu Ser Glu Gln
        1070                1075                1080

Thr Gly Gln Arg Glu Val Phe Tyr Glu Val Asn Gly Glu Val Arg
        1085                1090                1095

Gln Val Ala Val Asp Asp Asn Lys Ala Ser Val Asp Asn Thr Ser
        1100                1105                1110

Arg Pro Lys Ala Asp Val Gly Asp Ser Ser Gln Val Gly Ala Pro
        1115                1120                1125

Met Ser Gly Val Val Val Glu Ile Arg Val His Asp Gly Leu Glu
        1130                1135                1140

Val Lys Lys Gly Asp Pro Leu Ala Val Leu Ser Ala Met Lys Met
        1145                1150                1155

Glu Met Val Ile Ser Ala Pro His Ser Gly Lys Val Ser Ser Leu
        1160                1165                1170

Leu Val Lys Glu Gly Asp Ser Val Asp Gly Gln Asp Leu Val Cys
        1175                1180                1185

Lys Ile Val Lys Ala
        1190

<210> SEQ ID NO 27
<211> LENGTH: 1026
<212> TYPE: DNA
<213> ORGANISM: Myceliophthora thermophila

<400> SEQUENCE: 27
atgaaaaagc ctgaactcac cgcgacgtct gtcgagaagt ttctgatcga aaagttcgac    60
agcgtctccg acctgatgca gctctcggag ggcgaagaat ctcgtgcttt cagcttcgat   120
gtaggagggc gtggatatgt cctgcgggta aatagctgcg ccgatggttt ctacaaagat   180
cgttatgttt atcggcactt tgcatcggcc gcgctcccga ttccggaagt gcttgacatt   240

```
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026

<210> SEQ ID NO 28
<211> LENGTH: 989
<212> TYPE: DNA
<213> ORGANISM: Myceliophthora thermophila

<400> SEQUENCE: 28
catgtacctt gacgtcctcc gaggttcgac atcagggttc gtcataggga gtgaaacacc     60
cgccatgatt ccgtagccgc gcgcgaagat acgaagcaga tatttcacgg acatggcgga    120
gatacttgtt tcccgtacta aggtagtcat gtcggagaca tctgaacgac agagctggcc    180
aagagaaccg accagttgcc ccaggacgat ctagacaaaa aaaaagagag atgagtgggc    240
cacttttgcc acaacatcga cggccctgcg accgccccca ggcaaacaaa caaaccgccg    300
aacaataata cttttgtcat tttaggagga gcgttgtatg gataaaaaca acatctcgtt    360
gctgcagaat gtggacttca aacttgcaga aaatgggagg cggatttgca tgatcggagg    420
gtagttgact cacgccgcag gctgcaaatc cgtcctccat tattccatga acaacttcgt    480
aaggttgggc tgagcgccaa tgcctaacgg accgggggcc acagcgcaac gtcccactta    540
aaggccagcg tgacatgcca gttccatacc aagtagtggc accagaggcg gccaatgctc    600
agtaagggca gggagggagg ctcaaacgat tggcaaaaag aggggcttgc cagttcagtt    660
ccctgtgcga gcgcgagagg ggcagtttca aatctggagg ggtgtgttgc gctggtctga    720
agagaaagag aagactgtac ttaataattg ttcaaagagt ccatcatcgc gttgcggact    780
cctctagctg tatttagagc cctatcatta cttgtcgggt gcgaatcaaa ataccgggat    840
gcagccctct ggcgatttgc atgcggttgt ggaggaagtg aagcctgaat cgcggggctg    900
ggcggcaaag cacgacgtga aattcctggc gaaattcgag ggcttgcccc accgtggttg    960 aagttttttgt gctgcgtaac cccaccaac                                    989

<210> SEQ ID NO 29
<211> LENGTH: 33
<212> TYPE: DNA
<213> ORGANISM: artificial sequence
<220> FEATURE:
<223> OTHER INFORMATION: primer
```

<400> SEQUENCE: 29
ccttaattaa catgtaccttt gacgtcctcc gag                          33

<210> SEQ ID NO 30
<211> LENGTH: 31
<212> TYPE: DNA
<213> ORGANISM: artificial sequence
<220> FEATURE:
<223> OTHER INFORMATION: primer

<400> SEQUENCE: 30
ggactagttc tgaagaacga aactggcgac t                             31

<210> SEQ ID NO 31
<211> LENGTH: 30
<212> TYPE: DNA
<213> ORGANISM: artificial sequence
<220> FEATURE:
<223> OTHER INFORMATION: primer

<400> SEQUENCE: 31
ccatcgatca tcaagaacct gtaccgcatc                               30

<210> SEQ ID NO 32
<211> LENGTH: 32
<212> TYPE: DNA
<213> ORGANISM: artificial sequence
<220> FEATURE:
<223> OTHER INFORMATION: primer

<400> SEQUENCE: 32
gggtttaaac caatgatggg gatcttcagg tc                            32

<210> SEQ ID NO 33
<211> LENGTH: 31
<212> TYPE: DNA
<213> ORGANISM: artificial sequence
<220> FEATURE:
<223> OTHER INFORMATION: primer

<400> SEQUENCE: 33
cgcggatccc aatgatgggg atcttcaggt c                             31

<210> SEQ ID NO 34
<211> LENGTH: 39
<212> TYPE: DNA
<213> ORGANISM: artificial sequence
<220> FEATURE:
<223> OTHER INFORMATION: primer

<400> SEQUENCE: 34
cgcggatccg tttaaaccat caagaacctg taccgcatc                     39

<210> SEQ ID NO 35
<211> LENGTH: 29
<212> TYPE: DNA
<213> ORGANISM: artificial sequence
<220> FEATURE:
<223> OTHER INFORMATION: primer

<400> SEQUENCE: 35
ggactagtat ggcgccgacg tcaacaacg                                29

<210> SEQ ID NO 36
<211> LENGTH: 29

<212> TYPE: DNA
<213> ORGANISM: artificial sequence
<220> FEATURE:
<223> OTHER INFORMATION: primer

<400> SEQUENCE: 36
cggaattctc attgcacctc ccgaaccac                              29

<210> SEQ ID NO 37
<211> LENGTH: 29
<212> TYPE: DNA
<213> ORGANISM: artificial sequence
<220> FEATURE:
<223> OTHER INFORMATION: primer

<400> SEQUENCE: 37
ggactagtat gtccaaggcc gcaactgtc                              29

<210> SEQ ID NO 38
<211> LENGTH: 30
<212> TYPE: DNA
<213> ORGANISM: artificial sequence
<220> FEATURE:
<223> OTHER INFORMATION: primer

<400> SEQUENCE: 38
cggaattcct acgccgtctt tgcgttcatc                             30

<210> SEQ ID NO 39
<211> LENGTH: 34
<212> TYPE: DNA
<213> ORGANISM: artificial sequence
<220> FEATURE:
<223> OTHER INFORMATION: primer

<400> SEQUENCE: 39
gctctagatg cttgcaggaa ctctctgtga aacc                        34

<210> SEQ ID NO 40
<211> LENGTH: 33
<212> TYPE: DNA
<213> ORGANISM: artificial sequence
<220> FEATURE:
<223> OTHER INFORMATION: primer

<400> SEQUENCE: 40
gcgttaaccc cacagtttgg agagacgaca tcg                         33

<210> SEQ ID NO 41
<211> LENGTH: 35
<212> TYPE: DNA
<213> ORGANISM: artificial sequence
<220> FEATURE:
<223> OTHER INFORMATION: primer

<400> SEQUENCE: 41
ccttaattaa tgtatatacg gggcgaatac gaagg                       35

<210> SEQ ID NO 42
<211> LENGTH: 32
<212> TYPE: DNA
<213> ORGANISM: artificial sequence
<220> FEATURE:
<223> OTHER INFORMATION: primer

<400> SEQUENCE: 42

```
cggaattctt cctcctgcaa actcagcttg ag                                    32
```

<210> SEQ ID NO 43
<211> LENGTH: 65
<212> TYPE: DNA
<213> ORGANISM: artificial sequence
<220> FEATURE:
<223> OTHER INFORMATION: primer

<400> SEQUENCE: 43

```
ggaagatctt aattaactcg agcggccgcg tttaaacact agtatgctga cacctcccaa      60
gtttg                                                                  65
```

<210> SEQ ID NO 44
<211> LENGTH: 28
<212> TYPE: DNA
<213> ORGANISM: artificial sequence
<220> FEATURE:
<223> OTHER INFORMATION: primer

<400> SEQUENCE: 44

```
atcctaatca gatacatcct catcttta                                         28
```

<210> SEQ ID NO 45
<211> LENGTH: 30
<212> TYPE: DNA
<213> ORGANISM: artificial sequence
<220> FEATURE:
<223> OTHER INFORMATION: primer

<400> SEQUENCE: 45

```
ggactagtat gggcagccag cctcccatgc                                       30
```

<210> SEQ ID NO 46
<211> LENGTH: 30
<212> TYPE: DNA
<213> ORGANISM: artificial sequence
<220> FEATURE:
<223> OTHER INFORMATION: primer

<400> SEQUENCE: 46

```
cggaattcct aatgatcctc cacatcctca                                       30
```

<210> SEQ ID NO 47
<211> LENGTH: 31
<212> TYPE: DNA
<213> ORGANISM: artificial sequence
<220> FEATURE:
<223> OTHER INFORMATION: primer

<400> SEQUENCE: 47

```
ggactagtat gaaagcggca ttccctcatg c                                     31
```

<210> SEQ ID NO 48
<211> LENGTH: 32
<212> TYPE: DNA
<213> ORGANISM: artificial sequence
<220> FEATURE:
<223> OTHER INFORMATION: primer

<400> SEQUENCE: 48

```
cggaattctc agtgatcctc cacattctca tc                                    32
```

<210> SEQ ID NO 49
<211> LENGTH: 29

```
<212> TYPE: DNA
<213> ORGANISM: artificial sequence
<220> FEATURE:
<223> OTHER INFORMATION: primer

<400> SEQUENCE: 49
cggactagta tgtcaacacc gcggcgaag                                    29

<210> SEQ ID NO 50
<211> LENGTH: 30
<212> TYPE: DNA
<213> ORGANISM: artificial sequence
<220> FEATURE:
<223> OTHER INFORMATION: primer

<400> SEQUENCE: 50
ccggaattct taatgatcct ccacgtcctc                                   30

<210> SEQ ID NO 51
<211> LENGTH: 26
<212> TYPE: DNA
<213> ORGANISM: artificial sequence
<220> FEATURE:
<223> OTHER INFORMATION: primer

<400> SEQUENCE: 51
ggactagtat gaacgttgaa acgagc                                       26

<210> SEQ ID NO 52
<211> LENGTH: 28
<212> TYPE: DNA
<213> ORGANISM: artificial sequence
<220> FEATURE:
<223> OTHER INFORMATION: primer

<400> SEQUENCE: 52
cggaattctc attcagacac atcctcat                                     28

<210> SEQ ID NO 53
<211> LENGTH: 36
<212> TYPE: DNA
<213> ORGANISM: artificial sequence
<220> FEATURE:
<223> OTHER INFORMATION: primer

<400> SEQUENCE: 53
gctctagaat gctgacacct cccaagtttg aggatg                            36

<210> SEQ ID NO 54
<211> LENGTH: 38
<212> TYPE: DNA
<213> ORGANISM: artificial sequence
<220> FEATURE:
<223> OTHER INFORMATION: primer

<400> SEQUENCE: 54
ccttaattaa ctaatcagat acatcctcat ctttaccc                          38

<210> SEQ ID NO 55
<211> LENGTH: 31
<212> TYPE: DNA
<213> ORGANISM: artificial sequence
<220> FEATURE:
<223> OTHER INFORMATION: primer

<400> SEQUENCE: 55
```
gaagatctca tgtaccttga cgtcctccga g    31

<210> SEQ ID NO 56
<211> LENGTH: 31
<212> TYPE: DNA
<213> ORGANISM: artificial sequence
<220> FEATURE:
<223> OTHER INFORMATION: primer

<400> SEQUENCE: 56
ggactagttc tgaagaacga aactggcgac t    31

<210> SEQ ID NO 57
<211> LENGTH: 31
<212> TYPE: DNA
<213> ORGANISM: artificial sequence
<220> FEATURE:
<223> OTHER INFORMATION: primer

<400> SEQUENCE: 57
gggtttaaac atggcggctc cgtttcgtca g    31

<210> SEQ ID NO 58
<211> LENGTH: 32
<212> TYPE: DNA
<213> ORGANISM: artificial sequence
<220> FEATURE:
<223> OTHER INFORMATION: primer

<400> SEQUENCE: 58
gggtttaaac ttacgctttg acgatcttgc ag    32

<210> SEQ ID NO 59
<211> LENGTH: 31
<212> TYPE: DNA
<213> ORGANISM: artificial sequence
<220> FEATURE:
<223> OTHER INFORMATION: primer

<400> SEQUENCE: 59
cggactagta tggtcaaagc tgtcgttgct g    31

<210> SEQ ID NO 60
<211> LENGTH: 30
<212> TYPE: DNA
<213> ORGANISM: artificial sequence
<220> FEATURE:
<223> OTHER INFORMATION: primer

<400> SEQUENCE: 60
cgcggatcct cacttctggg ggggttgtg    30

<210> SEQ ID NO 61
<211> LENGTH: 33
<212> TYPE: DNA
<213> ORGANISM: artificial sequence
<220> FEATURE:
<223> OTHER INFORMATION: primer

<400> SEQUENCE: 61
ccttaattaa gtccagatca tggttgaccg gtg    33

<210> SEQ ID NO 62
<211> LENGTH: 53
<212> TYPE: DNA
<213> ORGANISM: artificial sequence
<220> FEATURE:
<223> OTHER INFORMATION: primer

<400> SEQUENCE: 62
gaacctcctt cagagaggtt cgtgtttaaa ctgatgtctg ctcaagcggg gta        53

<210> SEQ ID NO 63
<211> LENGTH: 52
<212> TYPE: DNA
<213> ORGANISM: artificial sequence
<220> FEATURE:
<223> OTHER INFORMATION: primer

<400> SEQUENCE: 63
accccgcttg agcagacatc agtttaaaca cgaacctctc tgaaggaggt tc         52

<210> SEQ ID NO 64
<211> LENGTH: 34
<212> TYPE: DNA
<213> ORGANISM: artificial sequence
<220> FEATURE:
<223> OTHER INFORMATION: primer

<400> SEQUENCE: 64
cccaagcttc taatagggat aataagctag ggtc                             34

<210> SEQ ID NO 65
<211> LENGTH: 34
<212> TYPE: DNA
<213> ORGANISM: artificial sequence
<220> FEATURE:
<223> OTHER INFORMATION: primer

<400> SEQUENCE: 65
ctttctagac gacgttaact gatattgaag gagc                             34

<210> SEQ ID NO 66
<211> LENGTH: 50
<212> TYPE: DNA
<213> ORGANISM: artificial sequence
<220> FEATURE:
<223> OTHER INFORMATION: primer

<400> SEQUENCE: 66
cgtgcaatcc atcttgttca atcatttgga tgcttgggta aataggtaa             50

<210> SEQ ID NO 67
<211> LENGTH: 50
<212> TYPE: DNA
<213> ORGANISM: artificial sequence
<220> FEATURE:
<223> OTHER INFORMATION: primer

<400> SEQUENCE: 67
ttacctattc tacccaagca tccaaatgat tgaacaagat ggattgcacg             50

<210> SEQ ID NO 68
<211> LENGTH: 54
<212> TYPE: DNA
<213> ORGANISM: artificial sequence
<220> FEATURE:
<223> OTHER INFORMATION: primer

<400> SEQUENCE: 68
aaaaaaagct tggtaccatc gatgcggccg cccgcggtca gaagaactcg tcaa        54

<210> SEQ ID NO 69
<211> LENGTH: 1464
<212> TYPE: DNA
<213> ORGANISM: Myceliophthora thermophila

<400> SEQUENCE: 69

| | |
|---|---|
| tgacggtgct tttcacctct cgatgcccga atcgggtct aagctgagtt tgatcaaata | 60 |
| tgtgactcca acatcgcccc cttcggcaaa ccccgtcgac acgtgtgtca tccttccatt | 120 |
| gcaagcgatc actcgcaggg cgtgacgatg aacgagattt tgcccggac cgattcgcgg | 180 |
| atatagcggc agccgaccag ccctaccaca ctgatggccg tgtccctagt gtatgctccc | 240 |
| agaaccgcaa gcatacactg gcaatgcttt ggtatgcagt tgaggcagct ttatgtttcc | 300 |
| ataccctttcc acttcggctc ggggactcgg cggggtcgcg gaagtttgac ggcagccgtc | 360 |
| gggccttagg ccgagattac cgtggttgtg gcccagtttt agccgttccc gtccgtttcc | 420 |
| taccggacca tgattttcgt gaaccattgc aatcccgaag cgcatttccg acgttaagga | 480 |
| gttacctccg ctgcccacaa ttcatgatcg tggccggctc aaggcagcgt ggcggggcat | 540 |
| ccgtgtcaag ctcccaggag gaggtgcgcg atttcaaatc cgggccaaaa caggccaaga | 600 |
| ctggctggcc aaaaaaagga gcgtagacgg cccgggacat cggacgtcag ctcgcagcca | 660 |
| cccaaaaccg gtccgatcta ctcgcttact gtggtagttc aggtactttt gagtagtaaa | 720 |
| aacgctacga cagggccggg gggttccccg gtgacggagg tgcctctgcg gtggcgaaca | 780 |
| tcccacgcac tatcgagcta cggtgacacc tcgtgtcctg ttggtcttgc aatgctgggg | 840 |
| cggcaggaaa tgcgtcgcgc tcctcccggc caagacctaa aacagacagc gccgcaaagt | 900 |
| cgctcactag caccgcgaaa cgaagatgcc ccacctcaac gcaatctgtg atgcaagcaa | 960 |
| ttgggaaggc tcaccccacc tcagcgaggg gctcaaccat ttttattatc agctcatgcc | 1020 |
| accacaacat gactgttttc tttccttgct catcccacat ttgacaaaaa tcgtcgatta | 1080 |
| atctctttcc atacaggccg tccgcgctct gataaccaca taaaagtctc ttcagtcaac | 1140 |
| agctcaaagc tccctcatcc ctccaggtaa gcagccaaag agctccccca cggaccccgc | 1200 |
| actgcctcat cccgcctgta tcggacctgc gcgacccagc agagaatccc aaacctttgc | 1260 |
| tgcttgctgc ccggttccgg actgagctgc aacccaagcc tttaaaaagc tattcccttc | 1320 |
| tcccacggtg tcaactctgt cctatcccctc cgacatccgt tgagctcaac aactccccga | 1380 |
| accttttacc ccgcgccgag ctacccctcc atcaaaccac cctgacagct cgctcactca | 1440 |
| cctccccaca tcacagaaat caaa | 1464 |

<210> SEQ ID NO 70
<211> LENGTH: 44
<212> TYPE: DNA
<213> ORGANISM: artificial sequence
<220> FEATURE:
<223> OTHER INFORMATION: primer

<400> SEQUENCE: 70

| | |
|---|---|
| tgcagatctt taattaactc gagtgacggt gcttttcacc tctc | 44 |

<210> SEQ ID NO 71
<211> LENGTH: 54
<212> TYPE: DNA
<213> ORGANISM: artificial sequence
<220> FEATURE:
<223> OTHER INFORMATION: primer

<400> SEQUENCE: 71

```
agtggatccg aattcgatat cgtttaaaca ctagttttga tttctgtgat gtgg         54
```

<210> SEQ ID NO 72
<211> LENGTH: 1000
<212> TYPE: DNA
<213> ORGANISM: Myceliophthora thermophila

<400> SEQUENCE: 72

```
gtctgctgag ccgcactcgt agccatctcc cccccacctt aatagataac agaaactaga    60
cacggtcgtt tgtaaaacaa gagttcaacc tcgtcatacg ctgctttcct gacatggacg   120
tctgctaggt gttaattttt ctgggctcac cgcgcattgc agaaaacctt agctctgaac   180
ttacacctac cacgcaccta cgtagttagg agtttcggca acggcagatg ggtcgggaga   240
atggcggctt gtcaacactc cctctacacc accaaggaca cccaaaatta aattagctgc   300
ggaatttttca gccgctgcag ccgatatcat gcaatcgaat cgacccttg ccagccgcat   360
gccgcctgtc gtcctggatc ttgttggcgg aggctgccga agaaacgtca tagggggaca   420
tggcgccgtg acgagtggga atggagacgc tttaacaagc aacgctcctg acccggtacc   480
tggaattgaa gtggggtctg gcgcagctca accgacctgg ctaagctctt tgacagggta   540
aataaagggc ccgctgggcc cctgctcacg gtccgacgcg cccggttctt gcctattggg   600
gcagcaaacc ttggggcagc atccgccccg aacttccgca tcgagctatc acggaggcgg   660
gcccggctca caggctcaac agacggagac ggcccgcccg atccgtgaaa agcttagccc   720
ccgcgacagc ggagcttaac ttggcgtaat taaggcatgt atgtatgtat gtacagtact   780
gtgtgtgttc cgtaccttta tttaaagcca gtcagtcgtc ttggcccccc aaaactgatc   840
gacacaccta cctggctgct cttccttgca caaagcgatc ggccgcaagt cttgaaataa   900
tactagtagt ggagttaccg aattcggtaa ttagtataca tccaccacaa tacactacca   960
caccaggcct gcagccaccc atcgctagcc atccgcagcc                         1000
```

<210> SEQ ID NO 73
<211> LENGTH: 1445
<212> TYPE: DNA
<213> ORGANISM: Myceliophthora thermophila

<400> SEQUENCE: 73

```
tttgagcgct gggcctcctt cggcaaacaa gttctcagct gtccccaaca tccatccact    60
cttgcatatt taagacagac cgaactatca gagcagccaa gcgtcagtcg gtactcaggg   120
ccgataccct ttcaagcgac ccacgaagac tggatggact ctggaacaag acggctctgg   180
cacacgccca tttggttctt ggtcttcatg cgcgaagcca gtggctctat tacacgctcg   240
actactacac acgtggagca gagtgccacg tcctcaagca gagagtggtc agctcgtgag   300
ccccgttcaa agtccggggt agcactctcg cggtccggct gcatctcgct cggcatgact   360
tcttgtttct gttctgtcgg cgccaccact ctgcgcgagg cggccccgtg gcgccggaac   420
acacgagttc tgattccgtc tcctcccct gcctggttga gcaaagatcg acggggaaat   480
cggatgcggc gagccaagcc cacgatacca aaatagcatc ccacacgtaa ttaccttgga   540
tcaggagatg gtggtgtggt gaaaggacgg taattaaacc cgtttttttct tttttttcttt   600
tttttttttt tttttaccg agcgctgtgg gcgttgatct cccgcaccag agtcgatcgc   660
cttttttcatt gtgagcgcgc atctcatcaa agctcgcacg atcttcgacc gttgcaagac   720
ttggcattcc ggtatttggg attcggaacc gatcgtttcc aaccccgca accctgcgc   780
```

| | |
|---|---|
| agagccaagc cgttgcgaac caacaaagcc agaattggga cgggacgtca tccgccgata | 840 |
| gcccggtttt tgggatcgcg gcgcacggca gagccattcc gcattgccgc actagtttat | 900 |
| ccagcatatt agccggcccc ccaaacccac caatggcccc tgccgccgca ccctgttttc | 960 |
| ggaaggcctg acgcacccca gatccccctt tgggtggtat ccatgtgggg agttggggag | 1020 |
| tcgcgcgctc cgattcttct gttcacgggg ctgccgccga ggagcgccga gcgtgcttcg | 1080 |
| gcggtgggac tcgagaacag aatggaaatt ggaggactgg cggagtcgtc acagctcact | 1140 |
| gcagtgaagg tttgggtttg cccgggctgc ggtgcggatg gggaagcccg agttggcgcc | 1200 |
| ggccttggta tccgtgggaa cgttcatcca ggttgccttg cagcccagcg ccctgctggg | 1260 |
| ggagagggag taaagaagga cgtgtgtgga tgggcggac ggcggacgga taccatacct | 1320 |
| agctatatat tatgtatctg cgccgtggcc tgtgacagga accactcaac tcctctgagc | 1380 |
| cttcaggact cttctccccc caaattcctc gacaagtccg actcggtcag gttctgtgta | 1440 |
| gcaac | 1445 |

<210> SEQ ID NO 74
<211> LENGTH: 500
<212> TYPE: DNA
<213> ORGANISM: Myceliophthora thermophila

<400> SEQUENCE: 74

| | |
|---|---|
| catcaagaac ctgtaccgca tcttcctcga gaaggacgcg acccagatcg agatcaaccc | 60 |
| gctctcggag acgtcggacc acaaggtcat gtgcatggat gccaagttcg gctttgacga | 120 |
| caacgccgag ttccgccaga aggaggtgtt cagctggcgc gacaccaccc aggaggaccc | 180 |
| ggaggaggtg cgggccgccg aggccgggct caacttcatc aagctggacg gcgacatcgg | 240 |
| ctgcctggtc aacggcgccg gcctggccat ggccaccatg gacattatca agctcaacgg | 300 |
| tgggcagccg gccaacttcc tcgacgtcgg cggcggcgcc accccggcgg ccatcaagga | 360 |
| ggcctttgag ctcatcacca gcgaccccaa ggtgacggcc atctttgtca acatctttgg | 420 |
| cggcatcgtg cgctgcgacg ccatcgccca cggcctcatc aacacggtca agtcgctcga | 480 |
| cctgaagatc cccatcattg | 500 |

<210> SEQ ID NO 75
<211> LENGTH: 500
<212> TYPE: DNA
<213> ORGANISM: Myceliophthora thermophila

<400> SEQUENCE: 75

| | |
|---|---|
| caatgatggg gatcttcagg tcgagcgact tgaccgtgtt gatgaggccg tgggcgatgg | 60 |
| cgtcgcagcg cacgatgccg ccaaagatgt tgacaaagat ggccgtcacc ttggggtcgc | 120 |
| tggtgatgag ctcaaaggcc tccttgatgg ccgccggggt ggcgccgccg ccgacgtcga | 180 |
| ggaagttggc cggctgccca ccgttgagct tgataatgtc catggtggcc atggccaggc | 240 |
| cggcgccgtt gaccaggcag ccgatgtcgc cgtccagctt gatgaagttg agcccggcct | 300 |
| cggcggcccg cacctcctcc gggtcctcct gggtggtgtc gcgccagctg aacacctcct | 360 |
| tctggcggaa ctcggcgttg tcgtcaaagc cgaacttggc atccatgcac atgaccttgt | 420 |
| ggtccgacgt ctccgagagc gggttgatct cgatctgggt cgcgtccttc tcgaggaaga | 480 |
| tgcggtacag gttcttgatg | 500 |

<210> SEQ ID NO 76
<211> LENGTH: 20

```
<212> TYPE: DNA
<213> ORGANISM: artificial sequence
<220> FEATURE:
<223> OTHER INFORMATION: primer

<400> SEQUENCE: 76
agctgtttac tcattattac                                              20

<210> SEQ ID NO 77
<211> LENGTH: 47
<212> TYPE: DNA
<213> ORGANISM: artificial sequence
<220> FEATURE:
<223> OTHER INFORMATION: primer

<400> SEQUENCE: 77
gctctagagt taacgcggcc gcgactagat ctgtgccaac gccacag                47

<210> SEQ ID NO 78
<211> LENGTH: 50
<212> TYPE: DNA
<213> ORGANISM: artificial sequence
<220> FEATURE:
<223> OTHER INFORMATION: primer

<400> SEQUENCE: 78
cggaattcgt ttaaacttaa ttaaccgacg gaattgagga tatcagtcac             50

<210> SEQ ID NO 79
<211> LENGTH: 30
<212> TYPE: DNA
<213> ORGANISM: artificial sequence
<220> FEATURE:
<223> OTHER INFORMATION: primer

<400> SEQUENCE: 79
gctctagaat gggcagccag cctcccatgc                                   30

<210> SEQ ID NO 80
<211> LENGTH: 32
<212> TYPE: DNA
<213> ORGANISM: artificial sequence
<220> FEATURE:
<223> OTHER INFORMATION: primer

<400> SEQUENCE: 80
ccttaattaa ctaatgatcc tccacatcct ca                                32

<210> SEQ ID NO 81
<211> LENGTH: 38
<212> TYPE: DNA
<213> ORGANISM: artificial sequence
<220> FEATURE:
<223> OTHER INFORMATION: primer

<400> SEQUENCE: 81
ccttaattaa ctaatcagat acatcctcat ctttaccc                          38

<210> SEQ ID NO 82
<211> LENGTH: 29
<212> TYPE: DNA
<213> ORGANISM: artificial sequence
<220> FEATURE:
<223> OTHER INFORMATION: primer

<400> SEQUENCE: 82
```

```
ttccaactag tatgctgaca cctcccaag                                    29
```

<210> SEQ ID NO 83
<211> LENGTH: 28
<212> TYPE: DNA
<213> ORGANISM: artificial sequence
<220> FEATURE:
<223> OTHER INFORMATION: primer

<400> SEQUENCE: 83

```
aatggttaac ctaatcagat acatcctc                                     28
```

<210> SEQ ID NO 84
<211> LENGTH: 1033
<212> TYPE: DNA
<213> ORGANISM: Aspeergillus nidulans

<400> SEQUENCE: 84

```
gtccagatca tggttgaccg gtgcctggat cttcctatag aatcatcctt attcgttgac    60
ctagctgatt ctggagtgac ccagagggtc atgacttgag cctaaaatcc gccgcctcca   120
ccatttgtag aaaaatgtga cgaactcgtg agctctgtac agtgaccggt gactcttcct   180
ggcatgcgga gagacggacg gacgcagaga aagggctga gtaataagcc actggccaga   240
cagctctggc ggctctgagg tgcagtggat gattattaat ccgggaccgg ccgcccctcc   300
gccccgaagt ggaaaggctg gtgtgcccct cgttgaccaa gaatctattg catcatcgga   360
gaatatggag cttcatcgaa tcaccggcag taagcgaagg agaatgtgaa gccaggggtg   420
tataccgtc ggcgaaatag catgccatta acctaggtac agaagtccaa ttgcttccga   480
tctggtaaaa gattcacgag atagtacctt ctccgaagta ggtagagcga gtacccggcg   540
cgtaagctcc ctaattggcc catccggcat ctgtagggcg tccaaatatc gtgcctctcc   600
tgctttgccc ggtgtatgaa accggaaagg ccgctcagga gctggccagc ggcgcagacc   660
gggaacacaa gctggcagtc gacccatccg gtgtctgca ctcgacctgc tgaggtccct    720
cagtccctgg taggcagctt tgccccgtct gtccgcccgg tgtgtcggcg gggttgacaa   780
ggtcgttgcg tcagtccaac atttgttgcc atattttcct gctctcccca ccagctgctc   840
tttctttttc tctttctttt cccatcttca gtatattcat cttcccatcc aagaaccttt   900
atttcccta agtaagtact tgctacatc catactccat ccttcccatc ccttattcct   960
ttgaaccttt cagttcgagc tttcccactt catcgcagct tgactaacag ctaccccgct  1020
tgagcagaca tca                                                    1033
```

<210> SEQ ID NO 85
<211> LENGTH: 964
<212> TYPE: DNA
<213> ORGANISM: Myceliophthora thermophila

<400> SEQUENCE: 85

```
acgaacctct ctgaaggagg ttctgagaca cgcgcgattc ttctgtatat agttttattt    60
ttcactctgg agtgcttcgc tccaccagta cataaacctt tttttcacg taacaaaatg    120
gcttcttttc agaccatgtg aaccatcttg atgccttgac ctcttcagtt ctcacttaa   180
cgtagttcgc gtttgtctgt atgtcccagt tgcatgtagt tgagataaat accctggaa   240
gtgggtctgg gcctttgtgg gacggagccc tctttctgtg gtctggagag cccgctctct   300
accgcctacc ttcttaccac agtacactac tcacacattg ctgaactgac ccatcatacc   360
gtactttatc ctgttaattc gtggtgctgt cgactattct atttgctcaa atggagagca   420
```

```
cattcatcgg cgcagggata cacggtttat ggaccccaag agtgtaagga ctattattag      480
taatattata tgcctctagg cgccttaact tcaacaggcg agcactacta atcaactttt      540
ggtagaccca attacaaacg accatacgtg ccggaaattt tgggattccg tccgctctcc      600
ccaaccaagc tagaagaggc aacgaacagc aatcccggt gctaattaaa ttatatggtt       660 ccatttttt aaaaaattt ttttcttccc attttcctct cgcttttctt tttcgcatcg        720
tagttgatca aagtccaagt caagcgagct atttgtgcta tagctcggtg gctataatca      780
gtacagctta gagaggctgt aaaggtatga taccacagca gtattcgcgc tataagcggc      840
actcctagac taattgttac ggtctacaga agtaggtaat aaaagcgtta attgttctaa      900
atactagagg cacttagaga agctatctaa atatatattg accctagctt attatcccta      960
ttag                                                                  964
```

```
<210> SEQ ID NO 86
<211> LENGTH: 368
<212> TYPE: DNA
<213> ORGANISM: Aspeergillus nidulans

<400> SEQUENCE: 86
cgacgttaac tgatattgaa ggagcatttt ttgggcttgg ctggagctag tggaggtcaa       60
caatgaatgc ctattttggt ttagtcgtcc aggcggtgag cacaaaattt gtgtcgtttg      120
acaagatggt tcatttaggc aactggtcag atcagcccca cttgtagcag tagcggcggc      180
gctcgaagtg tgactcttat tagcagacag gaacgaggac attattatca tctgctgctt      240
ggtgcacgat aacttggtgc gtttgtcaag caaggtaagt ggacgacccg gtcataccct      300
cttaagttcg cccttcctcc ctttatttca gattcaatct gacttaccta ttctacccaa      360
gcatccaa                                                              368
```

```
<210> SEQ ID NO 87
<211> LENGTH: 24
<212> TYPE: DNA
<213> ORGANISM: artificial sequence
<220> FEATURE:
<223> OTHER INFORMATION: primer

<400> SEQUENCE: 87
cagactgtgt ggttctgcaa cagg                                             24
```

```
<210> SEQ ID NO 88
<211> LENGTH: 23
<212> TYPE: DNA
<213> ORGANISM: artificial sequence
<220> FEATURE:
<223> OTHER INFORMATION: primer

<400> SEQUENCE: 88
ggccaacagt acgaagcatt tcg                                              23
```

```
<210> SEQ ID NO 89
<211> LENGTH: 22
<212> TYPE: DNA
<213> ORGANISM: artificial sequence
<220> FEATURE:
<223> OTHER INFORMATION: primer

<400> SEQUENCE: 89
atggcgtcag caaaggagaa gg                                               22
```

<210> SEQ ID NO 90
<211> LENGTH: 22
<212> TYPE: DNA
<213> ORGANISM: artificial sequence
<220> FEATURE:
<223> OTHER INFORMATION: primer

<400> SEQUENCE: 90
ctacgcctcg ccatccctaa tc					22

<210> SEQ ID NO 91
<211> LENGTH: 1372
<212> TYPE: DNA
<213> ORGANISM: Myceliophthora thermophila

<400> SEQUENCE: 91

```
atggcgtcag caaaggagaa ggcgccgctg ccgttccgct atacgttcat ggccggtgag      60
cggtttccca gagcatccc gaagcagccg ccgagactcg gtcagctaac caagtacttc     120
aattcaggcg ccattgccgg tgtatctgaa gcacgttgac caatggctcc aacgggcgtc     180
aattctcacg ctaacaccta gggcgcgcat agatcctggt catgtaagcc ctgccatgct     240
cggacgaggt cgcgcgcctc gcctcaattg ctaatgctga acgctcaaac aggtacccgc     300
tggatgtcgt gaagacaaga gtgtgagacg gcacctcccg ttcatttgat atcgaccctc     360
tctcccggct gacgaccgaa aagacagctg cagaccggta aaggctccgg tgccgatgcg     420
tacagtggca tgctcgactg cttccagaag atcatccgca acgaagggta tgcgtcagga     480
acactcggat acatggaagg ggtggtggtg ttgacatttt gggtagcttc tcgaggctct     540
accgcggcat taccgctccc attctcatgg aggcgcccaa gcgcgcgacc aagttcgcgg     600
ccaacgacaa atggggcaaa ttctacaagg atctctttgg ccagcagacc atgacacagt     660
cgctctcggt cctgactggt gcttcggccg gcgcgactga gtccttcgtc gtggtgccct     720
tcgagctcgt caagatccgc ctccaggaca aggcctcggc cggcaagtac agcggtatga     780
ttgatgttgt cgtcaagacg gtgcgcaacg aaggtctgct ggccatgtac aacggcctcg     840
agtctactct ctggcgccac attctctgga actcgggcta cttcggctgc atcttccagg     900
ttcggcaatt gctccccaag gcggagacga agtcgggaca acaatcaac gacatcgtcg     960
ccggtaccat tggcggcact gtcggcacga ttctgaatac ccgtacgtga aagccatcct    1020
aactctccct gcgcgccttg aatgagcacg agttccaccg ggcagccggc tctctttcc    1080
cgcatccacc tcctctagcc ctgaaacaag agaacgaaaa ctgacattat ttctagccat    1140
ggatgtcgtg aagagccgta tccagaacag cgtcaaggtt gccggccaaa cacccaagta    1200
caactgggcc tggcctgccg tggcgacggt tgccaaagag gaaggcttcg gggccctcta    1260
caaaggcttc atccccaagg ttctccggct gggacctggc ggcggcattc tcctcgtcgt    1320
ctacaccggg gtaatggact tcttccgcaa gattagggat ggcgaggcgt ag           1372
```

<210> SEQ ID NO 92
<211> LENGTH: 304
<212> TYPE: PRT
<213> ORGANISM: Myceliophthora thermophila

<400> SEQUENCE: 92

Met Ala Ser Ala Lys Glu Lys Ala Pro Leu Pro Phe Arg Tyr Thr Phe
1               5                   10                  15

Met Ala Gly Ala Ile Ala Gly Val Ser Glu Ile Leu Val Met Tyr Pro
            20                  25                  30

```
Leu Asp Val Val Lys Thr Arg Val Gln Leu Gln Thr Gly Lys Gly Ser
            35                  40                  45

Gly Ala Asp Ala Tyr Ser Gly Met Leu Asp Cys Phe Gln Lys Ile Ile
 50                  55                  60

Arg Asn Glu Gly Phe Ser Arg Leu Tyr Arg Gly Ile Thr Ala Pro Ile
 65                  70                  75                  80

Leu Met Glu Ala Pro Lys Arg Ala Thr Lys Phe Ala Ala Asn Asp Lys
                 85                  90                  95

Trp Gly Lys Phe Tyr Lys Asp Leu Phe Gly Gln Gln Thr Met Thr Gln
                100                 105                 110

Ser Leu Ser Val Leu Thr Gly Ala Ser Ala Gly Ala Thr Glu Ser Phe
                115                 120                 125

Val Val Val Pro Phe Glu Leu Val Lys Ile Arg Leu Gln Asp Lys Ala
        130                 135                 140

Ser Ala Gly Lys Tyr Ser Gly Met Ile Asp Val Val Lys Thr Val
145                 150                 155                 160

Arg Asn Glu Gly Leu Leu Ala Met Tyr Asn Gly Leu Glu Ser Thr Leu
                165                 170                 175

Trp Arg His Ile Leu Trp Asn Ser Gly Tyr Phe Gly Cys Ile Phe Gln
            180                 185                 190

Val Arg Gln Leu Leu Pro Lys Ala Glu Thr Lys Ser Gly Gln Thr Ile
        195                 200                 205

Asn Asp Ile Val Ala Gly Thr Ile Gly Gly Thr Val Gly Thr Ile Leu
    210                 215                 220

Asn Thr Pro Met Asp Val Val Lys Ser Arg Ile Gln Asn Ser Val Lys
225                 230                 235                 240

Val Ala Gly Gln Thr Pro Lys Tyr Asn Trp Ala Trp Pro Ala Val Ala
                245                 250                 255

Thr Val Ala Lys Glu Glu Gly Phe Gly Ala Leu Tyr Lys Gly Phe Ile
                260                 265                 270

Pro Lys Val Leu Arg Leu Gly Pro Gly Gly Ile Leu Leu Val Val
        275                 280                 285

Tyr Thr Gly Val Met Asp Phe Phe Arg Lys Ile Arg Asp Gly Glu Ala
        290                 295                 300

<210> SEQ ID NO 93
<211> LENGTH: 31
<212> TYPE: DNA
<213> ORGANISM: artificial sequence
<220> FEATURE:
<223> OTHER INFORMATION: primer

<400> SEQUENCE: 93
cggactagta tggtcaaagc tgtcgttgct g                                31

<210> SEQ ID NO 94
<211> LENGTH: 30
<212> TYPE: DNA
<213> ORGANISM: artificial sequence
<220> FEATURE:
<223> OTHER INFORMATION: primer

<400> SEQUENCE: 94
cgcggatcct cacttctggg gggggttgtg                                  30

<210> SEQ ID NO 95
<211> LENGTH: 1599
```

<212> TYPE: DNA
<213> ORGANISM: Neurospora crassa

<400> SEQUENCE: 95

```
atgggtctct tctcgaaaaa gtcggctgcg ccgcagaccc aatcacaaga tgagatcgat      60
ctcgctgctg agcagaaggt cactttccgt gccgtcttcc tcggtgttgt cgcctccgta     120
ggtggcttca tgtttggcta cgtcagtggt caaatttctg gtttcttcga catggaagac     180
ttcggtcgtc ggtccggtaa ctaccaagac gcggatggc gggtcttctc agcataccgc     240
cagggtgcta ttgtcgccct actccctgct ggtgcccttc ttggttcgct cgttgccggt     300
agaattgcgg ataccttgg tcgccgtatc gccatctctg cgtccgccct tttctcctgc     360
atcggaacaa ttatcgagat cgcctccacc acgcactggg cccagtttgc ggtcggtcgt     420
cttatcaccg gtattggtat cggtgctctc tccgtcgtcg tcccgatgta ccagtctgag     480
tccgcgcccg ccatcctccg tggtatcctc gtctcgtgct accagctctt catcactctt     540
ggtatctgga ccgctgagat gatcaactac ggtactcacg acctcagcaa ctccgcctct     600
tggcgtattc caacggtat ctccttcctc tgggctttgg ttctcggtgg cggaatattg     660
ttccttcctg agtctccccg ttatgcctac cgtgttggtc gcgaggacga ggctcgcaac     720
accattgccc gccttgccgg tctcgagccc agcgcccgct ctgtcaacat gcaaatcgat     780
gagatccgta tgaagcttga ggaggagaag gctggtgccg acaccaagtg gtacgagatc     840
ttcggacctg ctctgttgcg ccgcacctt atcggtatca ttcttcagtc tggccagcag     900
cttactggtg ccaacttctt cttctactac ggaaccacga tttcaaggc tactggtctt     960
agcgactctt acgttaccca gatcattctt ggttccgtca acgctggatg cactgttgct    1020
ggtctctggg ttgtcaagaa tgttggccgc cgtaaggccc tcatcggtgg tgccctctgg    1080
atgaccatgt gcttcttggt ctactctttc gtcggaagat tgtgctcga ccccgtcaac    1140
ccggctagca ctcctcaggc cggcaacgtc ctcattgtct ctcctgctt cttcatcgtc    1200
gcctttgcca ccacttgggg tcctctcgtc tgggccgtcg ttgctgagct ctaccctgct    1260
cgctaccgtg ctcctgccat ggccttggcc accgcttcca actggctgtg gaacttcctc    1320
atgtccctct tcacgcgccc catcaccgac tccattggct acttctatgg cttggtgttc    1380
gccggatgct gccttgccct cgccgctttc gtttggctct ttgtgatcga gtccaaggac    1440
cgcacccttg aggagatcga gaccatgtac aaccagaagg tcagcccctag cactccaccc    1500
cactggcacg ctgaggtccc ttcgggaccg cgggatgcgg aggagaagcc cgaggttcac    1560
agtggttctg cgacaacctc aagccatgga gaggtttag                            1599
```

<210> SEQ ID NO 96
<211> LENGTH: 532
<212> TYPE: PRT
<213> ORGANISM: Neurospora crassa

<400> SEQUENCE: 96

```
Met Gly Leu Phe Ser Lys Lys Ser Ala Ala Pro Gln Thr Gln Ser Gln
  1               5                  10                  15

Asp Glu Ile Asp Leu Ala Ala Glu Gln Lys Val Thr Phe Arg Ala Val
             20                  25                  30

Phe Leu Gly Val Val Ala Ser Val Gly Gly Phe Met Phe Gly Tyr Val
         35                  40                  45

Ser Gly Gln Ile Ser Gly Phe Phe Asp Met Glu Asp Phe Gly Arg Arg
     50                  55                  60
```

```
Phe Gly Asn Tyr Gln Asp Ala Asp Gly Trp Val Phe Ser Ala Tyr Arg
 65                  70                  75                  80

Gln Gly Ala Ile Val Ala Leu Leu Pro Ala Gly Ala Leu Leu Gly Ser
                 85                  90                  95

Leu Val Ala Gly Arg Ile Ala Asp Thr Leu Gly Arg Arg Ile Ala Ile
            100                 105                 110

Ser Ala Ser Ala Leu Phe Ser Cys Ile Gly Thr Ile Glu Ile Ala
        115                 120                 125

Ser Thr Thr His Trp Ala Gln Phe Ala Val Gly Arg Leu Ile Thr Gly
        130                 135                 140

Ile Gly Ile Gly Ala Leu Ser Val Val Val Pro Met Tyr Gln Ser Glu
145                 150                 155                 160

Ser Ala Pro Ala Ile Leu Arg Gly Ile Leu Val Ser Cys Tyr Gln Leu
                165                 170                 175

Phe Ile Thr Leu Gly Ile Trp Thr Ala Glu Met Ile Asn Tyr Gly Thr
                180                 185                 190

His Asp Leu Ser Asn Ser Ala Ser Trp Arg Ile Pro Asn Gly Ile Ser
                195                 200                 205

Phe Leu Trp Ala Leu Val Leu Gly Gly Ile Leu Phe Leu Pro Glu
210                 215                 220

Ser Pro Arg Tyr Ala Tyr Arg Val Gly Arg Glu Asp Glu Ala Arg Asn
225                 230                 235                 240

Thr Ile Ala Arg Leu Ala Gly Leu Glu Pro Ser Ala Arg Ser Val Asn
                245                 250                 255

Met Gln Ile Asp Glu Ile Arg Met Lys Leu Glu Glu Lys Ala Gly
        260                 265                 270

Ala Asp Thr Lys Trp Tyr Glu Ile Phe Gly Pro Ala Leu Leu Arg Arg
        275                 280                 285

Thr Leu Ile Gly Ile Ile Leu Gln Ser Gly Gln Gln Leu Thr Gly Ala
290                 295                 300

Asn Phe Phe Phe Tyr Tyr Gly Thr Thr Ile Phe Lys Ala Thr Gly Leu
305                 310                 315                 320

Ser Asp Ser Tyr Val Thr Gln Ile Ile Leu Gly Ser Val Asn Ala Gly
                325                 330                 335

Cys Thr Val Ala Gly Leu Trp Val Val Lys Asn Val Gly Arg Arg Lys
            340                 345                 350

Ala Leu Ile Gly Gly Ala Leu Trp Met Thr Met Cys Phe Leu Val Tyr
        355                 360                 365

Ser Phe Val Gly Arg Phe Val Leu Asp Pro Val Asn Pro Ala Ser Thr
370                 375                 380

Pro Gln Ala Gly Asn Val Leu Ile Val Phe Ser Cys Phe Phe Ile Val
385                 390                 395                 400

Ala Phe Ala Thr Thr Trp Gly Pro Leu Val Trp Ala Val Ala Glu
                405                 410                 415

Leu Tyr Pro Ala Arg Tyr Arg Ala Pro Ala Met Ala Leu Ala Thr Ala
                420                 425                 430

Ser Asn Trp Leu Trp Asn Phe Leu Met Ser Leu Phe Thr Arg Pro Ile
        435                 440                 445

Thr Asp Ser Ile Gly Tyr Phe Tyr Gly Leu Val Phe Ala Gly Cys Cys
        450                 455                 460

Leu Ala Leu Ala Ala Phe Val Trp Leu Phe Val Ile Glu Ser Lys Asp
465                 470                 475                 480

Arg Thr Leu Glu Glu Ile Glu Thr Met Tyr Asn Gln Lys Val Ser Pro
```

-continued

```
                485                 490                 495
Arg His Ser Thr His Trp His Ala Glu Val Pro Ser Gly Pro Arg Asp
            500                 505                 510

Ala Glu Glu Lys Pro Glu Val His Ser Gly Ser Ala Thr Thr Ser Ser
            515                 520                 525

His Gly Glu Val
    530
```

DIBASIC ORGANIC ACID PRODUCING STRAIN AND PREPARATION AND APPLICATION OF SAME

TECHNICAL FIELD

The present invention relates to the field of biotechnology and bioengineering. In particular, the present invention relates to a new engineered bacterium producing dibasic organic acid, and a method for preparing dibasic organic acid by using the same.

BACKGROUND

In view of the rapid growth in the demand for petroleum-based chemicals or fuels and their increasing costs, and considering the impact of geopolitical instability on crude oil prices and the impact of greenhouse gas emissions on global climate, there is an urgent need to develop a new green process with renewable and sustainable properties to produce these petroleum-based chemicals or fuels. These factors have greatly contributed to the research of using enormous biomass to produce chemicals or fuels, especially using non-food renewable resources as raw materials (second-generation biorefinery).

At present, the common process for biomass utilization is divided into three steps: biomass pretreatment, enzymatic hydrolysis and fermentation, wherein the pretreatment still requires high energy consumption and high pollution processes such as high temperature, high pressure, or acid and alkali treatment. In addition, although the yield of cellulolytic enzymes production has reached above the level of 100 g/L, but the application of cellulase in enzymolysis costs too much, and takes a large proportion in the whole process costs, which does not meet the basic requirements of industrial production in large scale. In the practical application, the production process of biomass-based products is greener, more sustainable, and more in line with the trend of modern industrial development, but its production costs are much higher than that of petroleum-based products. The development of bio-refining industry is seriously restricted with the economic factors.

DL-malic acid, the product of malic acid as an example of organic dicarboxylic acid, is traditionally completed by chemical catalytic synthesis based on petroleum-based materials, and it's application is limited in the medicine and food industry because L-malic acid needs to be obtained through optical resolution. The production of single optically active L-malic acid by microbial fermentation draws great concerns and attention.

At present, there are still a lot of problems for malic acid fermentation, for example, the temperature for malic acid fermentation is low, therefore the fermentation reaction needs to be continued after cooling down due to the excessive heat produced during the conventional fermentation process. This not only restricted the fermentation efficiency, but also wasted energy. For another example, the cost is higher due to the substrate of glucose, while malic acid with a production level can not be obtained by cheap substrate.

Therefore, there is an urgent need to develop a method for producing an organic binary acid, especially malic acid, effectively using cheap substrates.

SUMMARY OF THE INVENTION

The invention provides a new engineered strain for synthesizing a dibasic organic acid in high yield, and a preparation method and an application thereof.

In the first aspect, the invention provides an engineered strain with genetic modification for synthesizing a dibasic organic acid, which introduces or up-regulates the expression of a positive regulator gene for a dibasic organic acid synthesis (preferably introduces an exogenous positive regulator gene), and/or down-regulates expression of a negative regulator gene of a dibasic organic acid synthesis, and as compared with the origin strain of the engineered strain, the capability for producing the dibasic organic acid is significantly improved, wherein, the dibasic organic acids comprise malic acid, succinic acid, fumaric acid, oxaloacetic acid, glutaric acid, or adipic acid.

In another preferred example, the dibasic organic acid is malic acid.

In another preferred embodiment, the dibasic organic acid is a C4-C6 dibasic acid.

In another preferred example, the producing capacity of the dibasic organic acid is industrial grade.

In another preferred embodiment, the original strain of the engineered strains comprises *Myceliophthora* strains, *Thielavia*, *Aspergillus* or *Rhizopus*; preferably, *Myceliophthora* comprises *Myceliophthora thermophila* or *Myceliophthora heterothallica*; and *Myceliophthora thermophila* is preferred; *Thielavia* comprises *Thielavia terrestris*; *Aspergillus* comprises *Aspergillus oryzae*, *Aspergillus flavus*, *Aspergillus sojae*; *Rhizopus* comprises *Rhizopus oryzae* Went et Pr.Geerl.

In another preferred embodiment, among the original strain genomes, each corresponding positive and/or negative regulator gene of dibasic organic acid synthesis has at least 92%, preferably at least 95%, preferably at least 98%, 99% of homology.

In another preferred embodiment, the term "significantly improve" means that compared to the original strain, the engineered strain provides a yield of dibasic organic acid fermentation at least more than 10 g/L, preferably at least 10-50 g/L; more preferably at least 50-300 g/L of the based on the volume of the fermentation liquid; and/or the term "significantly improve" means that compared to the original strain, the engineered strain increases or improves the dibasic organic acid producing capacity by a at least 10%; preferably at least 10-50%; more preferably at least 50%-500%. In another preferred embodiment, the expression product of the positive regulator gene comprises one or more polypeptides or the derivative polypeptides thereof selected from the group consisting of aspartate aminotransferase, glutamate-aspartate transporter, and glucose transporter; and/or the expression product of the negative regulator gene comprises one or more polypeptides or derived polypeptides thereof selected from the group consisting of Succinyl-CoA synthase, and Malic acid-alpha ketoglutarate transporter.

In another preferred embodiment, the aspartate aminotransferase is as set forth by SEQ ID NO.: 4.

In another preferred embodiment, the glutamate aspartate transporter is as set forth by SEQ ID NO.: 6.

In another preferred example, the malate dehydrogenase is as set forth by SEQ ID NO.: 10.

In another preferred example, the glucose transporter is as set forth by SEQ ID NO.: 96.

In another preferred example, the succinyl-CoA synthase is as set forth by SEQ ID NO.: 2.

In another preferred example, the malic acid-alpha ketoglutarate transporter is as set forth by SEQ ID NO.: 8.

In another preferred embodiment, an exogenous positive regulator gene for synthesizing the dibasic organic acid is introduced into the engineered strain, and the negative regulator gene of which for synthesizing the dibasic organic acid is simultaneously down regulated.

In another preferred embodiment, the expression product of the positive regulator gene also comprises one or more polypeptides or their derivative peptides selected from the group consisting of C4-dicarboxylic acid transporter, pyruvate carboxylase, malate dehydrogenase, glucose transporter and the combinations thereof.

In another preferred embodiment, the engineering strains are obtained by the following methods:

introducing a positive regulatory gene for synthesizing the dibasic organic acid into an original strain (preferably introducing an exogenous positive regulatory gene) or up-regulating the expression of a positive regulatory gene for synthesizing the dibasic organic acid in an original strain; or down-regulating the expression of a negative regulatory gene for synthesizing the dibasic organic acid in an original strain.

In another preferred embodiment, the polypeptides or the derived polypeptides thereof are selected from the group consisting of (I) one or more sequences of SEQ ID NO.: 2, 4, 6, 8, 10, 12, 14, 16, 18, 20, 22, 26, or 96;

(II) one or more polypeptides derived from (I) by one or several amino acids deleted, added or substituted from the sequence of SEQ ID NO.: 2, 4, 6, 8, 10, 12, 14, 16, 18, 20, 22, 26 or 96, and enabling the engineered strain to have a capacity for producing dibasic organic acid; and (III) one or more polypeptides that have an amino acid sequence having an identity of ≥90% (preferably ≥95%, more preferably ≥98%) with the sequence of SEQ ID NO.: 2, 4, 6, 8, 10, 12, 14, 16, 18, 20, 22, 26, or 96 and enabling the engineered strain to have a capacity for producing dibasic organic acid.

In another preferred embodiment, a polynucleotide sequence encoding the polypeptide or its derived polypeptide comprises:

(i) a polynucleotide encoding a sequence of SEQ ID NO.: 2, 4, 6, 8, 10, 12, 14, 16, 18, 20, 22, 26, 28, 30, or 96;

(ii) a polynucleotide having a sequence of SEQ ID NO.: 1, 3, 5, 7, 9, 11, 13, 15, 17, 19, 21, 25, or 95;

(iii) a polynucleotide sequence having an identity of ≥95% (preferably ≥98%) with a sequence of SEQ ID NO.: 1, 3, 5, 7, 9, 11, 13, 15, 17, 19, 21, 25, or 95; or (iv) a polynucleotide derived from SEQ ID NO.: 1, 3, 5, 7, 9, 11, 13, 15, 17, 19, 21, 25, or 95 by 1-60 (preferably 1-30, more preferably 1-10) nucleotides deleted or added at 5' end and/or 3' end;

(v) a polynucleotide complementary to any one of the sequence of (I)-(IV).

In another preferred embodiment, in the engineered strain with up-regulated expression or introduction of an exogenous positive regulatory gene for synthesizing the dibasic organic acid, compared to the original strain (wild type), the expression of the positive regulator gene is improved by at least 50%, preferably at least 60%, 70%, 80%, 90%, or 100%.

In another preferred embodiment, in the engineered strain with down-regulated expression of a negative regulatory gene for synthesizing the dibasic organic acid, compared to the original strain (wild type), the expression of the negative regulator gene is decreased by at least 50%, preferably at least 60%, 70%, 80%, 90%, or 100%.

In the second aspect of the invention, a method for preparing a dibasic organic acid is provided, comprising steps of:

(i) providing the engineered strain described in the first aspect of the invention;

(ii) in the presence of a substrate, culturing the engineered strain described in (i), thereby obtaining a fermentation product containing a dibasic organic acid; and optionally (iii) isolating and purifying the fermentation product obtained in (ii) thereby further obtaining the dibasic organic acid.

In another preferred embodiment, the substrate comprises monosaccharide(s), polysaccharide(s), glycan(s), biomass, or combinations thereof.

In another preferred embodiment, the polysaccharide comprises sucrose, maltose, cellobiose, fibrous oligosaccharides, xylobiose, xylosaccharides or combinations thereof.

In another preferred embodiment, the monosaccharide comprises glucose, xylose, arabinose, or combinations thereof.

In another preferred embodiment, the glycan comprises cellulose, crystalline cellulose, hemicellulose, starch or combinations thereof.

In another preferred embodiment, the culture temperature of the engineered strain is 25-60° C., preferably 40-55° C., more preferably 45-50° C.

In the third aspect of the invention, a method is provided for preparing the engineered strain of the first aspect of the invention, and/or giving a capacity to a *Myceliophthora* strain or enhancing the capacity of a *Myceliophthora* strain for producing a dibasic organic acid, comprising steps of:

introducing or up-regulating the expression of a positive regulatory gene for synthesizing the dibasic organic acid (preferably introducing an exogenous positive regulatory gene) in an original strain; and/or down-regulating the expression of a negative regulatory gene for synthesizing the dibasic organic acid in an original strain, thereby preparing an engineered strain of the first aspect of the invention and/or allowing *Myceliophthora* strain to synthesize the dibasic organic acid.

In another preferred embodiment, the method comprises steps of:

(a1) providing an expression vector carrying an exogenous positive regulatory gene for synthesizing the dibasic organic acid;

(b1) transferring the expression vector into host cells;

(c1) culturing the host cells; and/or the method comprises steps of:

(a2) knocking out the negative regulatory gene for synthesizing the dibasic organic acid in host cells;

(b2) culturing the host cells.

In the fourth aspect of the invention, combinations of expression products of a dibasic organic acid producing regulatory gene are provided, comprising at least two polypeptides selected from the group consisting of:

(Ia) a sequence of SEQ ID NO.: 4, 6, 10 or combinations thereof;

(IIa) polypeptides which are derived from (Ia) by one or more amino acids deleted, added or substituted from the sequence of SEQ ID NO.: 4, 6, or 10 and enable *Myceliophthora* strains to have a capacity and/or enhance the capacity for producing dibasic organic acid and (Ib) the sequences of SEQ ID NO.: 12, 14, 16, 18, 20, 22, 26, 28, 30, or 96 or combinations thereof; and (IIb) polypeptides which are derived from (Ib) by one or more amino acids deleted, added or substituted from the sequence of SEQ ID NO.: 12, 14, 16, 18, 20, 22, 26, 28, 30, or 96 and enable *Myceliophthora* strains to have a capacity for producing dibasic organic acid and/or enhance the capacity for producing dibasic organic acid and In another preferred embodiment, the combination comprises at least the sequences of SEQ ID NO.: 4 and 6.

In another preferred embodiment, the combination comprises at least the sequences of SEQ ID NO.: 6 and 10.

In another preferred embodiment, the combination comprises at least the sequences of SEQ ID NO.: 4 and 10.

The fifth aspect of the invention provides a combination of the dibasic organic acid producing regulatory genes, which comprises at least two kinds of polynucleotides that encode the expression product in the combination of expression products of the fourth aspect of the invention.

In the sixth aspect of the invention provides a carrier comprising the combination of the fifth aspect of the invention, and/or containing an inhibitor that inhibits the negative regulator gene of the dibasic organic acid production.

In another preferred embodiment, the inhibitor is an interference RNA or antisense nucleic acid of the negative regulator gene (such as Succinyl-CoA synthase) of a dibasic organic acid production.

In another preferred embodiment, the sequence of the interfering RNA is as set forth by SEQ ID NO.: 74 or 75.

In another preferred embodiment, there are one or more carriers.

In the seventh aspect of the invention, a host cell is provided that has characteristics selected from the group consisting of:

(a1) containing the carrier of the first aspect of the invention;

(b1) the chromosomes of the host cells are artificially integrated with the polynucleotide that encodes the polypeptide of SEQ ID NO.: 4, 6, 10, or 96 or the expression of the original gene encoding said polypeptide is up-regulated; or the gene encoding the polypeptide of SEQ ID NO.: 2 and/or 8 in the chromosome of the host cell is knocked out or weakened; and optionally the chromosomes of the host cells are integrated with one or more polynucleotide(s) selected from the polypeptides of SEQ ID NO.: 4, 6, 10, 12, 14, 16, 18, 20, 22, 26, and 96.

In another preferred embodiment, the host cell is the engineered strain of the first aspect of the invention.

In another preferred embodiment, the host cell is *Myceliophthora* strain, preferably *Myceliophthora thermophila*.

The eighth aspect of the invention, a use of the combination of the forth aspect of the invention is provided for preparing the engineered strain of the first aspect of the invention, and/or giving a capacity to *Myceliophthora* strain or enhancing the capacity of *Myceliophthora* strain for producing dibasic organic acid.

In another preferred embodiment, said "giving" or "enhancing" the capacity for producing dibasic organic acid refers to that after reconstruction the strain originally having no capability for producing and/or accumulating dibasic organic acid ability has a capacity for industrially producing dibasic organic acid, and/or the strain originally having poor capability for producing and/or accumulating dibasic organic acid has an enhanced capacity for industrially producing dibasic organic acid.

In the ninth aspect of the invention, an engineered strain with genetic modification for synthesizing the dibasic organic acid is provided, said engineered strain allows the dibasic organic acid to be obtained in a fermentation temperature of 25-60° C. by using glycan and/or biomass as a fermentation substrate, wherein the original strain of the engineered strain is *Myceliophthora*;

and the dibasic organic acid comprises malic acid, succinic acid or fumaric acid.

In another preferred embodiment, the dibasic acid also comprises oxaloacetic acid, glutaric acid, or adipic acid.

In another preferred embodiment, the substrate comprises monosaccharides, polysaccharides, or the combinations thereof.

In another preferred embodiment, the engineered strain is artificially integrated with the positive regulatory gene for synthesizing the dibasic organic acid or up-regulates the expression of the positive regulatory gene for synthesizing the dibasic organic acid, and/or expresses down-regulatedly the negative regulatory gene of the dibasic organic acid synthesis, and compared with the original strain, the capacity of the engineered strain for producing dibasic organic acid is significantly improved.

In another preferred embodiment, the glycan comprises cellulose, crystalline cellulose, hemicellulose, starch (preferably corn, cassava, wheat) or combinations thereof.

The biomass comprises crop straw, forestry waste, papermaking industry waste, cotton textile industry waste, energy plant or part or all of its decomposition products; wherein the crop straw comprises corn straw, wheat straw, rice straw, sorghum straw, soybean straw, cotton straw, bagasse, or corncob; the forestry waste comprised branches, leaves, or sawdust; the papermaking industry waste comprises pulp slag, pulp waste; the cotton textile industry waste comprises wasten cotton and cotton textiles; the energy plants comprises sweet sorghum, switchgrass, *miscanthus*, reed or combinations thereof.

In another preferred embodiment, the substrate only comprises glycans and/or biomass.

In another preferred embodiment, the fermentation temperature is 40-55° C., preferably 45-53° C., more preferably 48-50° C.

In another preferred embodiment, the dibasic organic acid is malic acid.

In another preferred embodiment, the dibasic organic acid is a C4-C6 dibasic acid.

In another preferred embodiment, the producing capacity of the dibasic organic acid is industrial grade.

In the tenth aspect of the invention, a method for preparing a dibasic organic acid is provided, comprising steps of:

(i) providing the engineered strain of the ninth aspect of the invention;

(ii) in the presence of a substrate, culturing the engineered strain of (i), thereby obtaining a fermentation product containing dibasic organic acid, wherein the fermentation temperature is 25-60° C.; and optionally (iii) isolating and purifying the fermentation product obtained in (ii) thereby further obtaining the dibasic organic acid;

wherein, the substrate comprises glycans and/or biomass.

In another preferred embodiment, the culture temperature of the engineered strain is 40-55° C., preferably 45-52° C., more preferably 48-50° C.

In another preferred embodiment, the substrate is cellulose, hemicellulose, starch, or biomass.

In another preferred embodiment, the substrate further comprises monosaccharides, polysaccharides, or combinations thereof.

In another preferred embodiment, the polysaccharide comprises sucrose, maltose, cellobiose, fibrous oligosaccharides, xylobiose, xylosaccharides or combinations thereof.

In another preferred embodiment, the monosaccharide comprises glucose, xylose, arabinose, or combinations thereof.

In the present invention, the producing capacity comprises, but is not limited to, the fermentation product concentration (titer), and/or conversion (yield), and/or the fermentation yield (productivity).

It should be understand that within the scope of the invention each of the technical features described in detail above and below (such as the examples) can be combined with each other separately, so as to form a new or preferred technical proposal, which will no longer be described herein due to the length limitation.

DETAILED DESCRIPTION OF THE INVENTION

Figure 1:
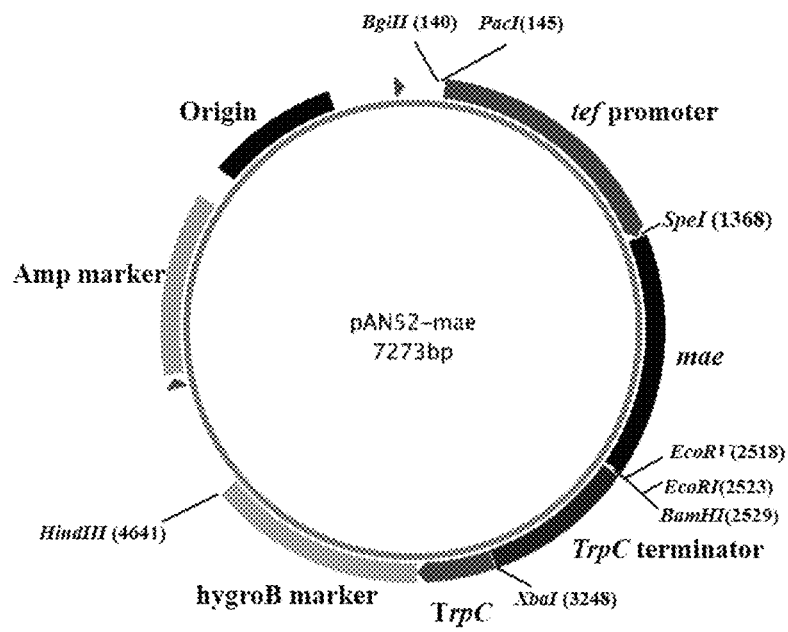
FIG. 1 shows a physical map of the mae gene expression vector pAN52-mae.

After extensive and thorough research, the inventors firstly and surprisingly discover a set of regulatory genes for producing or synthesizing a dibasic organic acid in filamentous fungi strains, especially *Myceliophthora* strains (such as *Myceliophthora* thermophilic), wherein, genes having a function of positive regulation comprise aspartate aminotransferase, glutamic acid-aspartate transporter, malate dehydrogenase, C4-dicarboxylic acid transporter, pyruvate carboxylase, glucose transporter, or combinations thereof, genes having a function of negative regulation comprise succinyl-CoA synthase, malic acid-alpha ketoglutarate transporter, or combinations thereof. It has been confirmed by the inventors that by up-regulation of one or more of the positive regulator genes and\or down-regulation of one or more of the negative regulator genes, the genetic modified engineered strain can effectively use monosaccharide, polysaccharide, glycans or mixed sugars, especially cheap polysaccharide (such as cellulose, etc.) to synthesize dibasic organic acid in high yield under high temperature conditions. In addition, the inventors also have confirmed by experiments that the regulatory function has relative strain species specificity. On this basis, the invention is completed.

Dibasic Organic Acid

As used herein, the term "dibasic organic acid" refers to organic acids in which each molecule can ionize two and only two hydrogen ions in water. The dibasic organic acid which can be used herein comprises C4-C6 dibasic organic acid, preferably C4-C5 dibasic organic acid, such as malic acid, succinic acid, fumaric acid, oxaloacetic acid, glutaric acid, or adipic acid. Preferably, the dibasic organic acid of the invention comprises malic acid or succinic acid.

Taking Malic acid for an example, L-malic acid is an important natural organic acid, and widely used in food, beverages, spices, healthcare, chemicals, plastics and other industries. In the food industry, L-malic acid can be used as an acidity regulator, a food preservative, a food deodorant, or a pasta enhancer; and in the pharmaceutical industry, L-malic acid can be added in drug injections, preparations, tablets, or syrups for helping to improve the utilization rate of the medicine. In the daily chemical industry, it can be used as an ingredient of deodorants and detergents. Malic acid has an important position and plays an important role in the organic acid industry. In recent years, the demand for malic acid in the international market increases rapidly, and the market prospect is bright.

Traditionally, the production of malic acid is completed by chemical catalytic synthesis based on petroleum-based materials, and the product is DL-malic acid which limits its application in medicine and food industry because L-malic acid needs to be obtained through optical resolution. The production of L-malic acid with single optical rotation by microbial fermentation has been widely concerned and highly valued.

In addition, the inventors have found that not only the malic acid (and even organic acid) fermentation in *Myceliophthora* can be enhanced through regulating multiple new genes, but also the organic acid producing capacity of strains (including *Aspergillus* (preferably *Aspergillus oryzae*, *Aspergillus sojae*, *Aspergillus terreus*, *Aspergillus niger*), *Rhizopus* (preferably *Rhizopus oryzae*), beside the *Myceliophthora* with accumulation ability) can be improved by genetic modification.

"a capacity for producing organic acid" herein refers to the industrialized capacity for producing organic acid, which is equivalent to the term of "industrial production level", "industrialized potential", "industrial producing capacity", or "organic acid producing capacity", which can be used interchangeably, and refers to the total volume of fermentation liquid, the fermentation yield is at least 10 g/L, preferably at least 15-40 g/L, more preferably, at least 50-300 g/L, and any integer and non-integer in this range, which is no longer listed one by one.

For the fermentation of malic acid and other organic acids, the traditional dominant strain is *aspergillus* strain. In addition, some traditional dominant strains of organic acids include but not limited to: Citric acid-*Aspergillus niger*, Malic acid-*Aspergillus flavus*, *Aspergillus oryzae*, or Lactic acid-*Rhizopus oryzae*. But *Myceliophthora* does not belong to common strains which accumulating organic acids. The invention has shown that for strains (such as *Neurospora crassa*, *Trichoderma reesei*) that have few accumulation of organic acids (usually no more than the grade of gram/liter) in natural conditions, the modification of the synthesizing rout of organic acids (such as malic acid) will not effectively improve their producing yield to industrial level (10 g/l or more), but in the case of strains that did not accumulate organic acids, i.e *Myceliophthora* strains (*Myceliophthora thermophila*, *Myceliophthora heterothallica*), the capacity for synthesizing organic acid (malic acid) was significantly improved (10 g/l or more) by genetic modification, which is very surprising.

Substrate

As used herein, the term "substrate" refers to carbohydrates that can produce a dibasic organic acid in the presence of filamentous fungi, including monosaccharides, polysaccharides, glycans, biomass or a combination thereof, wherein the term "monosaccharide" includes but not limited to glucose, xylose, Arabia sugar or a combination thereof;

"polysaccharide" includes but not limited to sucrose, cellobiose, cello-oligosaccharides, xylobiose, xylo-oligosaccharides or a combination thereof, wherein the "glycans" includes but not limited to cellulose (especially cellulose from biomass source), hemicellulose, or its combination; biomass includes but not limited to crop straw, forestry waste, paper-making industry waste, energy plant, or a combination thereof. Examples of preferred substrates are described below:

Glucose, xylose, and Arabia sugar are three important monosaccharides. Glucose (chemical formula is $C_6H_{12}O_6$) is also known as corn glucose, corn sugar, referred to as glucose, is one of the most widely distributed and most important monosaccharides in nature. Glucose plays an important role in biology field. It is the energy source and metabolic intermediate product of living cells, that is, the main energy supply of biological substances. It has been widely used in confectionery manufacturing and medicine field. It can be largely prepared in industry by using corn, cassava, etc. as raw materials.

Xylose is a five carbon pentose and is the main monosaccharide that makes up hemicellulose, therefore, xylose also widely exists in abandoned parts of agricultural products such as corn cob, straw, the skin of cotton boll and others. It can be obtained by hydrolysis from hemicellulose in biomass.

Arabia sugar, also called pectose, often exists in the form of heteropolysaccharide in combined with other monosaccharides. Arabia sugar exists in the *cereale* such as cornmeal, corncob, rice, wheat etc. and in hemicelluloses and pectic substances in the cell walls of the plants such as beet, apple and others. Xylose and arabinose are the most important five carbon sugars obtained after the degradation or pretreatment of biomass. Microorganisms are usually difficult to be used, which is the difficulty in utilizing whole sugar of biomass.

Sucrose, cellobiose and xylobiose are three important disaccharides. Sucrose is the main product of photosynthesis, and widely distributed in plants, especially in sugar beet, sugar cane and fruit, in which the content is extremely high. Sucrose is a disaccharide which is formed by dehydration condensation of one molecule of glucose and one molecule of fructose and widely used in the biological fermentation industry. It is the raw material of various products such as alcohol, citric acid, lactic acid, glycerol, alcohol, medicine and others. Whereas the cellulose is composed of cellobiose, which can be degraded from cellulose further hydrolyzed into two molecules of glucose. Xylobiose is a xylo-oligosaccharide formed by two xylose through beta-1,4-glycosidic bond, and is a linear disaccharide. It can be obtained by hydrolysis of hemicellulose and can further be decomposed into two xyloses.

Cello-oligosaccharides and xylosaccharides are two important oligosaccharides. Cello-oligosaccharides usually refer to oligosaccharides produced by glucose through the linkage of beta-1, 4 glycosidic bonds. Xylosaccharides, also known as xylo oligosaccharides, are oligosaccharides formed by 2-7 of D-xylose through the linkage of beta-1, 4-glycosidic bonds, and some may also contain arabinose, glucuronic acid and other side chains. Xylobioses, xylosaccharides, cello-oligosaccharides and cellobioses are the main products of cellulose and hemicellulose in plant cellulose (corn cob, bagasse, straw, etc.) through hydrolysis.

Biomass mainly contains cellulose, hemicellulose and lignin. All kinds of crop and energy plant straws (corn straw, wheat straw, rice straw, sorghum straw, bagasse, miscanthus etc.), forestry wastes (sawdust, branches and leaves), paper-making industry waste and so on are important biomass resources. Under certain conditions, they can be degraded into glycans (such as xylan, glucan), oligosaccharides and monosaccharides which can be used by some microbial fermentation. Developing the use of available biomass hydrolysates or even the biomass after simple pretreatment as a carbon source to produce chemical products (ethanol, organic acids, etc.) through fermentation is an important research at home and abroad.

The Dibasic Organic Acid Synthesis Regulatory Gene and its Expression Product

As used herein, the term "the dibasic organic acid synthesis regulatory gene" and "the polynucleotides that encode the polypeptides of the invention" can be used interchangeably, and includes "the positive regulatory gene and the negative regulator gene for synthesizing the dibasic organic acid". Wherein the terms "positive regulatory gene for synthesizing the dibasic organic acid", "positive regulatory gene" and "overexpressing gene" can be used interchangeably and refer to one or more positive genes capable of promoting or enhancing the synthesis of the dibasic organic acids in filamentous fungi (e.g., *Myceliophthora, Aspergillus oryzae, Aspergillus sojae, Aspergillus terreus*, etc.); the terms "negative regulatory gene for synthesizing the dibasic organic acid" and "the negative regulatory gene" refer to one or more negative genes capable of inhibiting or reducing the synthesis of the dibasic organic acids in filamentous fungi; the terms "introduction" and "artificial integration" can be used interchangeably, and the introduced gene can be exogenous and endogenous; wherein, after genetic modification, the highly expressed or overexpressed positive regulator gene or the lowly expressed or knocked out negative regulator gene can make the modified strain has significantly improved capacity for producing dibasic organic acid compared with its original strain.

Preferably, the expression product of the positive regulatory gene comprises one or more polypeptides of the invention or their derived polypeptides selected from the group consisting of aspartate aminotransferase, glutamic acid-aspartate transporter, C4-dicarboxylic acid transporter, malate dehydrogenase, pyruvate carboxylase, and glucose transporter. The expression product of the negative regulatory gene includes one or more polypeptides of the invention or their derived polypeptides selected from the group consisting of succinyl-CoA synthase, and malic acid-alpha ketoglutarate transporter.

More preferably, the polypeptides of the invention or their derived polypeptides are selected from the group consisting of (I) sequences of SEQ ID NO.: 2, 4, 6, 8, 10, 12, 14, 16, 18, 20, 22, 26, or 96;

(II) polypeptides which are derived from (I) by one or more amino acids deleted, added or substituted from the sequence of SEQ ID NO.: 2, 4, 6, 8, 10, 12, 14, 16, 18, 20, 22, 26 or 96 and enable the engineered strain to have the capacity for producing dibasic organic acid; and (III) polypeptides that have an amino acid sequence having a identity of ≥90% (preferably ≥95%, more preferably ≥98%) with the sequence of SEQ ID NO.: 2, 4, 6, 8, 10, 12, 14, 16, 18, 20, 22, 26, or 96 and enable the engineered strain to have a capacity for producing dibasic organic acid.

The derived polypeptide comprises a variant of a sequence as set forth by SEQ ID NO., 2, 4, 6, 8, 10, 12, 14, 16, 20, 22 or 96 which can make the original strain have the capacity for synthesizing the dibasic organic acid. These variants include (but not limited to): deletion, insertion and/or substitution of 1-3 (usually 1-2, preferably 1) of amino acids, and addition or deletion of one or more (usually less than 3, preferably less than 2, preferably less than 1) of amino acids at the C terminal and/or N terminal. For example, in this field, the function of proteins is usually not altered by the substitution of amino acids with close or similar properties. Also, for example, the addition or deletion of one or several amino acids at the C terminal and/or N terminal will not usually alter the structure and function of the protein. The terms "fragments", "derivatives" and "analogues" refer to polypeptides that substantially maintain the ability to allow the original strain have the capacity for synthesizing the dibasic organic acid. The polypeptide fragments, derivatives or analogs of the invention may be (i) polypeptides having one or several conservative or non-conservative amino acid residues (preferably conservative amino acid residues) substituted, or (ii) polypeptides having substituent(s) in one or more amino acid residues, or (iii) polypeptides formed by fusing the polypeptide of the invention with another compound, such as a compound that extends the half-life of the polypeptide, or (iv) a polypeptide in which the additional amino acid sequence is fused to the polypeptide sequence (a fusion protein formed by fusion of a leader sequence, a secretory sequence, or a label sequence such as 6His). These fragments, derivatives and analogs are within the scope of what is known to those skilled in the art in light of the teachings herein. A preferred class of active derivatives refers to a polypeptide formed by up to 3, preferably up to 2, more preferably up to 1 of amino acid substituted with amino acids having close or similar property as compared to the amino acid residues of Formula I. These conserved variant polypeptides are preferably produced by the amino acid substitutions according to Table 1.

TABLE 1

| Primary residue | Representative substitution | Preferred substitution |
|---|---|---|
| Ala (A) | Val; Leu, Ile | Val |
| Arg (R) | Lys; Gln; Asn | Lys |
| Asn (N) | Gln, His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn, Gln; Lys; Arg | Arg |
| Ile (I) | Leu, Val; Met; Ala; Phe | Leu |
| Leu (L) | Ile, Val; Met; Ala; Phe | Ile |
| Lys (K) | Arg, Gln, Asn | Arg |
| Met (M) | Leu, Phe, Ile | Leu |
| Phe (F) | Leu, Val; Ile, Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp, Phe, Thr, Ser | Phe |
| Val (V) | Ile, Leu, Met; Phe, Ala | Leu |

In another preferred embodiment, a sequence of a polynucleotide encoding the polypeptide or its derived polypeptide of the invention (the polynucleotide of the invention) comprises:

(i) a polynucleotide encoding a sequence of SEQ ID NO.: 2, 4, 6, 8, 10, 12, 14, 16, 18, 20, 22, 26, 28, 30, or 96;

(ii) a polynucleotide having a sequence of SEQ ID NO.: 1, 3, 5, 7, 9, 11, 13, 15, 17, 19, 21, 25, or 95;

(iii) a polynucleotide sequence having an identity of ≥95% (preferably ≥98%) with a sequence of SEQ ID NO.: 1, 3, 5, 7, 9, 11, 13, 15, 17, 19, 21, 25, or 95; or (iv) a polynucleotide derived from SEQ ID NO.: 1, 3, 5, 7, 9, 11, 13, 15, 17, 19, 21, 25, or 95 by 1-60 (preferably 1-30, more preferably 1-10) nucleotides deleted or added at 5' end and/or 3' end;

(v) a polynucleotide complementary to any one of the sequence of (I)-(IV).

The full-length sequence of the polynucleotide or its fragment of the invention can usually be obtained by PCR amplification, recombination or artificially synthesis. A preferred method to obtain the polynucleotides of the invention generally has the following steps:

(1) transforming or transducing a suitable host cell with a recombinant expression vector of a polynucleotide (or a variant) encoding the polypeptide of the invention, or a recombinant expression vector containing the polynucleotide;

(2) culturing the host cell in suitable medium;

(3) isolating and purifying proteins from the medium or the cell.

The sequences of the polypeptides of the invention and the corresponding encoding polynucleotides are shown in table 2:

TABLE 2

| Name of the Protein (polypeptide of the invention) | source | function | nucleotide sequence (SEQ ID NO.:) | amino acid sequence (SEQ ID NO.:) |
|---|---|---|---|---|
| succinyl-CoA synthase | Myceliophthora thermophila | Negative regulation | 1 | 2 |
| aspartate aminotransferase | Myceliophthora thermophila | Positive regulation | 3 | 4 |
| glutamic acid-aspartate transporter | Myceliophthora thermophila | Positive regulation | 5 | 6 |
| malic acid-alpha ketoglutarate transporter | Myceliophthora thermophila | Negative regulation | 7 | 8 |
| malate dehydrogenase | Myceliophthora thermophila | Positive regulation | 9 | 10 |
| C4-dicarboxylic acid transporter | Aspergillus oryzae | Positive regulation | 11 | 12 |
| C4-dicarboxylic acid transporter | Neurospora crassa | Positive regulation | 13 | 14 |
| C4-dicarboxylic acid transporter | Trichoderma reesei | Positive regulation | 15 | 16 |
| C4-dicarboxylic acid transporter | Myceliophthora thermophila | Positive regulation | 17 | 18 |
| C4-dicarboxylic acid transporter | Aspergillus niger | Positive regulation | 19 | 20 |
| C4-dicarboxylic acid transporter | Aspergillus sojae | Positive regulation | 21 | 22 |
| pyruvate carboxylase | Aspergillus oryzae | Positive regulation | 25 | 26 |
| glucose transporter | Neurospora crassa | Positive regulation | 95 | 96 |

Engineered Strain and Preparation Method Thereof

The terms "Engineering bacteria", "engineered strain" and "genetic modified strain" of the invention can be used interchangeably, referring to the engineered strain in which the positive regulatory gene for synthesizing the dibasic organic acid is introduced or the expression of the positive regulatory gene for synthesizing the dibasic organic acid is up-regulated, and/or the expression of the negative regulatory gene for synthesizing the dibasic organic acid is downregulated. Among them, compared with its original strain, the dibasic organic acid producing capacity of the engineered strain of the invention is significantly improved, wherein the dibasic organic acid comprises malic acid, succinic acid, fumaric acid, oxaloacetic acid, glutaric acid or adipic acid.

The original strain that can be modified to the engineered strain of the invention is usually filamentous fungi, especially filamentous fungi of *Myceliophthora*, such as *Myceliophthora thermophila, Myceliophthora heterothallica*, preferably *Myceliophthora thermophila*. The wild original strain usually does not have the capacity to synthesize the dibasic organic acid, or does not have the capacity for producing dibasic organic acid of an amount required in industry. Normally, an original strain in which a dibasic organic acid can be produced in the natural state, but will be rapidly converted into downstream metabolites (i.e., no accumulation of a dibasic organic acid can be formed) is also within the scope of the original strain of the invention. After genetic modification, the capacity for producing dibasic organic acid of the engineered strain of the invention is significantly improved, and the term "significantly improve" includes the strain that originally has no capacity for synthesizing the dibasic organic acid has that ability, or that ability is substantially increased compared with the original strain. Preferably, the term "significantly improve" means that compared to the original strain the capacity for producing dibasic organic acid of the engineered strain is increased or improved by at least 10%; preferably at least 10-50%; more preferably at least 50%-500%.

In addition, the original strain that can be modified into the engineered strain of the invention can also include *Thielavia*, preferably *Thielavia terrestris; Aspergillus*, preferably *Aspergillus oryzae, Aspergillus flavus, Aspergillus sojae*; and *Rhizopus*.

The engineered bacteria of the invention can be prepared by the following methods:

(a1) providing an expression vector carrying a positive regulatory gene for synthesizing the dibasic organic acid;

(b1) transferring the expression vector into a host cell;

(c1) culturing the host cell; and/or the method comprises steps of:

(a2) knocking out the negative regulatory gene for synthesizing the dibasic organic acid in host cells;

(b2) culturing the host cells;

wherein, the host cell is the original strain.

The negative regulatory gene of the invention can be knocked out or down regulated by genetic engineering means or substances that inhibit the expression and/or activity of the negative regulatory gene so as to obtain a new transgenic engineered bacterium. Such substances are known as "inhibitors of the invention" or "negative regulatory genes inhibitors". The inhibitors, for example, include antibodies inhibitory mRNA, antisense RNA, microRNA (miRNA), siRNA, shRNA to the negative regulatory genes, and activity inhibitors of zinc finger transcription factors. A preferred inhibitor is a negative regulatory gene of siRNA, such as a sequence of SEQ ID NO.: 1. According to the sequence of SEQ ID NO.: 1 of the invention, siRNAs that inhibiting its expression can be designed by conventional techniques in the art, and the preferred siRNAs are shown in SEQ ID NO.: 74 and 75.

Combination of the Regulatory Gene for Producing Dibasic Organic Acid or the Expression Products Thereof The invention also provides a combination of the polypeptides of the invention or their encoding polynucleotides.

The experiment has proved that it can effectively improve the capacity of the strain for producing dibasic organic acid by using the combination of the invention to modify the original strain simultaneously. Wherein the combination of the regulatory gene expression products of the invention may include at least two polypeptides selected from the group consisting of (Ia) a sequence of SEQ ID NO.: 4, 6, or 10 or combinations thereof; or (IIa) a polypeptide derived from (Ia) by one or more amino acids deleted, added or substituted from the sequence of SEQ ID NO.: 4, 6, or 10 and enabling *Myceliophthora* strains to have the capacity for producing dibasic organic acid and/or increasing the capacity for producing dibasic organic acid; and optional (Ib) a sequence of SEQ ID NO.: 12, 14, 16, 18, 20, 22, 26, 28, 30, 96 or combinations thereof;

(IIb) a polypeptide derived from (Ib) with one or more amino acids deleted, added or substituted from the sequence of SEQ ID NO.: 12, 14, 16, 18, 20, 22, 26, 28, 30, or 96 and enabling *Myceliophthora* strains to have the capacity for producing dibasic organic acid and/or increase the capacity for producing the dibasic organic acid.

While the combination of the dibasic organic acid producing regulatory genes of the invention contains at least two polynucleotides, and the polynucleotides correspondingly encode the polypeptides in the combination of the expression products of the invention, respectively.

In addition, the invention also provides a vector containing the gene combination of the invention, and a host cell comprising the vector or the chromosome with the positive regulator gene for producing the dibasic organic acid intergrated and/or with the negative regulator gene for producing the negative regulator gene down-regulated.

Preferably, the chromosome of the host cell of the invention is artificially integrated with the polynucleotide that encodes the polypeptides of SEQ ID NO.: 4, 6, and/or 10; or the gene that encodes the polypeptides of SEQ ID NO.: 2 and/or 8 in the chromosome of the host cell is knocked out or weakened; and optionally the chromosome of the host cell is integrated with one or more polynucleotides selected from the polypeptides of SEQ ID NO.: 4, 6, 10, 12, 14, 16, 18, 20, 22, 26, and 96.

The Beneficial Effects of the Invention (a) By using a protoplast or an *agrobacterium* mediated transformation/transfection method, a heterologous or homologous nucleic acid sequence is stably introduced into an original strain, said nucleic acid sequence is operably linked to the expression regulatory region, while knocking-out or mutation or attenuated expression and screening for gene and knock out the transformants with the assistance of green fluorescent protein are also included. The genetic operation technique system of *Myceliophthora thermophila* is underdeveloped. The present invention firstly uses the genetic engineering technology to transform *Myceliophthora thermophila* and thereby producing the dicarboxylic acid by fermentation.

(b) A set of new key genes impacting the dicarboxylic acid fermentation level in filamentous fungi are discovered, and the fermentation level of the dicarboxylic acid (especially malic acid) is improved through the genetic modification in *Myceliophthora*, wherein the genes include succinyl-CoA synthase, aspartate aminotransferase, malic acid-alpha ketone glutaric acid transporter, glutamic acid-aspartate transporter and C4-dicarboxylic acid transporter, glucose transporter, or malate dehydrogenase.

(c) Under certain conditions, dibasic acids are produced from the recombinant strains with a variety of carbon sources as fermentation substrates, including biomass resources, which greatly reduces the cost of fermentation of biomass-based chemicals. L-malic acid is directly produced by fermentation of microorganisms (and the production of other dibasic organic acids and even more chemicals are allowed).

(d) The fermentation temperature is high. The fermentation can be conducted at 40-50 degrees (preferably 45 degrees), which significantly save the condensation costs during the fermentation, thereby reducing the cost of the fermentation. The strains of the invention can synthesize the dibasic organic acid with high yield at high temperature which can not be tolerated by the room temperature filamentous fungi (such as *Aspergillus*).

The invention will now be further described with reference to specific embodiments. It should be understood that these examples are merely illustrative of the invention and are not intended to limit the scope of the invention. The experimental methods not specified for conditions in the following examples are generally carried out according to conventional conditions, such as those described in Sambrook et al., Molecular Cloning: Laboratory Manual (New York: Cold Spring Harbor Laboratory Press, 1989), or conditions suggested by the manufacturer. Unless otherwise specified, percentages and parts are those by weight.

Example 1 Overexpressing C4-Dicarboxylic Acid Transporter Encoding Gene Mae in *Myceliophthora thermophila* to Allow *Myceliophthora thermophila* to Obtain a Capacity for Producing Malic Acid 1. Construction of a Vector with Mae Overexpressed (pAN52-mae)

Pan52-TB-Intron (Liu Q, Li J, Ying S, Wang J, Sun W, Tian C, Feng M. 2014. Unveiling equal importance of two 14-3-3 proteins for morphogenesis, condition, stress tolerance and virulence of an insect pathogen. Environ Microbiol. doi: 10.1111/1462-2920.12634) was used as the skeleton to construct the expression vector, wherein the plasmid pCSN44 (available from fungal genetics stock center) was used as a template and Hygromycin phosphotransferase coding gene (hph) was PCR amplified under the regulatory of TrpC promoter according to the guidance of primers. The sequences of the primers are as follows:

```
hph-F (SEQ ID NO.: 23):
GCTCTAGACAGAAGATGATATTGAAGGAGC hph-R (SEQ ID NO.: 24):
CCCAAGCTTCTATTCCTTTGCCCTCGGACGAG
```

The hph.PCR reaction system is:
5× phusion HF buffer 10 µL, 10 mM dNTPs 1 µL, GLT-F 2.5 µL, GLT-R 2.5 µL, cDNA 1 µL, Phusion DNA polymerase 0.5 µL, water 32.5 µL. The PCR reaction conditions are as follows: 98° C. for 30 s at first, then 98° C. for 10 s, 65° C. for 30 s, 72° C. for 1.5 min, 34 cycles, 72° C. for 10 min, and 4° C. for 10 min at last.

After PCR reaction, the gene was digested by XbaI and HindIII and ligated into the linearized vector pAN52-TB-Intron, which was digested by the same enzymes. The ligation product was digested with restriction endonuclease and subjected to sequencing. The sequence result shows that the nucleotide sequence of hph is shown as SEQ ID NO.: 27, which indicates that the recombinant expression plasmid carrying hph gene with correct sequence and insertion cite was obtained and named as pAN52-hph.

C4-dicarboxylic acid transporter encoding gene mae (XM_001820829.2, SEQ ID NO.: 11) was obtained by PCR amplification taking *Aspergillus oryzae* DSM1863 (DSMZ, purchased from German Microorganism and Cell Culture Co., Ltd.) as the template under the guidance of primers, and the gene was digested by BglII and then ligated into linearized vector pAN52-hph which was digested by BglII and EcoRV, the ligation product was digested with restriction endonuclease, and a vector carrying mae gene was obtained and named as pAN52-hph-mae. and the sequences of the primers are as follows:

```
Mae-F: 5' (SEQ ID NO.: 43):
GGAAGATCTTAATTAACTCGAGCGGCCGCGTTTAAACACTAGTATGCTG
ACACCTCCCAAGTTTG

Mae-R: 5' (SEQ ID NO.: 44):
ATCCTAATCAGATACAT CCTCATCTTTA
```

Taking the genes of original strain *Myceliophthora thermophila* ATCC42464 (purchased from American Type Culture Collection) as the template, a promoter of 1.4 kb upstream of translation extension factor encoding reading frame (MYCTH_2298136) (named as Ptef promoter) was amplified by PCR and the sequence of SEQ ID NO.: 28 was amplified using primers, and the sequences of the primers are as follows:

```
Tef-F: (SEQ ID NO.: 29):
CCTTAATTAACATGTACCTTGACGTCCTCCGAG

Tef-R: (SEQ ID NO.: 30):
GGACTAGTTCTGAAGAACGAAACTGGC GACT
```

After PCR reaction, the gene was digested by PacI and SpeI and ligated into the linearized vector pAN52-hph-mae, which was digested by the same enzyme. The ligation product was digested with restriction endonuclease and verified to obtain a mae expression vector under the regulatory of promoter tef which and named as pAN52-mae. The physical spectrum is shown in FIG. 1.

2, Introducing the Expression Vector (pAN52-mae) into *Myceliophthora thermophila*

2.1 *Myceliophthora thermophila* ATCC42464 was cultured in MM slant medium [20 mL of 50×Vogel's salt, 20 g of sucrose, 15 g of agar, and 20 mL of histidine (50 mg/mL) were adjusted to 1 L and sterilized under high pressure. 50×Vogel's salt (1 L): trisodium citrate (1/2$H_2O$) 150 g, anhydrous $KH_2PO_4$ 250 g, anhydrous $NH_4NO_3$ 100 g, $MgSO_4 \cdot 7H_2O$ 10 g, $CaCl_2 \cdot 2H_2O$ 5 g, salt solution of trace elements 5 mL and biotin (0.1 mg/mL) 2.5 mL were adjusted to 1 L] for 10 days at 45° C. to be used.

2.2 Protoplast Transformation of *Myceliophthora thermophila*

1) Preparation of the Mycelium

Mature spores of *Myceliophthora thermophila* was collected with sterilized water containing 0.05% Tween-80. The hyphae was filtered and obtained with the lense paper and then placed on MM plates with cellophane and cultured at 45 for 14 h.

2) Preparation of the Protoplast

The cellophane with mycelium was placed in 30 mL of lysate (formulation: 0.15 g of lyase, and 30 mL of solution A was added aseptically, the product was filtered for sterilization; solution A: 1.0361 g of potassium dihydrogen phosphate and 21.864 g of sorbitol were dissolved in 90 mL of deionized water. Potassium hydroxide was used to adjust the pH to 5.6, and the product was quantified to 100 mL and sterilized at high temperature) and lysed at 28° C. for 2 h and gently shaken every 20 min.

Then the mixture was filtered with cellophane and centrifuged at 4° C. under 2000 rpm for 10 min. The supernatant was discarded. To the remain was added 4 mL of solution B (0.735 g of calcium chloride, 18.22 g of sorbitol and 1 mL of Tris-HCl 1M pH 7.5 was dissolved in 90 mL of deionized water. Hydrochloric acid was used to adjusted the pH to 7.6, and the product was quantified to 100 mL and sterilized at high temperature). The mixture was centrifuged at 4° C. under 2000 rpm for 10 min. The supernatant was discarded. A certain volume of solution B was added as 200 L/plasmid.

3) Transformation of Protoplast

To the pre-cooled 15 mL centrifuge tubes are sequentially added with 50 μL of pre-cooled PEG (12.5 g of PEG6000, 0.368 g of $CaCl_2$, 500 μL of Tris HCl, 1M, pH, 7.5), 10 μL of plasmid pAN52-mae linearized with HindIII, and 200 μL of protoplasts. After placing on ice for 20 min, to the centrifuge tubes were added with 2 mL of precooled PEG, and the product was kept in room temperature for 5 min, then added with 4 mL of solution B and gently mixed. 3 mL of the above solution was added into 12 mL of melt MM medium with corresponding antibiotics. The mixture was placed in the plate, and cultured at 45° C. After 2d-4d, single mycelium was selected from the solution under the stereomicroscope and subjected to the corresponding resistant plate for growth.

2.3 Validation of *Myceliophthora thermophila* Transformant

1) Genome Extraction

Genomic DNAs were extracted from the transformants selected in the above transformation process, using phenol chloroform method, which includes the following operations:

1) To 2.0 mL sterile DNA extraction tube was added 200 mg of zirconium beads and 1 mL of lysate (lysis buffer, formula: 0.2M Tris-HCl (pH 7.5), 0.5M NaCl, 10 mM EDTA, 1% SDS (w/v)). *Myceliophthora thermophila* hyphae growing on the plate were selected and placed in DNA extraction tube.

2) All the DNA extraction tubes were placed on the grinding mill, which were vibrated at the maximum speed for 30 s twice.

3) The tubes were heated in water bath at 65° C. for 30 min, and during the process the tubes were taken out for vortex oscillation every few minutes.

4) The tubes were retrieved after the water bath process completed, and to each tube was added 80 μL of pH 7.5, 1M, Tris HCl for neutralization.

5) 400 μl of phenol was added to the tubes: chloroform (1:1), and centrifuged at 13000 rpm for 5 minutes.

6) 300 μL of supernatant was taken and placed into a new 1.5 mL EP tube, to which was added 600 μL of 95% ethanol (DNA grade).

7) The product was incubated on ice for one hour, followed by centrifugation at 4° C. at 13000 rpm, then a white DNA precipitate can be observed at the EP tube bottom.

8) 400 μL of 75% alcohol (DNA level) was used for washing, and the product was centrifuged at 4 degree at 13000 rpm, and the supernatant was gently removed.

9) The EP tube was subjected to a vacuum concentrator and vacuum dried to remove alcohol.

10) 50 μL of $ddH_2O$ was added to dissolve DNA, and NanoDrop was used to measure DNA concentration. After the measurement, the extracted DNA was put in a refrigerator at −20° C. for PCR verification in the next step.

2) PCR Verification of *Myceliophthora thermophila* Transformat

The extracted genomic DNAs were used as a template to validate the transformants with tef-F and mea-R as primers. PCR reaction system: 5×phusion GC buffer 4 μL, 10 mM dNTPs 0.2 μL, 1 μL for each primers, genome 1 μL, DMSO 0.6 μL, Phusion DNA polymerase 0.1 μL, and water 12.1 μL. PCR reaction condition: 98° C. for 30 s at first, then 98° C. for 10 s, 62° C. for 30 s, 72° C. for 1.5 min, 30 cycles, 72° C. for 10 min and 4° C. for 10 min at last.

3) PCR amplification products were subjected to 1% agarose gel electrophoresis (110 V voltage, 30 min). Under the gel imaging system, the gene amplified bands were observed and showed that in the guidance of the upstream primer tef-F and the downstream primer mae-R, a 2360 bp target band was obtained by PCR amplification, which indicated that the pAN52-mae linearized by hindIII was integrated into the *Myceliophthora thermophila* genome.

3. Determination of Malic Acid Producing Capacity of *Myceliophthora thermophila* Transformant The above verified transformants were all inoculated into 50 mL of medium with crystalline cellulose (Avicel) as the carbon source in a 250 mL Erlenmeyer flask (formulation: 75 g/L of carbon source, 6.0 g/L of peptone, 0.15 g/L of $KH_2PO_4$, 0.15 g/L of $K_2HPO_4$, 0.10 g/L of $CaCl_2 \cdot 2H_2O$, 0.10 g/L of $MgSO_4 \cdot 7H_2O$, 80.0 g/L of calcium carbonate, 1 mL/L 0.5 g/L biotin, and 1 ml/L of trace element solution; the formulation of the trace element solution (100 mL): 5 g of $C_6H_8O \cdot 7H_2O$, 5 g of $ZnSO_4 \cdot 7H_2O$, 1 g of $Fe(NH_4)_2(SO_4) \cdot 6H_2O$, 0.25 g of $CuSO_4 \cdot 5H_2O$, 0.05 g of $MnSO_4 \cdot H_2O$, 0.05 g of $H_3BO_3$, 0.05 g of $NaMoO_4 \cdot 2H_2O$, dissolved in water to a volume of 100 mL) in an inoculation amount of $2.5 \times 10^5$/mL and cultured at 45° C. in 150 rpm. On the eighth day the malic acid content was determined.

1) Sample Treatment:

1 mL of fermentation broth was placed in a 15 mL centrifuge tube, to which was added 1 mL of 1M $H_2SO_4$, and then placed at 80° C. for 30 min with full vibration every 0 min. After that 2 mL double distilled water was added to the centrifuge tube. After through vibration, 1 mL of liquid was subjected to a 1.5 mL centrifuge tube and centrifuged in 12000 rpm for 10 min. The content of C4-bicarboxylic acid was verified by measuring the supernatant.

2) Verification of the Content of C4-Bicarboxylic Acid

Figure 9:
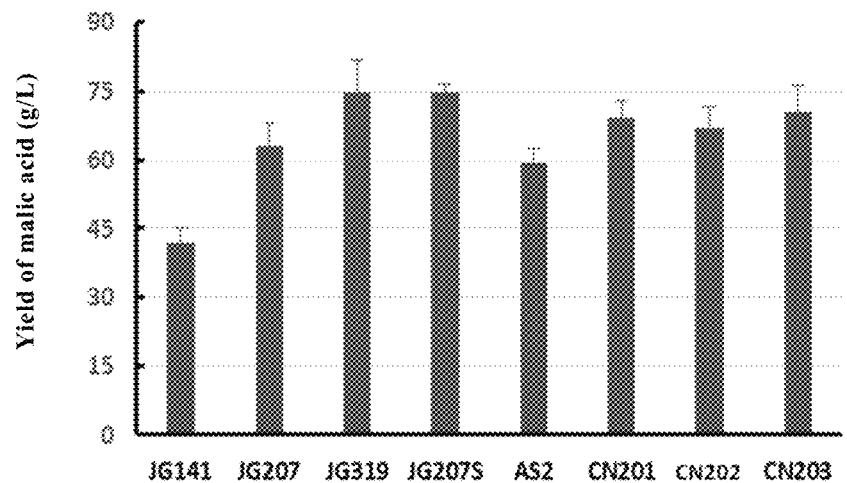
FIG. 9 shows the malic acid yield map in different strains on the eighth day with crystalline cellulose as a carbon source.

The content of malic acid and succinic acid in the treated sample were determined by HPLC, wherein the detector was UV detector, the mobile phase was 5 mM $H_2SO_4$, and the flow rate was 0.5 mL/min. The results showed that mae overexpression in *Myceliophthora thermophila* can significantly promote the malic acid production, in which the strains with a highest yield were named as JG141. On the eighth day, the malic acid production was 42 g/L (FIG. 9), the succinic acid production was 3.86 g/L for the corresponding carbon source. The experiments showed that after the genetic modification, the fermentation of malic acid could be carried out in *Myceliophthora thermophila* by using the carbon source including crystalline cellulose.

Example 2 Overexpression of C4-Dicarboxylic Acid Transporter Encoding the Genes of *Myceliophthora thermophila* from Different Origins can Obtain Recombinant Microorganisms with Significant Increased Capacity for Producing Malic Acid 1. Homology Comparison Analysis of C4-Dicarboxylic Acid Transporter In this example, C4-dicarboxylic acid transporter from *Aspergillus oryzae* NRRL3488 (AO090023000318, mae, SEQ ID NO.: 12), C4-dicarboxylic acid transporter from *Neurospora crassa* (XP_958365, NCmae, SEQ ID NO.: 14), C4-dicarboxylic acid transporter from *Trichoderma reesei* (XP_006963989, Trmae, SEQ ID NO.: 16), C4-dicarboxylic acid transporter from *Myceliophthora thermophila* (XP_003663832, Mtmae, SEQ ID NO.: 18), C4-dicarboxylic acid transporter from *Aspergillus niger* NRRL599 (XM_001398094, Anmae, SEQ ID NO.: 20), C4-dicarboxylic acid transporter from *Aspergillus sojae* NBRC4239 (Asmae, SEQ ID NO.: 22) were selected.

2. Construction of C4-Dicarboxylic Acid Transporter Gene Expression Vector Promoter A 1.0 kb upstream promoter of the translation elongation encoding frame tef (MYCTH_2298136) was amplified by PCR from the original strain of *Myceliophthora thermophila* ATCC 42464 as a template. The reaction system and conditions were shown in Step 1 of Example 1. According to the constructed plasmids, the primers used for PCR amplification were:

Tef-2F:
                                      (SEQ ID NO.: 55)
GAAGATCTCATGTACCTTGACGTCCTCCGAG

Tef-2R:
                                        (SEQ ID NO.: 56)
GGACTAGTTCTGAAGAACGAAACTGGCGACT

Figure 2:
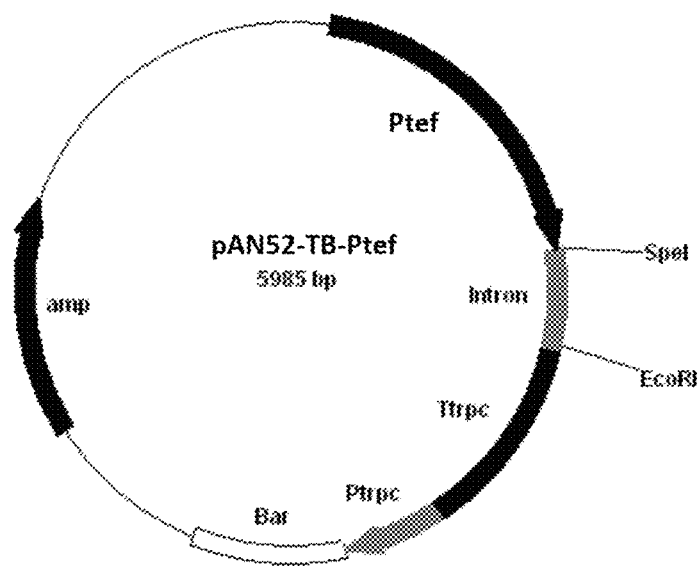
FIG. 2 shows a physical map of the expressing vector pAN52-TB-Ptef.

After PCR reaction, the recombinant plasmid was digested with BglII and SpeI and ligated into the linearized vector pAN52-TB-Intron, which was digested by the same enzyme. The ligation product was digested with restriction endonuclease and identified to obtain the recombinant vector, named as pAN52-TB-Ptef. The physical map was shown in FIG. 2.

3. Construction of C4-Dicarboxylic Acid Transporter Gene Expression Vector 3.1 The gene encoding C4-dicarboxylic acid transporter Ncmae (SEQ ID NO.: 13) was obtained by PCR amplification using *Neurospora crassa* (purchased from FGSC) as a template, and the primers used for PCR amplification were as follows:

NCmae-F:
                                      (SEQ ID NO.: 45)
GGACTAGTATGGGCAGCCAGCCTCCCATGC NCmae-R:
                                        (SEQ ID NO.: 46)
CGGAATTCCTAATGATCCTCCACATCCTCA 3.2 The gene encoding C4-dicarboxylic acid transporter Trma (SEQ ID NO.: 15) was obtained by PCR amplification using *Trichoderma reesei* (purchased from ATCC) as a template, and the primers used for PCR amplification were as follows:

Trmae-F:
                                      (SEQ ID NO.: 47)
GGACTAGTATGAAAGCGGCATTCCCTCATGC Trmae-R:
                                      (SEQ ID NO.: 48)
CGGAATTCTCAGTGATCCTCCACATTCTCATC 3.3 The gene encoding C4-dicarboxylic acid transporter Mtmae (SEQ ID NO.: 17) was obtained by PCR amplification using *Myceliophthora thermophila* ATCC42464 (purchased from ATCC) as a template, and the primers used for PCR amplification were as follows:

Mtmae-F:
                                      (SEQ ID NO.: 49)
CGGACTAGTATGTCAACACCGCGGCGAAG Mtmae-R:
                                      (SEQ ID NO.: 50)
CCGGAATTCTTAATGATCCTCCACGTCCTC 3.4 The gene encoding C4-dicarboxylic acid transporter Anmae(XM_001398094)(SEQ ID NO.: 19) was obtained by PCR amplification using *Aspergillus niger* NRRL599 as a template, and the primers used for PCR amplification were as follows:

Anmae-F:
                                      (SEQ ID NO.: 51)
GGACTAGTATGAACGTTGAAACGAGC Anmae-R:
                                      (SEQ ID NO.: 52)
CGGAATTCTCATTCAGACACATCCTCAT 3.5 The gene encoding C4-dicarboxylic acid transporter Asmae (SEQ ID NO.: 21) was obtained by PCR amplification using *Aspergillus sojae* NBRC4239 as a template, and the primers used for PCR amplification were as follows:

Asmae-F:
                                      (SEQ ID NO.: 53)
GCTCTAGAATGCTGACACCTCCCAAGTTTGAGGATG Asmae-R
                                      (SEQ ID NO.: 54)
CCTTAATTAACTAATCAGATACATCCTCATCTTTACCC The PCR product of C4-dicarboxylic acid transporter gene fragments obtained through PCR amplification and analysis and the plasmid pAN52EF-Intron were digested by restriction endonuclease SpeI and EcoRI. Then, they were ligated by T4 DNA ligase to obtain the expression plasmids, named as pAN52-Ptef-Ncmae, pAN52-Ptef-Trmae, pAN52-Ptef-Mtmae, pAN52-Ptef-Anmae, and pAN52-Ptef-Asmae respectively.

4. Analysis of Malic Acid Produced by Fermentation of *Myceliophthora thermophila* Recombinant Transformants (1) The Obtain of Recombinant *Myceliophthora thermophila* Transformants The constructed gene expression vectors (pAN52-Ptef-Ncmae, pAN52-Ptef-Trmae, pAN52-Ptef-Mtmae, pAN52-Ptef-Anmae, pAN52-Ptef-Asmae) were integrated into the original strains of *Myceliophthora thermophila* strains genome and use glufosinate at a final concentration of 100 μg/mL as an antibiotic for screening. The method of the example was shown in step 2 in example 1. The transformat was verified using primer tef-2F and the downstream primer corresponding to gene cloning. PCR system and methods were shown in step 1.3 in example 1.

All of the transformants verified were inoculated into a 250 mL conical flask containing 50 mL of medium with crystalline cellulose (Avicel) as the carbon source (see step 3 in example 1) in a inoculation amount of $2.5 \times 10^5$/mL, then subjected to the culture at 45° C. in 150 rpm, and the sample was taken on eighth day. After the sample was treated by the method as described in step 3.2 of example 1, the malic acid content in the fermentation broth was determined.

Figure 10:
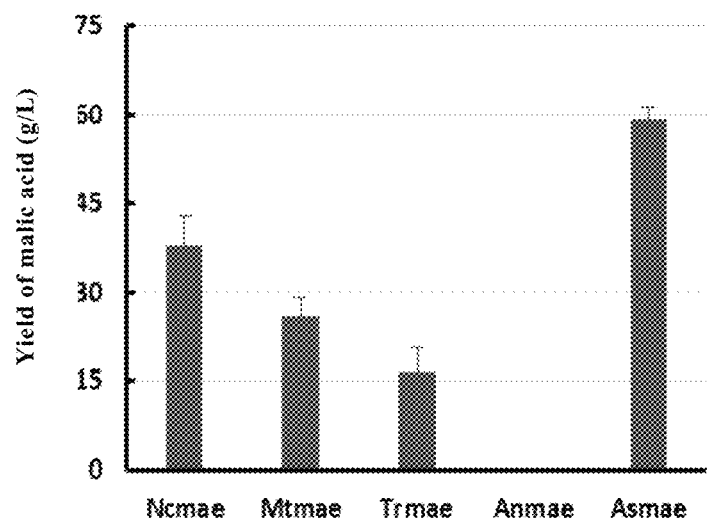
FIG. 10 shows a malic acid yield map in *M. thermophila* which overexpresses C4-dicarboxylic acid transporter.

The results showed that overexpression of C4-dicarboxylic acid transporter derived from different species in *Myceliophthora thermophila* can significantly promote the production of malic acid, and the malic acid yield went up to (see FIG. 10): 37.9 g/L (Ncmae), 26.1 g/L (Mtmae), 16.6 g/L (Trmae), 0.24 g/L (Anmae) and 59.4 g/L (Asmae), respectively. It showed that C4-dicarboxylic acid transporter from *Neurospora crassa, Myceliophthora thermophila, trichoderma reesei* and *Aspergillus sojae* can be used to construct *Myceliophthora thermophila* strains for malic acid fermentation in industry. But it should be noted that although C4-dicarboxylic acid transporters from *Aspergillus niger* and *Aspergillus oryzae* have a high identity (about 90%), in this experiment when the C4-dicarboxylic acid transporter from *Aspergillus niger* was overexpressed in the *Myceliophthora thermophila*, the transformants did not show the capacity of producing malic acid suitable for industrial application. It can be seen that even in the *Aspergillus* strain with an ability for accumulating malic acid, the proteins with high identity failed to enable other strains have better malic acid-producing capacity.

For the genes derived from different strains, the inventors conducted more experiments to study whether genes from non-dominant strains for organic acids accumulation (*Neurospora crassa, Trichoderma reesei*, etc.) can be used by metabolic engineering method to improve the capacity for producing dibasic acid of their own or other strains.

Example 3 the C4-Two Carboxylic Acid Transport Protein Coding Gene Mae and Pyruvate Carboxylase Gene Pyc are Simultaneously Expressed in the *Myceliophthora thermophila* so as to Strengthen the Ability to Produce Malic Acid 1. Construction of Co-Expression Vectors Containing mae and pyc The promoters of *aspergillus nidulans* gpdA was amplified by PCR using the plasmid pAN52-TB-Intron as the template in the guidance of primers. The PCR conditions and system were described in step 1 of Example 1. The primer was shown as follows:

ANgpadA-F: (SEQ ID NO.: 61)
CCTTAATTAAGTCCAGATCATGGTTGACCGGTG

ANgpadA-R: (SEQ ID NO.: 62)
GAACCTCCTTCAGAGAGGTTCGTGTTTAAACTGATGTCTGCTCAAGCGG
GGTA Then the cellobioses hydrolase encoding gene cbh (MYCTH_109566) terminator (SEQ ID NO.: 85) was amplified by PCR using the primers and the original strain *Myceliophthora thermophila* genome as a template. The primers were shown as follows:

CBH-F: (SEQ ID NO.: 63)
ACCCCGCTTGAGCAGACATCAGTTTAAACACGAACCTCTCTGAAGGAGG
TTC

CBH-R: (SEQ ID NO.: 64)
CCCAAGCTTCTAATAGGGATAATAAGCTAGGGTC

The gpdA promoter and cbh terminator were ligated together by fusion PCR using the method of gene overlap extension (SOE), which was invented by Horton et al. 1989 (Horton R M, Hunt H D, Ho S N, Pullen J K, Pease L R. 1989. Engineering hybrid genes without the use of restriction enzymes: gene splicing-by-overlap extension. Gene 77: 61-68).

The An_gpdA promoter and cbh terminator were digested by HindIII to provide adhesive ends and then ligated into pAN52-mae which was digested with the same enzyme to give the recombinant vector: pAN52-mae-PgpdA-Tcbh.

Figure 3:
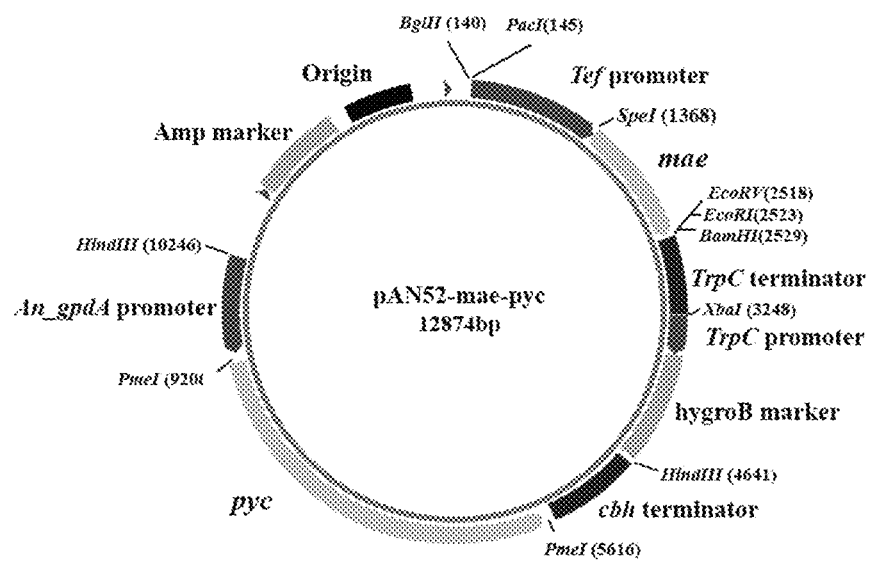
FIG. 3 shows a physical map of the mae gene and pyc gene co-expression vector pAN52-mae-pyc.

Pyruvate carboxylase encoding gene pyc (XM_001820829.2, SEQ ID NO.: 25) was amplified by PCR using *Aspergillus oryzae* DSM1863 cDNA as a template in the guidance of primer PYC-F (SEQ ID NO.: 57) and PYC-R (SEQ ID NO.: 58), then digested by PmeI and ligated into pAN52-mae-PgpdA-Tcbh which was digested with the same enzyme. The recombinant plasmid was verified by PCR with primers PYC-F and PYC-R, and then sequenced. The sequencing results confirmed that the sequence of the plasmid was the nucleotide sequence of pyc gene, which showed that the recombinant plasmid with the correct insertion position and carrying pyc gene was obtained and named as pAN52-mae-pyc. The physical map of the expression vector was shown in FIG. 3.

2. Determination of malic acid-producing capacity by *Myceliophthora thermophila* transformants fermentation using monosaccharides, glycans and biomass as a carbon source.

The coexpression vector pAN52-mae-pyc containing mae and pyc was linearized by BglII and then integrated into the genome of the original strain *Myceliophthora thermophila*, and the method was described in step 2 of example 1. The transformants were obtained and verified using primers mae-F (SEQ ID NO.: 43) and mae-R (SEQ ID NO.: 44) (to verify mae was intergrated into the genome), PYC-F and PYC-R (to verify pyc was integrated into the genome). PCR system and conditions was shown in step 1.3 of example 1.

The verified transformants were all inoculated into 250 mL Erlenmeyer flask with 50 mL of medium containing glucose, D-xylose, cellobiose, xylan, crystalline cellulose, sucrose, soluble starch, corncobs xylose slag and corncobs delignification as carbon source (the formulation was shown in step 3 of example 1) and cultured in an inoculated amount of $2.5 \times 10^5$ cells/mL at 45° C. in 150 rpm and sampled on the eighth day. After the sample was treated by the method as described in step 3.2 of example 1, the malic acid content in the fermentation broth was determined.

The results showed that when mae and pyc were overexpressed simultaneously in *Myceliophthora thermophila*, the production of malic acid was significantly promoted. One of the strains was named as JG207. On the eighth day, the yields of malic acid and succinic acid in the transformants using various carbon sources were: 62 g/L and 3.2 g/L (glucose), 28 g/L and 6.4 g/L (D-xylose), 78.7 g/L and 8.6 g/L (cellobiose), 61.3 g/L and 11 g/L (xylan), 63 g/L and 7.2 g/L (crystalline cellulose), 36.3 g/L and 4.7 g/L (sucrose), 46.3 g/L and 16.0 g/L (soluble starch), 36.8 g/L and 9.1 g/L (corncobs xylose slag), 55.15 g/L and 8.1 g/L (corncob delignification slag).

Example 4 Overexpressing Malate Dehydrogenase Encoding Gene mdh in *Myceliophthora thermophila* Transformant Further Enhanced its Ability to Produce Malic Acid 1. Construction of mdh Overexpression Vectors The promoter PtrpC (SEQ ID NO.: 86) of the tryptophan synthase-encoding gene from *Aspergillus nidulans* was amplified under the guidance of primers using pAN52-TB-Intron as a template. The primers were shown as follows:

```
Trpc-F:
                                   (SEQ ID NO.: 65)
CTTTCTAGACGACGTTAACTGATATTGAAGGAGC Trpc-R:
                                   (SEQ ID NO.: 66)
CGTGCAATCCATCTTGTTCAATCATTTGGATGCTTGGGTAGAATAGGTAA
```

The neomycin phosphotransferase encoding gene neo (GI: 339515868) was amplified by PCR using primers and plasmid pEGFP-N2 as a template. The reaction system and conditions were shown in Step 1 of Example 1. The primers were shown as follows:

```
NEO-F:
                                   (SEQ ID NO.: 67)
TTACCTATTCTACCCAAGCATCCAAATGATTGAACAAGATGGATTGCACG

NEO-R:
                                   (SEQ ID NO.: 68)
AAAAAAAGCTTGGTACCATCGATGCGGCCGCCCGCGGTCAGAAGAACTCG
TCAA.
```

The sequence of PtrpC and Neo were ligated together by the fusion PCR method and the specific method is gene overlap extension (SOE).

PtrpC and neo were digested by XbaI and HindIII to obtain sticky ends and then ligated into pAN52-TN-Intron which was digested by the same enzymes to obtain the recombinant vector with Neo as the screening marker, and the product was named as pAN52-TN.

The sequence of the promoter MtPgpdA at 1.5K upstream of 3-phosphoglyceraldehyde dehydrogenase-encoding gene of the original strain *Myceliophthora thermophila* was optimized to remove the restriction site, and the artificially synthesized sequence was shown as SEQ ID NO.: 69. Using the above as a template and in guidance of primers, MtPgpdA was amplified, then digested by BglII and BamHI, and then ligated into the linearized vector pAN52-TN which was digested by the same enzyme enzymes, so as to obtain the recombinant plasmid containing gpdA promoter: pAN52-TN-MtPgpdA. The primers were shown as follows:

```
MtPgpdA-F:
                                   (SEQ ID NO.: 70)
TGCAGATCTTTAATTAACTCGAGTGACGGTGCTTTTCACCTCTC MtPgpdA-R:
                                   (SEQ ID NO.: 71)
AGTGGATCCGAATTCGATATCGTTTAAACACTAGTTTTGATTTCTGTGAT
GTGG
```

The malate dehydrogenase encoding gene mdh (MYCTH_2315052) in *Myceliophthora thermophila* was amplified by PCR in the guidance of primers and using the original strain of *Myceliophthora thermophila* cDNA as template. The primers were shown as follows:

```
MtMDH-F:
                                   (SEQ ID NO.: 59)
CGGACTAGTATGGTCAAAGCTGTCGTTGCTG

MtMDH-R:
                                   (SEQ ID NO.: 60)
CGCGGATCCTCACTTCTGGGGGGGGTTGTG.
```

Figure 4:
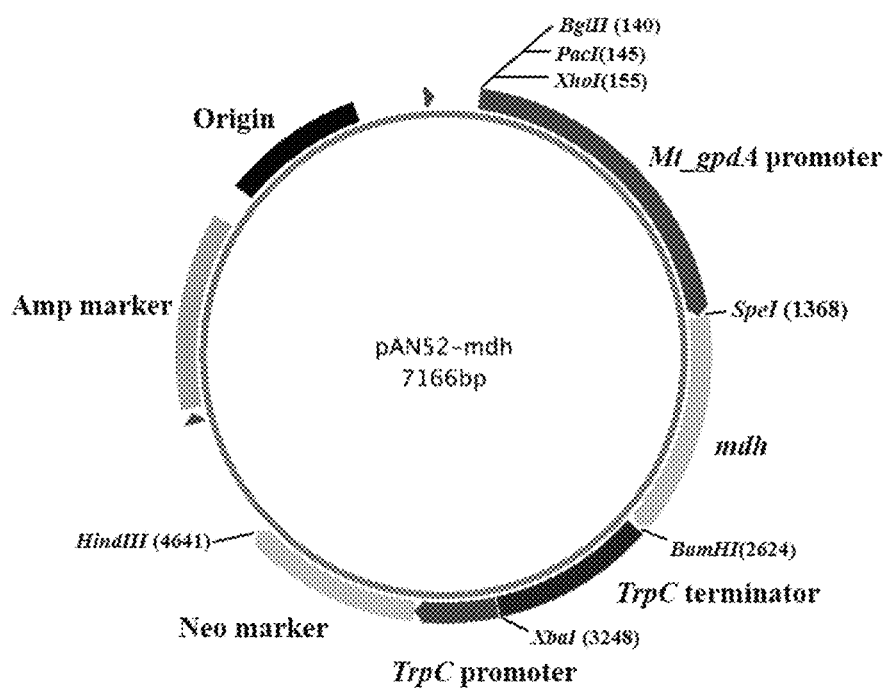
FIG. 4 shows a physical map of the mdh gene expression vector pAN52-mdh.

After digested by SpeI and BamHI, the plasmid was ligated into linearized plasmid pAN52-TN-MtPgpdA which was digested by the same enzymes so as to obtain recombinant vector expressing mdh, named as pAN52-mdh, and the physical map of the expressing vector was shown in FIG. 4.

2. Determination of the capacity of *Myceliophthora thermophila* transformant for producing malic acid.

The mdh overexpression vector pAN52-mdh was linearized by Bgl II and then intergrated into the *Myceliophthora thermophila* JG207 strains genome. The final concentration was 100 μg/mL. G418 was used as the screening antibiotics. The method was shown in step 2 of example 1. The transformant was verified and obtained using primers MtPgpdA-F and MtMDH-R. The PCR system and methods were described in step 1.3 of example 1.

All of the transformants verified were inoculated into a 250 mL conical flask containing 50 mL of medium with crystalline cellulose (Avicel) as the carbon source (see step 3 in example 1) in a inoculation amount of $2.5 \times 10^5$/mL and subjected to culture at 45° C. in 150 rpm, and sampled on eighth day. After the sample was treated by the method as described in step 3.2 of example 1, determine the malic acid content in the fermentation broth.

The results showed that when mae and pyc were overexpressed in *Myceliophthora thermophila* simultaneously, the malic acid production can be significantly promoted. One of the strains was named as JG319. On the eighth day the yield of malic acid was 75 g/L (FIG. 9), the yield of succinic acid was 9.3 g/L. The conversion rate of malic acid went up to 1.0 g/g Avicel.

Example 5 Inhibiting the Expression of Succinyl-CoA Synthase by RNA Interference to Improve the Fermentation Level of Malic Acid 1. The upstream promoters interfering vector construction, named as P1 and P2 promoter (SEQ ID NO.: 72 and 73), were digested with BglII and PmeI and then ligated respectively into linearized vector pAN52-TB-Intron which was digested with the same enzymes to obtain the recombinant plasmid respectively named as pAN52-TB-Psilent-A and pAN52-TB-Psilent-B.

The first interference sequence SCL-S1 (SEQ ID NO., 74) of the succinyl-CoA synthase encoding gene scl in *Myceliophthora thermophila* was amplified by PCR in the guidance of primers, and the primers were shown as follows:

```
SCL1-F:
                                   (SEQ ID NO.: 31)
CCATCGATCATCAAGAACCTGTACCGCATC

SCL1-R:,
                                   (SEQ ID NO.: 32)
GGGTTTAAACCAATGATGGGGA, TCTTCAGGTC.
```

The second interference sequence SCL-S2(SEQ ID NO.: 75) of the succinyl-CoA synthase encoding gene scl in *Myceliophthora thermophila* was amplified by PCR in the guidance of primers.

SCL2-F:

(SEQ ID NO.: 33)

CGCGGATCCCAATGATGGGGATCTTCAGGTC

SCL2-R:

(SEQ ID NO.: 34)

CGCGGATCCGTTTAAACCATCAAGAACCTGTACCGCATC.

Figure 5:
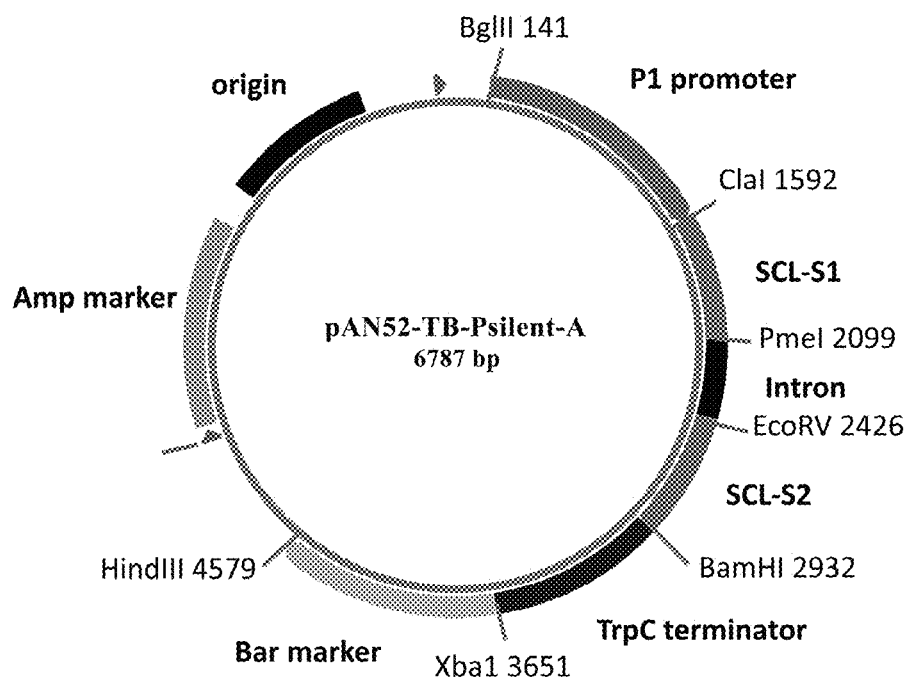
FIG. 5 shows a physical map of a binary carrier pAN52-SCLsilent-A.
Figure 6:
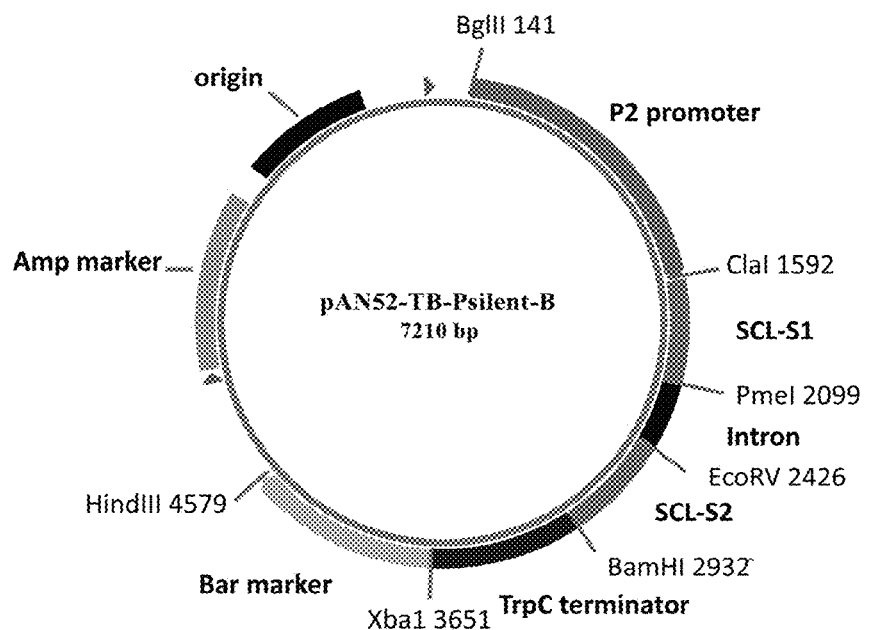
FIG. 6 shows a physical map of a binary carrier pAN52-SCLsilent-B.

Two interference sequences of scl were digested with ClaI/PmeI and BamHI respectively and then ligated into the linearized plasmids pAN52-TB-Psilent-A and pAN52-TB-Psilent-B which were digested with the same enzymes so as to obtain a binary vector of transcription element containing SCL gene interference sequence hairpin structure and screening marker bar gene: pAN52-SCLsilent-A and pAN52-SCLsilent-B. The physical maps were shown in FIG. 5 and FIG. 6.

2, Interfering the Succinyl-CoA Synthase Expression Significantly Increased the Malic Acid-Producing Ability in Microorganisms The binary vector pAN52-SCLsilent-A and pAN52-SCLsilent-B of transcription element containing the hairpin structure of the SCL gene interference sequence and screening marker bar gene were integrated into the genome of the *Myceliophthora thermophila* JG207 strain respectively. The final concentration was 100 μg/ML and glufosinate was used as screening antibiotic. The method was described in Example 1, Step 2. The transformant was obtained and verified using primers Intron-F(AGCTGTTTACTCATTATTAC, SEQ ID NO.: 76) and SCL2-R(SEQ ID NO.: 34). The PCR system and methods were described in step 1.3 of example 1.

All of the verified transformants were inoculated into a 250 mL conical flask containing 50 mL of medium with crystalline cellulose (Avicel) as the carbon source (see step 3 in example 1) at a inoculation amount of $2.5 \times 10^5$/mL. The product was cultured at 45° C. in 150 rpm, and sampled on eighth day. After the sample was treated by the method as described in step 3.2 of example 1, the malic acid content in the fermentation broth was determined.

The results showed that the yield of the malic acid in *Myceliophthora thermophila* JG207 intergrated with pAN52-SCLsilent-A was similar to that in the original strain JG207, and the yield of malic aid was 68 g/L on the eighth day. While compared to the original strain JG207, the yield of the malic acid in *Myceliophthora thermophila* JG207 intergrated with pAN52-SCLsilent-B was improved significantly, the strain with highest yield was named as JG207S, and the final yield of the malic acid (fermented for eighth days) was 74.8 g/L (FIG. 9), which was increased by 15.3%.

This example illustrates that the transcription of the RNA interference sequence hairpin structure regulated by the time-controlled promoter interfered the translation of the key enzymes encoding genes in the TCA cycle, thereby reducing the tricarboxylic acid cycle and significantly improving the malic acid producing ability in the microorganism.

Since then, the inventors used the single gene mutant of *Neurospora crassa* as a host to screen out the new key genes for producing malic acid in microorganism: aspartate aminotransferase, glutamic acid-aspartate transporter, Malic acid-alpha ketoglutarate transporter. In the following experiment, the inventors further verified these newly discovered genes which were related to the synthesis of dicarboxylic acid.

Example 6 Regulating Aspartate Aminotransferase in *Myceliophthora thermophila* During the Malic Acid-Aspartate Shuttle Pathway can Significantly Improve the Ability of Microorganisms to Synthesize Malic Acid 1. Construction of Aspartate Aminotransferase Expression Vector The nucleic acid sequence CI7941 (MYCTH_2314321) (SEQ ID NO.: 3) encoding aspartate aminotransferase was obtained by PCR amplification using *Myceliophthora thermophila* genome as a template with primer pairs designed according to aspartate aminotransferase searched in the published genome database information (http://genome.jgi-.doe.gov/Spoth2/Spoth2.home.html). After the nucleic acid sequence was digested with SpeI and EcoRI, it was ligated into linearized vector pAN52gpdA-CI7941 which was digested with the same enzymes to obtain the recombinant plasmid and named as pAN52gpdA-CI7941. The primers were shown as follows:

CI7941-F:

(SEQ ID NO.: 35)

GGACTAGTATGGCGCCGACGTCAACAACG

CI7941-R:

(SEQ ID NO.: 36)

CGGAATTCTCATTGCACCTCCCGAACCAC

2. Determination of Malic Acid-Producing Capacity of *Myceliophthora thermophila* Transformant The aspartate aminotransferase overexpression vector pAN52gpdA-CI7941 was intergrated into *Myceliophthora thermophila* AS2 strain (which was intergrated with *Myceliophthora thermophila* transformant of Asmae overexpression vector derived from *Aspergillus sojae*, see example 2) genome, with a final concentration of 100 μg/mL and using G418 as the screening antibiotic. The method was shown in step 2 of Example 1.

All of the verified transformants were inoculated into a 250 mL conical flask containing 50 mL of medium with crystalline cellulose (Avicel) as the carbon source (see step 3 in example 1) at a inoculation amount of $2.5 \times 10^5$/mL. The product was cultured at 45° C. in 150 rpm, and sampled on eighth day. After the sample was treated by the method as described in step 3.2 of example 1, the malic acid content in the fermentation broth was determined.

The results showed that the intergration of the aspartate aminotransferase into *Myceliophthora thermophila* AS2 can significantly promote the production of malic acid. The strain with the highest yield was named as CN201. On the eighth days the yield of malic acid was 69.2 g/L (FIG. 9), which was increased by 10% compared to the control strain AS2.

This example illustrated that the overexpression of the gene related to malic acid-aspartic acid shuttle pathway, i.e. aspartate aminotransferase can improve the ability of microorganisms to produce malic acid.

Example 7 Regulating Glutamic Acid-Aspartate Transporter *Myceliophthora thermophila* During the Malic Acid-Aspartate Shuttle Pathway can Significantly Improve the Ability of Microorganisms to Synthesize Malic Acid 1. Construction of Glutamic Acid-Aspartate Transporter Expression Vector The nucleic acid sequence CI1241(MYCTH_2300593) (SEQ ID NO.: 5) encoding aspartate aminotransferase was obtained by PCR amplification using *Myceliophthora thermophila* genome as a template with primer pairs designed according to glutamic acid-aspartate transporter searched in the published genome database information (http://genome.jgi.doe.gov/Spoth2/Spoth2.home.html), and the primer pairs were:

```
CI1241-F:
                                      (SEQ ID NO.: 35)
GGACTAGTATGTCCAAGGCCGCAACTGTC

CI1241-R:
                                      (SEQ ID NO.: 36)
CGGAATTCCTACGCCGTCTTTGCGTTCATC.
```

After the nucleic acid sequence was digested with SpeI and EcoRI, it was ligated into linearized vector pAN52-TN-MtPgpdA which was digested with the same enzymes to obtain the recombinant plasmid named as pAN52gpdA-CI1241.

2. Determination of Malic Acid-Producing Capacity of *Myceliophthora thermophila* Transformant The glutamic acid-aspartate transporter overexpression vector pAN52gpdA-CI1241 was intergrated into *Myceliophthora thermophila* AS2 strain (which was intergrated with *Myceliophthora thermophila* transformant of Asmae overexpression vector from *Aspergillus sojae*, see example 2) genome, with a final concentration of 100 μg/mL and using G418 as the screening antibiotic. The method was shown in step 2 of Example 1.

All of the verified transformants were inoculated into a 250 mL conical flask containing 50 mL of medium with crystalline cellulose (Avicel) as the carbon source (see step 3 in example 1) at a inoculation amount of $2.5 \times 10^5$/mL. The product was subjected to culture at 45° C. in 150 rpm, and sampled on eighth day.

After the sample was treated by the method as described in step 3.2 of example 1, the malic acid content in the fermentation broth was determined. The results showed that overexpression of *Aspergillus sojae* Asme and *Myceliophthora thermophila* glutamic acid-aspartate transporter (CI1241) simultaneously can significantly promote the malic acid production in *Myceliophthora thermophila*., One of the strains was named as CN202, and on the eighth day the yield of malic acid was 66.9 g/L (FIG. 9), which was increased by 10% compared to the control strain AS2.

This example illustrated that the overexpression of gene glutamic acid-aspartate transporter related to malic acid-aspartic acid shuttle pathway can improve the ability of microorganisms to produce malic acid.

Example 8 Gene Deletion of Malic Acid-Alpha Ketoglutarate Transporter Gene could Improve the Ability of *Myceliophthora thermophila* Strain CN2 to Produce Malic Acid (1) Amplification of Malic Acid-Alpha Ketoglutarate Transporter Gene and its Upstream and Downstream Homologous Arm Nucleic Acid Fragments The upstream and downstream homologous arm nucleic acid sequences of the gene encoding malic acid-alpha ketoglutarate transporter UL and DL were obtained by PCR amplification using *Myceliophthora thermophila* genome as template with the primer pairs designed according to the sequence of malic acid-alpha ketoglutarate transporter gene (MYCTH_2081554, SEQ ID NO.: 91) and its upstream and downstream homologous arm nucleic acid searched in the published genome database information (http://genome.jgi.doe.gov/Spoth2/Spoth2.home.html), and the primer pairs were:

```
CI4837-UF:
                                      (SEQ ID NO.: 39)
GCTCTAGATGCTTGCAGGAACTCTCTGTGAAACC

CI4837-UR:
                                      (SEQ ID NO.: 40)
GCGTTAACCCCACAGTTTGGAGAGACGACATCG

CI4837-DF:
                                      (SEQ ID NO.: 41)
CCTTAATTAATGTATATACGGGGCGAATACGAAGG

CI4837-DR:
                                      (SEQ ID NO.: 42)
CGGAATTCTTCCTCCTGCAAACTCAGCTTGAG.
```

UL and DL were sequenced by Beijing Liuhe Huada Gene Technology Co., Ltd. and analyzed by NCBI Blast.

(2) Construction of a Vector with Malic Acid-Alpha Ketoglutarate Transporter Gene-Knocked Out Sur gene fragment (GI:2547090) was amplified using plasmid pPK2surGFP as a template with the following primer pairs:

```
Sur-F:
                                      (SEQ ID NO.: 77)
GCTCTAGAGTTAACGCGGCCGCGACTAGATCTGTGCCAACGCCACAG

Sur-R:
                                      (SEQ ID NO.: 78)
CGGAATTCGTTTAAACTTAATTAACCGACGGAATTGAGGATATCAGTCAC
```

PCR products and plasmid pPK2barGFP were digested with restriction endonuclease XbaI and EcoRI and then ligated by T4 DNA ligase to obtain plasmid pPK2sur-barGFP.

Figure 7:
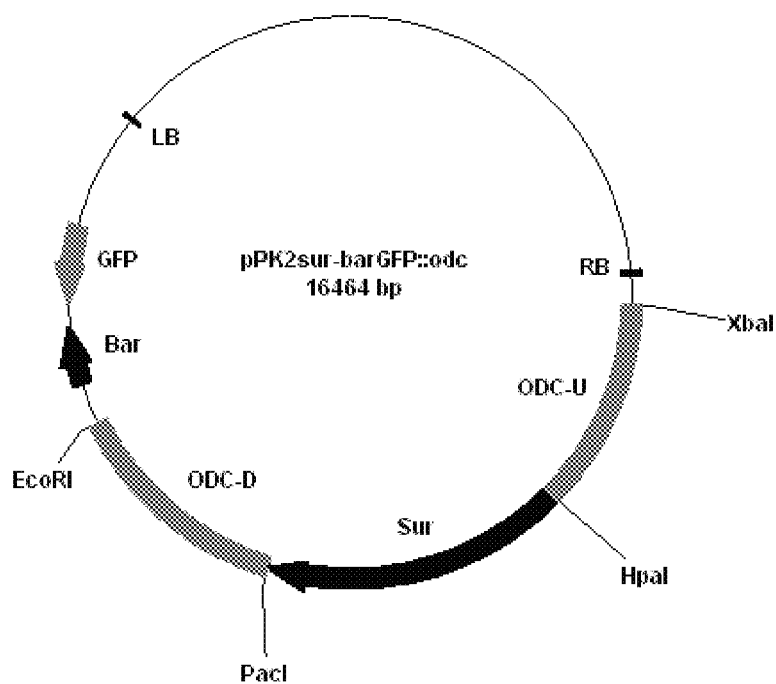
FIG. 7 shows a physical map of the knocking out carrier pPK2sur-barGFP:: odc.

The above upstream and downstream homologous arm fragments of malic acid-alpha ketoglutarate transporter gene were obtained through PCR amplification and sequencing analysis. The PCR product of the upstream homologous arm was digested with restriction endonuclease XbaI and HpaI and the PCR product of the downstream homologous arm was digested with PacI and EcoRI. The plasmid pPK2sur-barGFP was digested with the same enzymes and then ligated with the upstream and downstream homologous arms using T4 DNA ligase to obtain the knock-out vector: pPK2sur-barGFP:: odc (FIG. 7).

(3) The Vector pPK2sur-barGFP::odc with Gene Knocked Out was Used to Transform *Myceliophthora thermophila* AS2 to Obtain Transformants The transformant was verified by PCR with the primer CI4837-F2 located outside the upstream homologous arm at the 5' end of gene of malic acid-alpha ketoglutarate transporter in *Myceliophthora thermophila* and Sur-R2 within Sur gene, the primers were as follows:

```
CI4837-F2:
                                    (SEQ ID NO.: 87)
CAGACTGTGTGGTTCTGCAACAGG

Sur-R2:
                                    (SEQ ID NO.: 88)
GGCCAACAGTACGAAGCATTTCG
```

PCR results showed that CI4837-F2 and Sur-R were able to amplify fragments of 3 KB size, which indicated that the Sur gene had been replaced malic acid-alpha ketoglutarate transportermalate encoding gene CI4837.

At the same time, the transformant genome was amplified using ORF amplified primers CI4837-F and CI4837-R of malic acid-alpha ketoglutarate transporter encoding gene doc, and the sequences of the primers were as follows:

```
CI4837-F:
                                    (SEQ ID NO.: 89)
ATGGCGTCAGCAAAGGAGAAGG

CI4837-R:
                                    (SEQ ID NO.: 90)
CTACGCCTCGCCATCCCTAATC
```

PCR result showed that no fragment was amplified by using primers CI4837-F and CI4837-R, which indicated that the obtained transformants were pure nuclei.

(4) Fermentation of the Transformants to Produce Malic Acid 250 mL triangle flask was used as a fermentation container, and the volume of the fermentation system in each was 50 mL of. The formulation of the fermentation medium of malic acid was as follows: microcrystalline cellulose 7.5%, peptone 6.0 g/L, 0.15 g/L $KH_2PO_4$, 0.15 g/L $K_2HPO_4$, 0.10 g/L $CaCl_2 \cdot 2H_2O$, 0.10 g/L, $MgSO_4 \cdot 7H_2O$, 80.0 g/L calcium carbonate, 1 ml/L trace elements solution (5 g NaCl, 5 g FeSO4·7H$_2$O, 1 g citric acid/L water).

32 transformants were collected by physiological saline solution. After filtered with 2-layer lens wiping paper, the number of spores was calculated, and the inoculation amount was $2.5 \times 10^5$/ml. The transformants were cultured at 45° C. at 150 rpm and sampled on fourth, sixth and eighth days. After the samples were treated, the malic acid content was analyzed by HPLC. One strain was named as CN203, in which the yield of malic acid was 70.5 g/L (FIG. 9) on the eighth day. Compared to the control strain AS2, the yield of malic acid was increased by more than 10%.

Example 9 Overexpression of Glucose Transporter Gene in *Myceliophthora thermophila* can Increase Producing Capacity 1. Construction of glt-1 Overexpression Vector (pAN52-glt)

The glucose transporter encoding gene glt-1 (NCU01633, SEQ ID NO: 95) was amplified by PCR using cDNA under glucose condition from *Neurospora crassa* FGSC #2489 (purchased from Fungal Genetics Stock Center) as a template and primers. The primers were shown as follows:

```
GLT-F:
                                    (SEQ ID NO.: 93)
CGGACTAGTATGGTCAAAGCTGTCGTTGCTG

GLT-R:
                                    (SEQ ID NO.: 94)
CGCGGATCCTCACTTCTGGGGGGGGTTGTG.
```

The gene was digested with SpeI and EcoRI and then ligated into the linearized plasmid pAN52-TB-MtPgpdA which was digested with the same enzymes, so as to obtain glt-1 expression vector, named as pAN52-glt.

2. Introducing the Expression Vector (pAN52-glt) into *Myceliophthora thermophila*

The glt-1 overexpression vector pAN52-glt was linearized by Bgl II and then intergrated into the *Myceliophthora thermophila* JG207 strains genome. The final concentration was 100 μg/mL. G418 was used as screening antibiotic. The method was shown in step 2 of example 1. The transformant was verified and obtained using primers MtPgpdA-F and GLT-R. The PCR system and methods were described in step 1.3 of example 1.

All of the verified transformants were inoculated into a 250 mL triangular flask containing 50 mL of medium with glucose and cellulose as the carbon source (see step 3 in example 1) at an inoculation amount of $2.5 \times 10^5$/mL. The product was subjected to culture at 45° C. at 150 rpm. The sample was taken on the eighth day. After the sample was treated by the method as described in step 3.2 of example 1, the malic acid content in the fermentation broth was determined.

The results showed that the overexpression of glt-1 in malic acid-highly producing strain YG207 could significantly promote the capacity for producing malic acid and the strain with the strongest producing ability was named as JG207G. After four days of fermentation, the yield of malic acid was 42 g/L for glucose and 51 g/L for cellulose. Compared to the original strain JG207 (29 g/L), the yield was increased by 45% and 75%, respectively. The results showed that the overexpression of glucose transporter gene in *Myceliophthora thermophila* strain JG207 could effectively improve the capacity for producing malic acid by fermentation.

Figure 8:
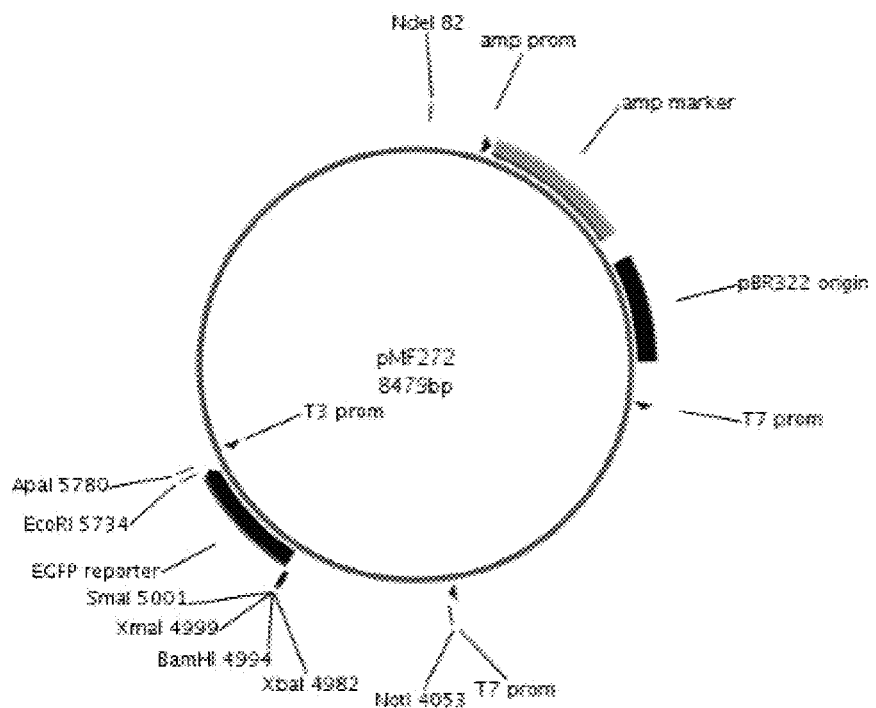
FIG. 8 is a physical map of the plasmid pMF272.

Example 10 Overexpression of C4-Dicarboxylic Acid Transporter in *Neurospora crassa* Failed to Obtain the Capacity for Producing Malic Acid at an Industrial Level 1. Construction of C4-Dicarboxylic Acid Transporter Gene Expression Vector The sequence of nucleic acid encoding C4-dicarboxylic acid transporter gene Ncmae (NCU07517) (SEQ ID NO.: 13) was obtained by PCR amplification using *Neurospora crassa* genome as a template. The primers used for PCR amplification were NCU7517-F:GCTCTAGAATGGGCAGCCAGCCTCCCATGC (SEQ ID NO.: 79) and NCU7517-R:CCTTAATTAACTAATGATCCTCCACATCCTCA (SEQ ID NO.: 80). The sequence of nucleic acid encoding C4-dicarboxylic acid transporter gene mae (NCU07517) (SEQ ID NO.: 11) was obtained by PCR amplification using *Aspergillus oryzae* DSM1863 genome as a template. The primers used for PCR amplification were Asmae-F:
(SEQ ID NO.: 53)
GCTCTAGAATGCTGACACCTCCCAAGTTTGAGGATG mae-2R:
(SEQ ID NO.: 81)
CCTTAATTAACTAATCAGATACATCCTCATCTTTACCC The PCR product of C4-dicarboxylic acid transporter gene fragments obtained through PCR amplification and analysis and the plasmid pMF272 were digested by restriction endonuclease XbaI and PacI (the physical spectrum was shown in FIG. 8). Then they were ligated by T4 DNA ligase to obtain the expression plasmid, named as pMF272-Nrmae and pMF272-mae respectively.

2. Integrating C4-Dicarboxylic Acid Transporter Encoding Gene into *Neurospora crassa* Genome After expression vectors pMF272-Nrmae and pMF272-mae of C4-dicarboxylic acid transporter were transformed into *Neurospora crassa* FGSC9015, the verified transformants were all inoculated into 50 mL of medium in a 250 mL triangular flask containing D-glucose as the carbon source (formula: glucose 100 g/L, peptone 6.0 g/L, 0.15 g/L $KH_2PO_4$, 0.15 g/L $K_2HPO_4$, 0.10 g/L $CaCl_2·2H_2O$, 0.10 g/L $MgSO_4·7H_2O$, Calcium carbonate 80.0 g/L, and 1 ml/L trace elements solution (5 g NaCl, 5 g FeSO4.7H2O, 1 g citric acid/L water) at an inoculation amount of $1×10^6$/mL, and cultured at 25° C. at 200 rpm. On the fourth day, the supernatant was tested to determine the malic acid content in the fermentation broth. The results showed that when Ncmae from *Neurospora crassa* was expressed in *Neurospora crassa* FGSC9015, the highest yield of malic acid was 2.7 g/L and when mae from *Aspergillus oryzae* was expressed in *Neurospora crassa* FGSC9015, the highest yield of malic acid was 2.5 g/L. Compared to the control strain *Neurospora crassa* FGSC9015 (with a yield of 1.5 g/L), the expression of C4-dicarboxylic acid transporter was increased, but it could not meet the needs of industrial applications.

This experiment showed that the capacity for producing malic acid can not be effectively increased to an industrial level by modifying the malic acid synthesis pathway (such as overexpression of malate transporter) in these non-dominant strains of organic acids accumulation, such as *Neurospora crassa*. Although it had been reported that in *Aspergillus* the dominant strain of organic acid accumulation, the capacity for producing malic acid can be effectively increased to an industrial level by modifying the malic acid synthesis pathway, the capacity could not be promoted to these non-dominant strains of organic acid accumulation.

Example 11 Overexpression of C4-Dicarboxylic Acid Transporter in *Trichoderma Reesei* Failed to Improve the Ability of Microorganisms to Produce Malic Acid 1. Construction of C4-Dicarboxylic Acid Transporter (SEQ ID NO.: 11) Overexpression Vector in *Aspergillus oryzae*

Encoding reading frame mae (SEQ ID NO.: 11) of C4-dicarboxylic acid transporter gene was amplified by PCR from cDNA of *Aspergillus* DSM1863, and the primers were as follows:

Amae-F:
(SEQ ID NO.: 82)
TTCCAACTAGTATGCTGACACCTCCCAAG

Amae-R:
(SEQ ID NO.: 83)
AATGGTTAACCTAATCAGATACATCCTC

After the PCR reaction, the PCR product was digested with restriction endonuclease SpeI and HpaI and ligated into the SpeI and HpaI digestion sites of plasmid pCY01 (containing hygromycin resistance gene, and on both sides of the polyclonal digestion site are promoters of elongation factor of *Myceliophthora thermophila* and terminators of *Aspergillus* trpC) to obtain plasmid pNEO-Amae. Plasmid pNEO-Amae was transformed into *Trichoderma reesei* QM6a by protoplast method, and the obtained transformants were QM6a-Amae.

2. Detecting the Acid-Producing Ability of the Recombinant Strains Obtained by Overexpressing C4-Dicarboxylic Acid Transporter in *Trichoderma reesei*

$1.25×10^7$ spores were inoculated to 50 mL of acid-producing medium which was the same as that described in Example, and the product was cultured in 150 rpm at 28 degrees for 8 days. 1 mL of fermentation liquid was added to the 1 mL of 2M sulfuric acid, and reacted at 80 degrees for 20 min. To the above was added 2 mL of water, and centrifuged at 14000 rpm for 10 min after mixing. The supernant was tested to determine the content of malic acid using HPLC as described in Example 1. The yield of malic acid in the original strain was 2.5±0.6 g/L and that in the transformant was 2.4±0.4 g/L.

The results showed that the expression of C4-dicarboxylic acid transporter in *Ttrichoderma reesei* failed to improve the ability for producing malic acid to industrial level.

This experiment showed that the capacity for producing malic acid can not be effectively increased to an industrial level by modifying the malic acid synthesis pathway (such as overexpression of malate transporter) in these non-dominant strains of organic acids accumulation, such as *Trichoderma reesei*. Although it had been reported that in *Aspergillus* the dominant strain of organic acid accumulation the capacity for malic acid can not be effectively increased to an industrial level by modifying the malic acid synthesis pathway, the capacity could not be promoted to these non-dominant strains of organic acid accumulation.

Example 12 Overexpression of Mae and Pyc in Thermophilic Fungi *Myceliophthora heterothallica* Enables the Strain have the Ability to Produce Malic Acid This example showed that when pyruvate carboxylase and C4-dicarboxylic acid transporter were expressed in *M. heterothallica*, the obtained recombinant microorganisms could significantly increase malic acid-producing capacity.

The vector pAN52-mar-pyc expressing mae and pyc (the construction of which was described in Step 1 of Example 1) was screened to obtain several positive transformants in the protoplast transformed strain *M. heterothallica* CBS202.75 with hygromycin gene hph as the selective marker. The positive transformants were subjected to malic acid fermentation with 7.5% microcrystalline cellulose Avicel as the substrate and the medium composition was found in Example 1, Step 3. With *M. heterothallica* CBS202.75 as a reference, the yield of malic acid on the eighth day of the fermentation had been increased up to 47.4 g/L.

This experiment showed that the modification through metabolic engineering could significantly improve the ability to synthesize malic acid in *Trichoderma harzianum*.

Compared with Examples 9 and 10 of the present invention, it could be found that the modified *Myceliophthora* strains could significantly improve the organic acid (malic acid) synthesis, however, which was not predictable.

Example 13 Establishment of Fermentation Process to Produce Malic Acid in Recombinant *Myceliophthora thermophila*

1. Culturing the spore: The recombinant *Myceliophthora thermophila* JG207 was fermented in 5 L fermentor (BIO-TECH-5JG, Shanghai Baoxing Biological Equipment Engineering Co., Ltd.) as follows: recombinant *Myceliophthora thermophila* JG207 was inoculated into MM plate medium and the plates were placed in an incubator at 45° C. for 8 days, and spores were washed with 0.8% NaCl and 0.1% Tween-80 and counted.

2. Culturing the seed liquid: $2.5 \times 10^7$ spores were transferred to a 250 mL triangle flask containing 100 mL of seed medium, which was cultured at 45° C. in 150 rpm for 24 h and then the obtained liquid was taken as the seed for fermentation. The seeds were fermented using a synthetic medium. In a 5 L fermentation tank was loaded with 3.3 L fermentation medium and 400 mL seed liquid.

The composition of MM solid medium (per liter) was 20 g sucrose, 20 mL 50×Vogel's salt, and 15 g agar. The composition of 50×Vogel's salt (g/L) was: 125 g $Na_3$citrate. $2H_2O$, 250 g $KH_2PO_4$, 100 g $NH_4NO_3$, 10 g $MgSO_4 \cdot 7H_2O$, 0.1 g $CaCl_2 \cdot 2H_2O$, 5 mL trace element solution, 2.5 mL Biotin, and 755 mL water.

The composition of seed medium (per liter) was 10 g glucose, 0.15 g $K_2HPO_4$, 0.15 g $KH_2PO_4$, 0.1 g $MgSO_4 \cdot 7H_2O$, 0.1 g CaC12, 6 g Bacto, peptone, 1 mL trace element solution. The composition of trace element solutions (g/L) was: 5 g, Citric acid.$1H_2O$, 5 g $ZnSO_4 \cdot 7H_2O$, 1 g $Fe(NH_4)_2(SO_4)_2 \cdot 6H_2O$, 0.25 g $CuSO_4 \cdot 5H_2O$, 0.05 g $MnSO_4 \cdot 1H_2O$, 0.05 g, $H_3BO_3$, and 0.05 g $Na_2MoO_4 \cdot 2H_2O$.

The composition of fermentation medium (per liter) was: 75 g carbon source, 80 g $CaCO_3$, 0.15 g $K_2HPO_4$, 0.15 g $KH_2PO_4$, 0.1 g $MgSO_4 \cdot 7H_2O$, 0.1 g $CaCl_2$, 6 g Bacto peptone, 0.5 mL Biotin, and 1 mL trace element solution.

The composition of feeding medium (per liter) was 0.45 g $K_2HPO_4$, 0.45 g $KH_2PO_4$, 0.3 g $MgSO_4 \cdot 7H_2O$, 0.3 g $CaCl_2$, 18 g Bacto peptone, 1.5 mL Biotin, and 3 mL trace element solutions.

3. Fermentation process: fermentation temperature 45° C., air flow rate 4 L/min, and the dissolved oxygen was control at 30%. In order to control the dissolved oxygen at 30%, the speed needed to be coupled with the dissolved oxygen, and kept at 200-800 rpm. During the fermentation process calcium carbonate was added to control pH at more than 6.

In the 48th hour during fermentation the feeding medium was fed through simulated exponential feeding method with an average feeding rate of 8 mL/h. In the 72 h, 96 h, 120 h, 144 h, 168 h, 192 h, 216 h, and 240 h during the fermentation, 60 g of carbon source was supplemented respectively.

After being fermented for 48 h, every 24 h 1 mL of bacteria liquid was taken and 1 mL of 2M $H_2SO_4$ was added, the mixture was mixed and then treated at high temperature of 80 for 25 min, then to the mixture was add 1 mL of sterile water. The mixture was centrifuged in 14000 rpm for 10 min. The supernatant was tested to determine the content of malic acid using HPLC (Waters e2695 HPLC).

The fermentation cycle is 240 h-264 h and the yield of malic acid can be increased continuously.

The method for producing malic acid by fermentation in recombinant *Myceliophthora thermophila* strains can be conducted with a variety of carbon sources as substrate and was consistent with the above methods. The yield of malic acid was 230 g/L with glucose as the carbon source. The yield of malic acid was 168 g/L with Avicel as the carbon source. The yield of malic acid was 95 g/L with corn stalk as the carbon source.

Example 14 Separation and Preparation of Malic Acid

The separation and preparation of malic acid was generally divided into three steps: extraction of crude malic acid, refinement, and crystallization.

1. Extraction of crude malic acid: the fermentation broth was processed by six steps such as acid hydrolysis, filtration, neutralization, filtration, acid hydrolysis and filtration, so as to obtain the crude malic acid solution. The fermentation broth was put in the acid hydrolysis tank, and then adjusted to pH1.6 using sulfuric acid, and the acid hydrolysis should be carried out with stirring. After the acid hydrolysis was completed, the gypsum slag, bacteria and other precipitates were filtered by plate-and-frame filter press. The filtrate was put in the neutralization tank, and adjusted to pH 7.5 by adding $CaCO_3$ solid and lime milk. The neutralization liquid was placed in the settling tank for 7 h to allow the calcium malate in the solution crystallize sufficiently. After the above calcium salt system was clear, the supernatant was removed. Then the remain was filtered by releasing the filter tank bottom, and the cake was washed with a small amount of cold water to remove most of the soluble impurities. The calcium malate was transferred into the acid hydrolysis tank, to which was added 2 times the weight of warm water. The mixture was stirred into a suspension, adjusted to pH 1.6 by adding sulfuric acid, stirred sequentially for about half an hour, and then stood for several hours, so that the precipitation of gypsum slag was fully precipitated. The gypsum slag in the above system was filtered by the pressure filter. The filtrate was crude malic acid solution containing trace succinic acid and other organic acids, as well as $Ca^{2+}$, $Mg^{2+}$ and other metal ions and pigments, and would be refined in the next step.

2. The refinement of malic acid: ion exchange and activated carbon were combined used for the treatment. The mother liquid of malic acid was successively purified by 5-column purification system comprising CAL granular activated carbon decolorization column, cation exchange resin 732, anion exchange resin D315, BPL column activated carbon adsorption column and cation exchange resin. During the processing, the crude malic acid solution passed through the 5 column system in sequence, and the liquid flew top-down with a flow rate of 7 to 8 L/min. The effluent was tested to monitor the unsaturated fatty acid content by an ultraviolet absorption analyzer. If there was unsaturated fatty acid in the effluent, it should be reprocessed to the anion exchange resin D315 column. The CAL granular activated carbon decolorization column was used for decoloration and removing some unsaturated fatty acids. Cation exchange resin 732 was used to remove metal ions. Anion exchange resin D315 was used to remove succinic acid and other anions.

The malic acid solution with high purity was reduced and concentrated at 70° C. Then it was cooled down to 20° C., and some crystal seeds were added and crystallization was conducted with slow stirring. After 3 h, malic acid was crystallized.

The malic acid crystals was dried under vacuum at a temperature controlled between 40-50° C.

Example 15 the Transformation of Wild Strains with Organic Acid Accumulation Ability and the Detection of their Capacity for Producing Organic Acid In this study, vectors overexpressing malate dehydrogenase, aspartate aminotransferase and glutamic acid-aspartate transporter were constructed respectively and were used to transfer *Aspergillus* (including *Aspergillus niger, Aspergillus sojae, Aspergillus oryzae*) possessing capacity for accumulating organic acid to obtain multiple transformants and glucose was used as the reaction substrate. The method was shown as the method for the combination of construction of each transformant described in the above examples. Their products and yields were identified. Among them, the numbers of the engineered strains upon transformation and the products were shown in table 3:

TABLE 3

| Name of the engineered strain | Characteristics of the engineered strain | original strain |
|---|---|---|
| PM101 | overexpression of malate dehydrogenase | *Aspergillus oryzae* |
| PM102 | Overexpression of malate dehydrogenase + aspartate aminotransferase | *Aspergillus oryzae* |
| PJ103 | overexpression of malate dehydrogenase | *aspergillus sojae* |
| TJ104 | Overexpression of aspartate aminotransferase | *aspergillus sojae* |
| GJ105 | Overexpression of glutamic acid-aspartate transporter | *aspergillus sojae* |
| GM106 | Overexpression of glutamic acid-aspartate transporter | *Aspergillus oryzae* |

The identification results showed that after the corresponding genes were transformed, the capacity for producing malic acid in *Aspergillus sojae* and *Aspergillus oryzae* had been significantly improved, reaching more than 20-60 g/L respectively, wherein the PM102 strain with two genes transformed provided better performance.

Therefore, the gene modification of the invention could significantly improve the acid-producing capacity of the strain which had an accumulation effect for dibasic acid in its original strain.

Discussion

For the fermentation of organic acids such as malic acid, the traditional dominant strains are *Aspergillus* strains (preferably *Aspergillus niger*-citric acid, itaconic acid-*Aspergillus terreus*, malic acid-*Aspergillus flavus, Aspergillus oryzae*) and *Rhizopus* strains (*Rhizopus oryzae*-lactic acid), while *Trichoderma* and *Neurospora* strains do not belong to the strains that commonly accumulating organic acid. The test has showed that for these strains without significant accumulation of organic acids under the natural conditions, it usually can not effectively improve the production to an industrial level (10 g/L or more) by modifying their organic acid (such as malic acid) synthetic pathway. It has showed that this conclusion can not be applied to the entire filamentous fungi although the modification of synthetic pathway of organic acids in *Aspergillus* has significantly improved the synthesis of organic acids, especially for those non-organic acid accumulation strains, including *Myceliophthora*. it can not be speculated if they have the capacity to synthesize the organic acid at an industrial level. More specific experimental researches are needed. It was unexpected that the inventors of the present invention had firstly demonstrated that *Myceliophthora* strain did not accumulate organic acids in a large amount (usually no more than grams/liter) in the culture medium under natural conditions but can provide industrialized malic acid fermentation ability (10-100 g/l and above) after transformation. Therefore, the present invention has great contingency and innovativeness.

Meanwhile, the inventors have found that not only the malic acid (and even organic acid) fermentation in *Myceliophthora* can be enhanced through regulating multiple new genes, but also the organic acid-producing capacity of strains including *Aspergillus* (preferably *Aspergillus oryzae, Aspergillus sojae*) and so on (beside *Myceliophthora* with accumulation ability of the organic acid) can be improved by genetic modification.

In addition, the inventors have established and optimized the high temperature fermentation process of *Myceliophthora thermophila*, including the fermentation feeding process by using solid biomass such as glucose and other soluble sugar fermentation process and cellulose and the like as the carbon source.

All documents mentioned in the present invention are incorporated herein by reference, as if each document were individually recited for reference. It should be understood that those skilled in the art will be able to make various changes or modifications to the present invention after reading the teachings of the present invention, which also fall within the scope of the claims appended hereto.

The invention claimed is:

1. An engineered strain for synthesizing a dibasic organic acid, wherein the engineered strain is capable of producing the dibasic organic acid at a fermentation temperature of 40-60° C. by using glycan and/or biomass as a fermentation substrate,
   wherein the original strain of the engineered strain is selected from the group consisting of *Myceliophthora thermophila* and *Myceliophthora heterothallica*;
   the engineered strain is introduced with a positive regulator gene for synthesizing the dibasic organic acid, up-regulates expression of the positive regulator gene for synthesizing the dibasic organic acid, and/or down-regulates expression of a negative regulator gene for synthesizing the dibasic organic acid,
   wherein an expression product of the positive regulator gene comprises one or more polypeptides selected from the group consisting of aspartate aminotransferase, glutamic acid-aspartate transporter, and glucose transporter;
   an expression product of the negative regulatory gene comprises one or more polypeptides selected from the group consisting of Succinyl-CoA synthase and Malic acid-alpha ketoglutarate transporter; and
   the dibasic organic acid comprises malic acid, succinic acid, or fumaric acid.

2. The engineered strain of claim 1, wherein n, the engineered strain increases or improves the capacity for producing dibasic organic acid by at least 10%, as compared to the original strain of the engineered strain.

3. The engineered strain of claim 1, wherein the glycan comprises cellulose, crystalline cellulose, hemicellulose, or starch, or a combination thereof.

4. The engineered strain of claim 1, wherein the biomass comprises crop straw, forestry waste, paper-making industry waste, cotton textile industry waste, or energy plant or a partial or complete decomposition product thereof;
   wherein the crop straw comprises corn straw, wheat straw, rice straw, sorghum straw, soybean straw, cotton straw, bagasse, or corncob;
   the forestry waste comprises branches, leaves, or sawdust;
   the paper-making industry waste comprises pulp residue or pulp waste;
   the cotton textile waste comprises wasted cotton or cotton textiles;
   the energy plant comprises sweet sorghum, switchgrass, miscanthus, or reed, or a combination thereof.

5. The engineered strain of claim 1, wherein the fermentation substrate consists of glycans and/or biomass.

6. The engineered strain of claim 1, wherein the fermentation temperature is 40-55° C.

7. The engineered strain of claim 1, wherein the original strain of the engineered strain is *Myceliophthora thermophila*.

8. The engineered strain of claim 1, wherein the engineered strain provides a fermentation yield of dibasic organic acid at least more than 10 g/L based on volume of fermentation liquid; and/or
   as compared to a the original strain of the engineered strain, the engineered strain increases or improves a capacity for producing dibasic organic acid by at least 10%.

9. The engineered strain of claim 1, wherein expression product of the positive regulator gene further comprises one or more polypeptides selected from the group consisting of C4-dicarboxylic acid transporter, pyruvate carboxylase, malate dehydrogenase, and glucose transporter.

10. The engineered strain of claim 1, wherein the fermentation temperature is 48-50° C., and the engineered strain has a fermentation yield of the dibasic organic acid at least more than 10 g/L.

11. The engineered strain of claim 1, wherein the engineered strain comprises an expression vector containing the positive regulator gene or the negative regulator gene, and the positive regulator gene and the negative regulator gene are heterologous genes.

12. The engineered strain of claim 1, wherein the engineered strain increases or improves the capacity for producing dibasic organic acid by 10%-50%, as compared to the original strain of the engineered strain.

13. The engineered strain of claim 1, wherein the engineered strain increases or improves the capacity for producing dibasic organic acid by 50%-500%, as compared to the original strain of the engineered strain.

14. The engineered strain of claim 3, wherein the starch is corn, cassava, and/or wheat.

15. The engineered strain of claim 1, wherein the fermentation temperature is 45-53° C.

16. The engineered strain of claim 1, wherein the engineered strain provides a fermentation yield of dibasic organic acid at 10-50 g/L based on volume of fermentation liquid; and/or
   as compared to a wild type strain of the engineered strain, the engineered strain increases or improves a capacity for producing dibasic organic acid by 10-50%.

17. The engineered strain of claim 1, wherein the engineered strain provides a fermentation yield of dibasic organic acid at 50-300 g/L, based on volume of fermentation liquid; and/or
   as compared to a wild type strain of the engineered strain, the engineered strain increases or improves a capacity for producing dibasic organic acid by 50%-500%.

* * * * *